US011406320B2

(12) United States Patent
Sutaria et al.

(10) Patent No.: US 11,406,320 B2
(45) Date of Patent: Aug. 9, 2022

(54) METHODS AND APPARATUS FOR GUIDING MEDICAL CARE BASED ON SENSOR DATA FROM THE GASTROINTESTINAL TRACT

(71) Applicant: Gravitas Medical, Inc., San Francisco, CA (US)

(72) Inventors: Saheel Sutaria, Albany, CA (US); Eliott Bennett-Guerrero, Setauket, NY (US); Braden Eliason, Minneapolis, MN (US); Arthur Spivy, Vienna, VA (US); Daniel R. Burnett, San Francisco, CA (US)

(73) Assignee: Gravitas Medical, Inc., San Francisco, CA (US)

( * ) Notice: Subject to any disclaimer, the term of this patent is extended or adjusted under 35 U.S.C. 154(b) by 0 days.

(21) Appl. No.: 15/811,433

(22) Filed: Nov. 13, 2017

(65) Prior Publication Data

US 2018/0078195 A1    Mar. 22, 2018

Related U.S. Application Data

(63) Continuation of application No. PCT/US2016/033335, filed on May 19, 2016.
(Continued)

(51) Int. Cl.
  *A61B 5/00* (2006.01)
  *A61B 5/107* (2006.01)
  (Continued)

(52) U.S. Cl.
  CPC .......... *A61B 5/4238* (2013.01); *A61B 5/0536* (2013.01); *A61B 5/0538* (2013.01);
  (Continued)

(58) Field of Classification Search
  CPC ....... A61B 5/036; A61B 5/037; A61B 5/0538; A61B 5/053; A61B 5/14503;
  (Continued)

(56) References Cited

U.S. PATENT DOCUMENTS 4,836,214 A    6/1989  Sramek
4,921,481 A *  5/1990  Danis ................. A61J 15/0003
                                                  604/67
(Continued)

FOREIGN PATENT DOCUMENTS

JP     2004-523328      8/2004
JP     2008-049160      3/2008
(Continued)

OTHER PUBLICATIONS

Bredenoord, et al. "Technology review: esophageal impedance monitoring." The American journal of gastroenterology 102.1 (2007): 187.*

(Continued)

*Primary Examiner* — David J. McCrosky
(74) *Attorney, Agent, or Firm* — Levine Bagade Han LLP

(57) ABSTRACT

Methods and apparatus for guiding medical care based on sensor data from the gastrointestinal tract are described utilizing an apparatus which can be used with enteral feeding. Generally, the apparatus includes an elongated body having a length configured for insertion into a stomach and at least one pair of electrodes located along the length of the elongated body and positionable for placement within the stomach. A controller in electrical communication with the at least one pair of electrodes is included and the control may also be configured to measure a conductivity or impedance between the pair of electrodes and to determine a gastric residual volume of the stomach based on the measured conductivity or impedance.

33 Claims, 52 Drawing Sheets

Related U.S. Application Data

(60) Provisional application No. 62/312,257, filed on Mar. 23, 2016, provisional application No. 62/258,329, filed on Nov. 20, 2015, provisional application No. 62/185,697, filed on Jun. 28, 2015, provisional application No. 62/164,488, filed on May 20, 2015.

(51) Int. Cl.
| | | |
|---|---|---|
| *A61B 5/145* | (2006.01) | |
| *A61B 5/1473* | (2006.01) | |
| *A61J 15/00* | (2006.01) | |
| *A61B 5/0536* | (2021.01) | |
| *A61B 7/00* | (2006.01) | |
| *A61B 5/318* | (2021.01) | |
| *A61M 1/00* | (2006.01) | |
| *A61B 5/0538* | (2021.01) | |
| *A61B 5/06* | (2006.01) | |
| *A61B 5/01* | (2006.01) | |
| *A61B 5/08* | (2006.01) | |
| *A61B 5/287* | (2021.01) | |
| *A61B 5/05* | (2021.01) | |
| *A61B 7/04* | (2006.01) | |
| *A61B 17/12* | (2006.01) | |

(52) U.S. Cl.
CPC .............. *A61B 5/065* (2013.01); *A61B 5/068* (2013.01); *A61B 5/1073* (2013.01); *A61B 5/1473* (2013.01); *A61B 5/14539* (2013.01); *A61B 5/318* (2021.01); *A61B 7/00* (2013.01); *A61B 7/003* (2013.01); *A61J 15/0084* (2015.05); *A61M 1/73* (2021.05); *A61B 5/01* (2013.01); *A61B 5/05* (2013.01); *A61B 5/0816* (2013.01); *A61B 5/14503* (2013.01); *A61B 5/287* (2021.01); *A61B 5/4205* (2013.01); *A61B 5/4211* (2013.01); *A61B 5/4233* (2013.01); *A61B 5/4836* (2013.01); *A61B 5/6852* (2013.01); *A61B 5/6898* (2013.01); *A61B 5/7282* (2013.01); *A61B 5/746* (2013.01); *A61B 7/04* (2013.01); *A61B 17/12136* (2013.01); *A61B 2562/0204* (2013.01); *A61B 2562/043* (2013.01); *A61J 15/0088* (2015.05); *A61M 1/84* (2021.05); *A61M 2205/3324* (2013.01); *A61M 2210/105* (2013.01); *A61M 2210/1053* (2013.01)

(58) Field of Classification Search
CPC ............ A61B 5/14507; A61B 5/14539; A61B 5/14546; A61B 5/42; A61B 5/4233; A61B 5/4238; A61J 15/0003; A61J 15/0007; A61J 15/008; A61J 15/0084; A61M 2205/3324; A61M 2210/1042; A61M 2210/105; A61M 2210/1053
See application file for complete search history.

(56) References Cited

U.S. PATENT DOCUMENTS

| | | |
|---|---|---|
| 6,334,064 B1 | 12/2001 | Fiddian-green |
| 6,357,447 B1 | 3/2002 | Swanson et al. |
| 7,818,155 B2 | 10/2010 | Stuebe et al. |
| 8,147,486 B2 | 4/2012 | Honour et al. |
| 8,149,418 B2 | 4/2012 | Tearney et al. |
| 8,285,399 B2 | 10/2012 | Van Bommel et al. |
| 8,403,884 B2 | 3/2013 | Nishtala |
| 8,613,702 B2 | 12/2013 | Feer et al. |
| 8,750,974 B2 | 6/2014 | Baker et al. |
| 8,845,533 B2 | 9/2014 | Addington et al. |
| 8,986,230 B2 | 3/2015 | Nishtala |
| 9,179,971 B2 | 11/2015 | Kirschenman |
| 9,226,878 B2 | 1/2016 | Elia et al. |
| 9,295,395 B2 | 3/2016 | Elia et al. |
| 9,532,739 B2 | 1/2017 | Bennett-Guerrero |
| 9,610,227 B2 | 4/2017 | Elia |
| 9,642,779 B2 * | 5/2017 | Elia ..................... A61J 15/0084 |
| 9,713,579 B2 * | 7/2017 | Elia ........................ A61B 5/746 |
| 2008/0033400 A1 | 2/2008 | Holper et al. |
| 2008/0077043 A1 * | 3/2008 | Malbrain ............ A61J 15/0084 |
| | | 600/547 |
| 2008/0097179 A1 | 4/2008 | Russo |
| 2008/0167607 A1 | 7/2008 | Pfeiffer et al. |
| 2009/0131012 A1 | 5/2009 | Ashley, Jr. et al. |
| 2009/0187164 A1 | 7/2009 | Rowe |
| 2010/0016839 A1 | 1/2010 | Shehata |
| 2010/0030133 A1 | 2/2010 | Elia et al. |
| 2011/0060215 A1 * | 3/2011 | Tupin, Jr. ............. A61B 5/0507 |
| | | 600/425 |
| 2012/0016256 A1 | 1/2012 | Mabary et al. |
| 2012/0277619 A1 | 11/2012 | Starkebaum et al. |
| 2012/0310269 A1 | 12/2012 | Fearnot et al. |
| 2012/0323091 A1 | 12/2012 | Bennett-Guerrero et al. |
| 2013/0158514 A1 * | 6/2013 | Elia ..................... A61B 5/4277 |
| | | 604/516 |
| 2013/0225946 A1 | 8/2013 | Feer et al. |
| 2016/0113843 A1 | 4/2016 | Elia et al. |
| 2016/0129223 A1 | 5/2016 | Kirschenman |
| 2016/0143817 A1 * | 5/2016 | Elia ..................... A61B 5/4238 |
| | | 604/503 |
| 2017/0202750 A1 | 7/2017 | Elia |
| 2018/0161249 A1 | 6/2018 | Elia et al. |

FOREIGN PATENT DOCUMENTS

| | | | |
|---|---|---|---|
| WO | WO 1992/017150 | 10/1992 | |
| WO | WO 2009/049266 | 8/2009 | |
| WO | WO-2015120285 A1 * | 8/2015 | ........... A61B 1/2736 |
| WO | WO 2016/187456 | 11/2016 | |

OTHER PUBLICATIONS

Soulsby, et al. "Measurements of gastric emptying during continuous nasogastric infusion of liquid feed: electric impedance tomography versus gamma scintigraphy." Clinical Nutrition 25.4 (2006): 671-680.*

Duquia et al. "Presenting data in tables and charts." An Bras Dermatol. 2014;89(2):280-5.*

Internet Archive, PrismNet, "Online Technical Writing: Tables, Charts, Graphs". Retrieved from <https://web.archive.org/web/20130513070959/https://www.prismnet.com/~hcexres/textbook/tables.html> on Aug. 13, 2018.*

Sacks, Gordon S. "Drug-nutrient considerations in patients receiving parenteral and enteral nutrition." Practical Gastroenterology 28.7 (2004): 39-49. (Year: 2004).*

* cited by examiner

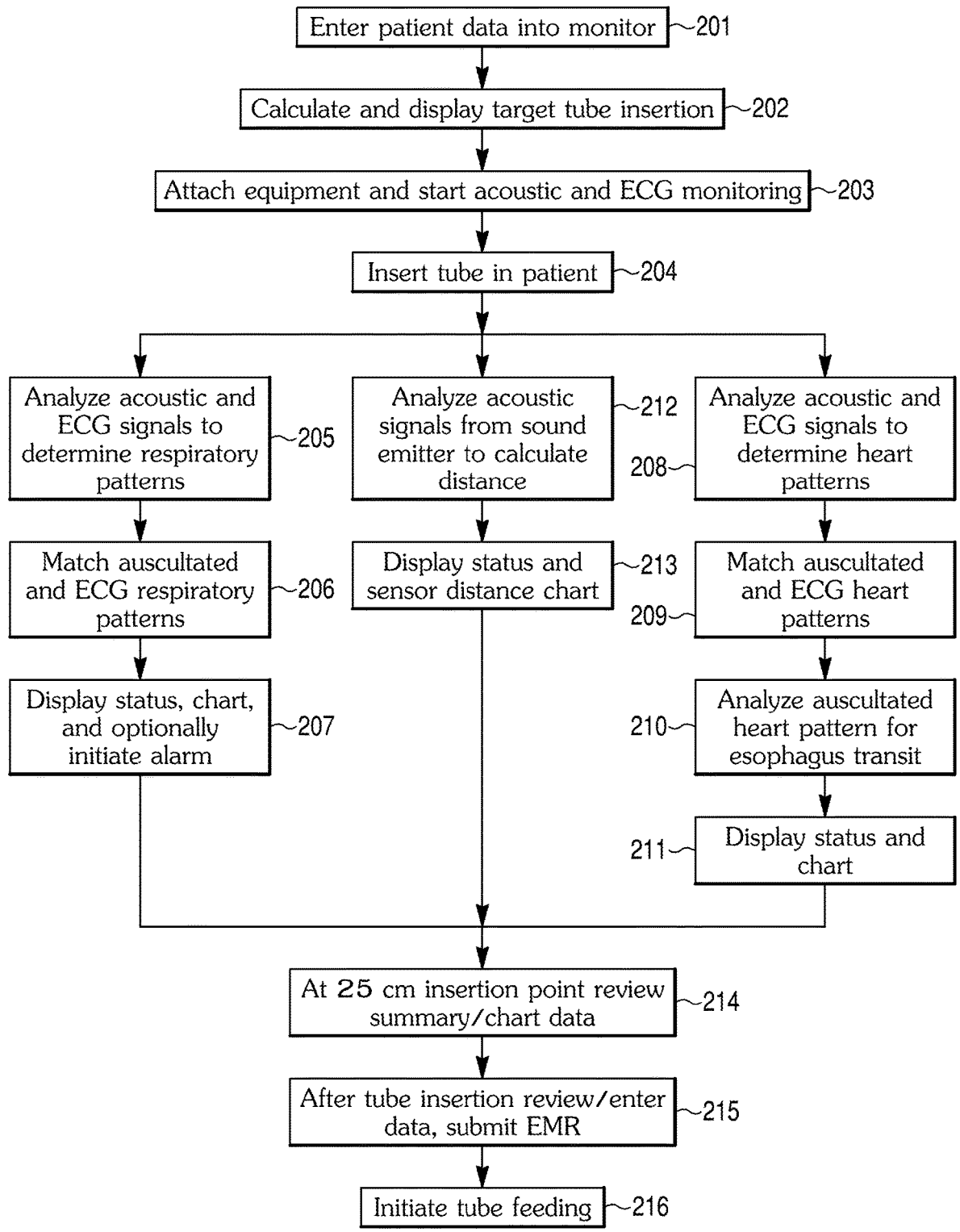

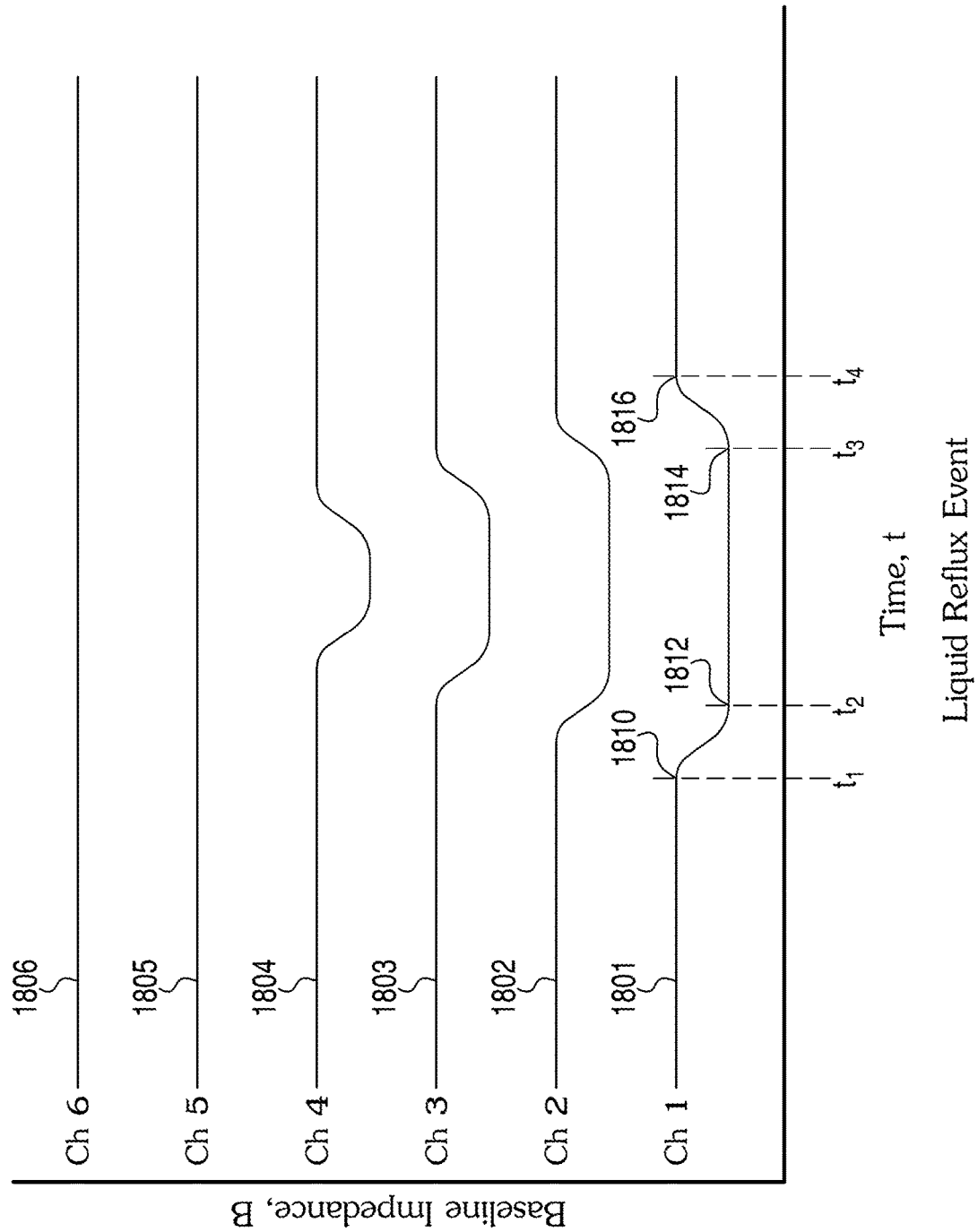

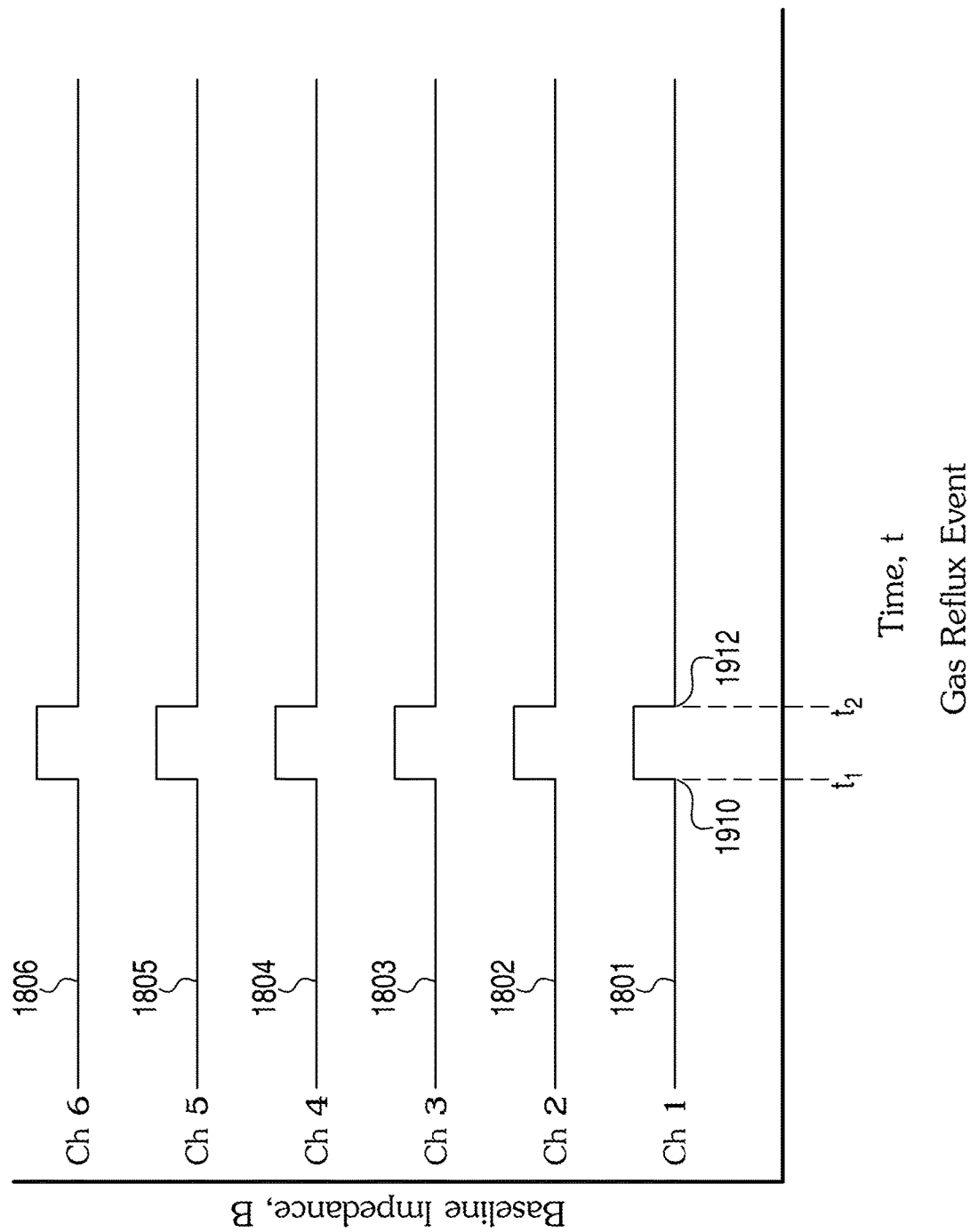

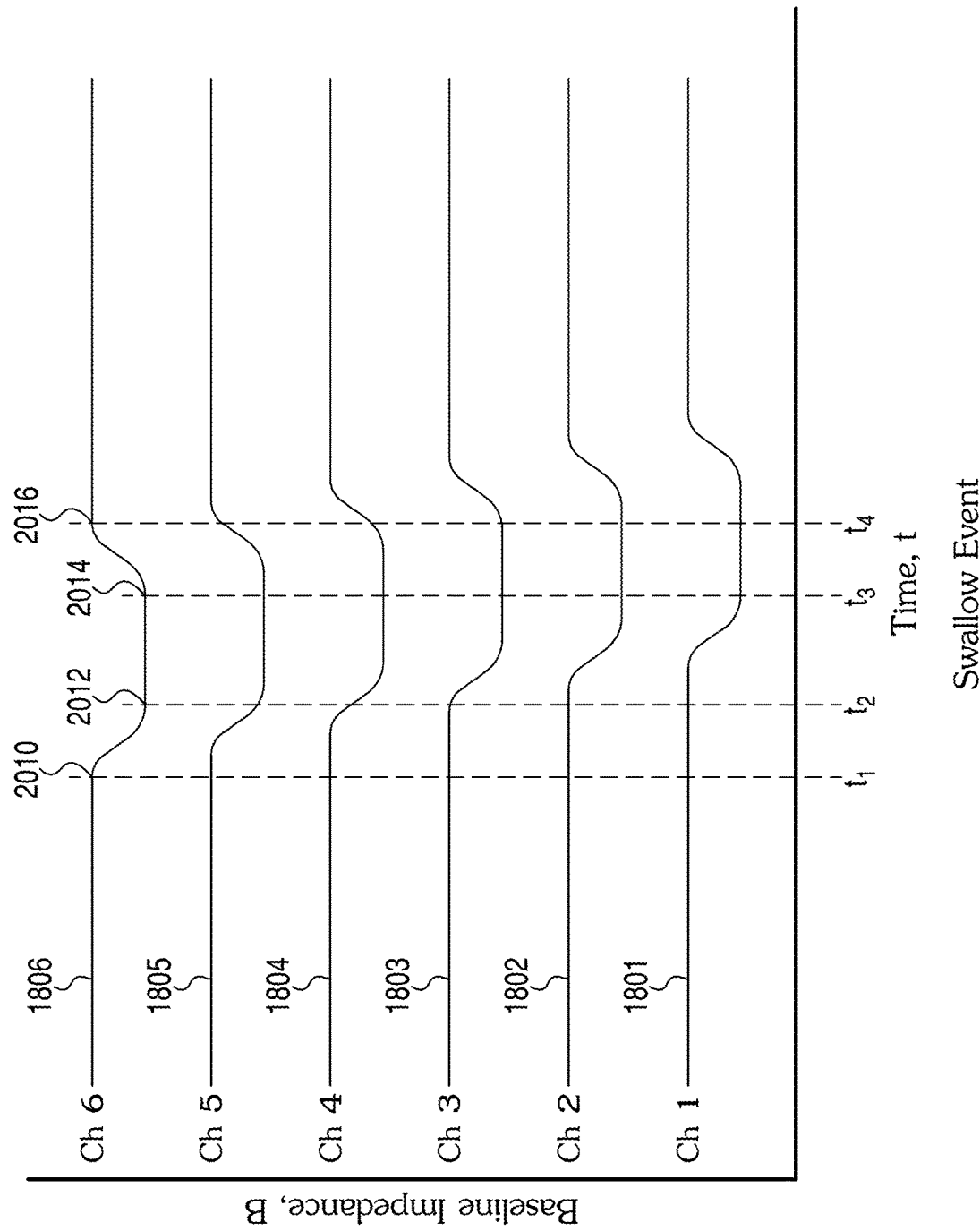

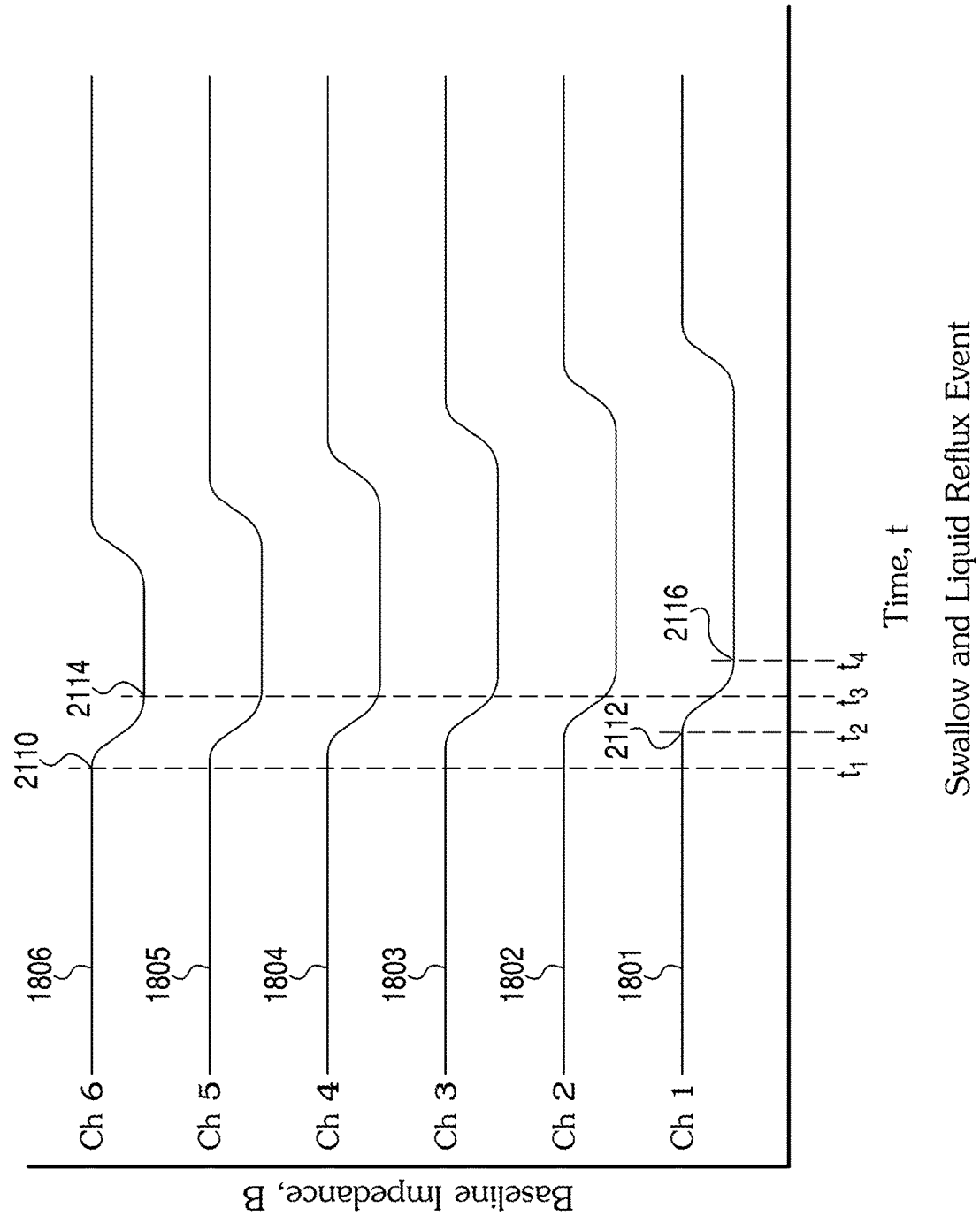

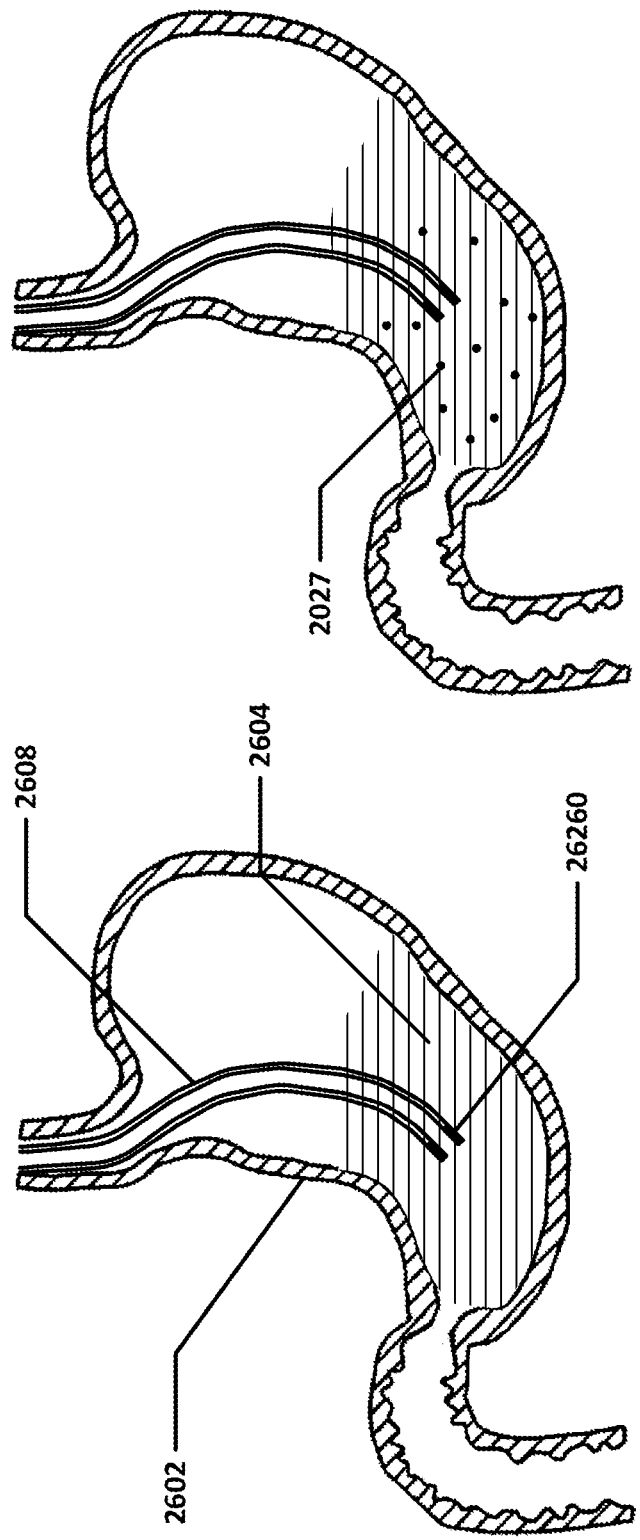

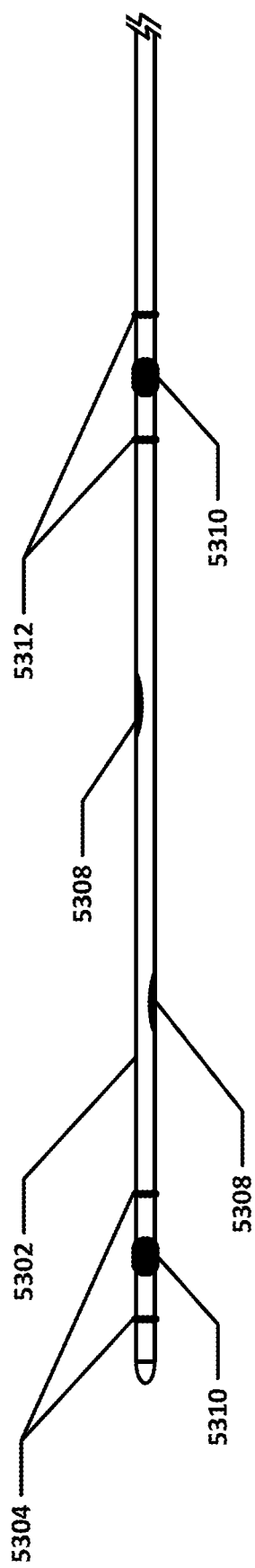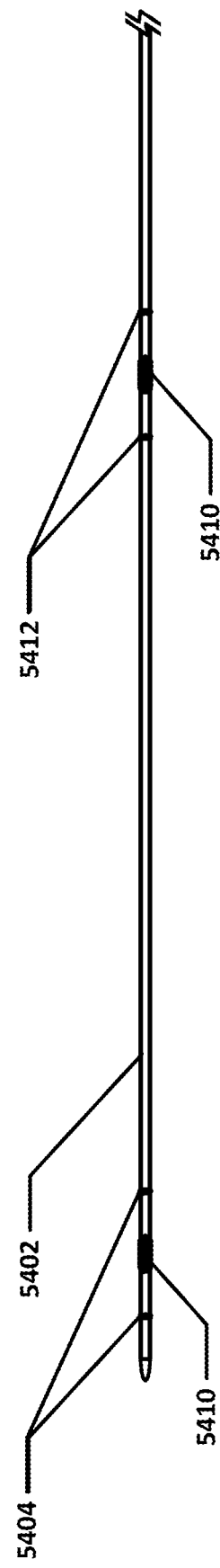
FIG. 53
FIG. 54

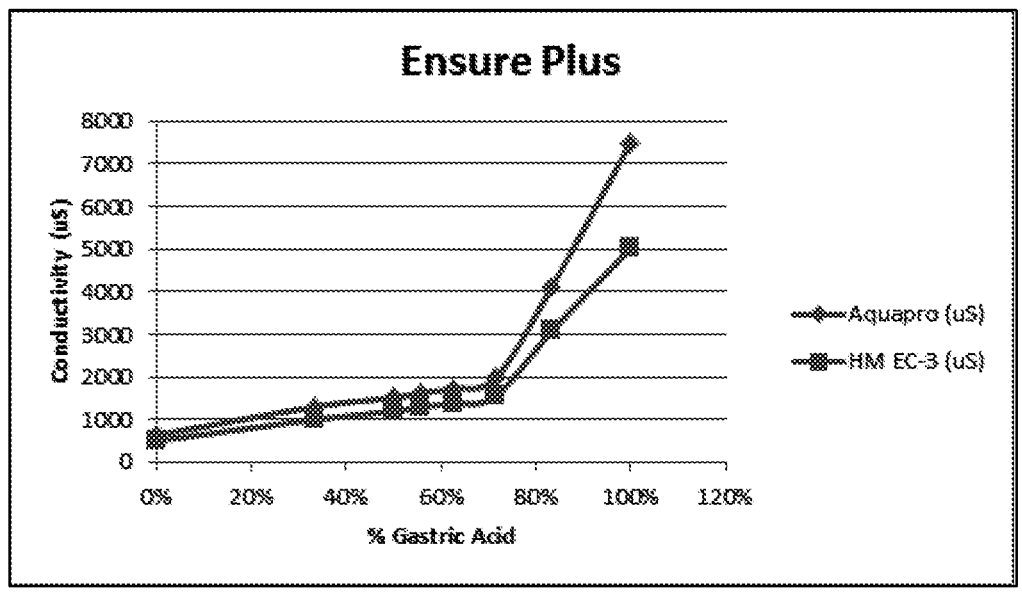
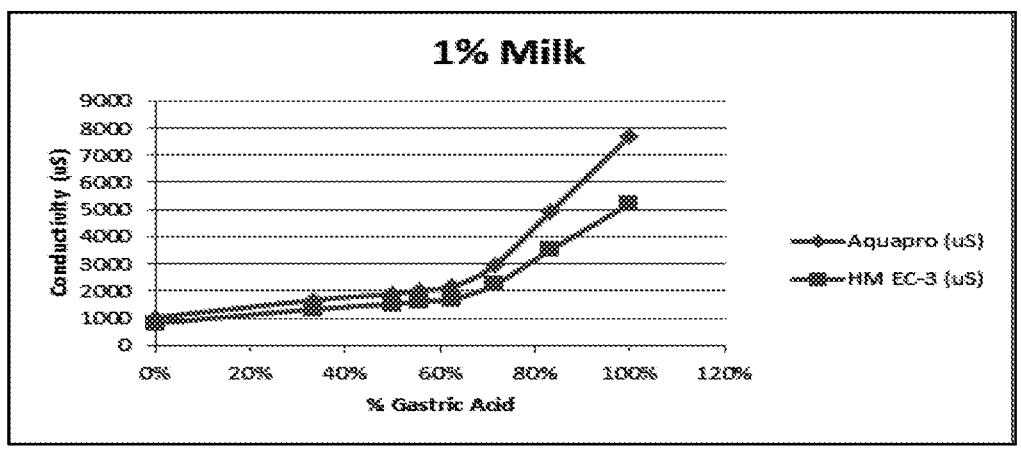
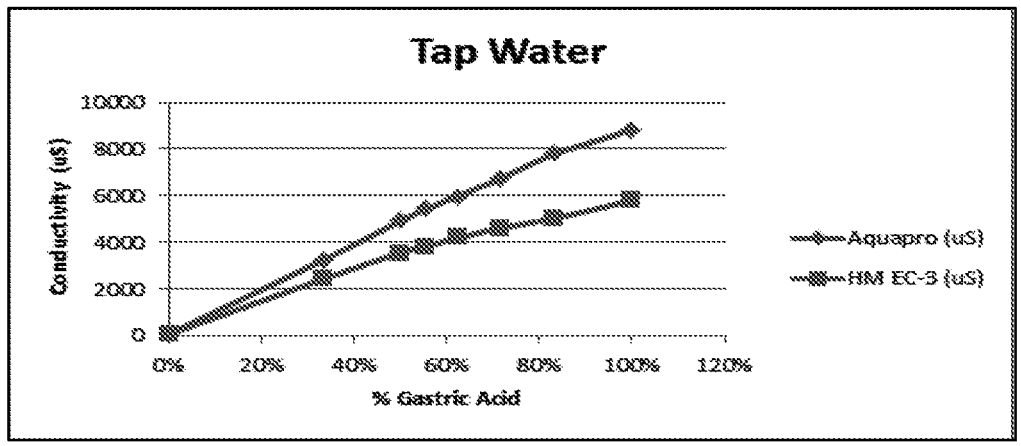
FIG. 55

METHODS AND APPARATUS FOR GUIDING MEDICAL CARE BASED ON SENSOR DATA FROM THE GASTROINTESTINAL TRACT

CROSS-REFERENCE TO RELATED APPLICATIONS

This application is a continuation of International Patent Application No. PCT/US2016/033335 filed May 19, 2016, which claims the benefit of priority to U.S. Provisional Application No. 62/164,488 filed May 20, 2015, U.S. Provisional Application No. 62/258,329 filed Nov. 20, 2015, U.S. Provisional Application No. 62/185,697 filed Jun. 28, 2015, U.S. Provisional Application No. 62/312,257 filed Mar. 23, 2016, each of which is incorporated herein by reference in its entirety.

FIELD OF THE INVENTION

The present invention relates to the measuring of gastric volume, gastric emptying, reflux, and feeding tube placement/monitoring.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

The provision of adequate nutrition is widely recognized as important for recovery from acute illnesses. Nutritional support is often required for intensive care unit (ICU) patients, hospital ward patients, and nursing home patients. Results from 14 randomized trials demonstrated 41% lower mortality and 27% fewer infectious complications in ICU patients randomized to early (vs. delayed) enteral nutrition according to Heyland et al, "Review of ICU Early vs. Delayed Feeding Randomized Trials." JPEN, 2003; 27:355-73, hereafter "Heyland" which is hereby incorporated in its entirety herein by reference. Patients receiving early enteral nutrition had a shorter ICU length of stay (4.7 vs 8.5 days), shorter time on the ventilator (3.0 vs 6.0 days), and reduced mortality (5.5% vs 38.9%) according to Woo et al., "Early vs delayed enteral nutrition in critically ill medical patients." Nutr Clin Pract. 2010 April; 25(2):205-11, hereafter "Woo" which is hereby incorporated in its entirety herein by reference. Early nutrition was associated with a 20% decrease in ICU mortality and 25% decrease in hospital mortality, but had an attendant 18% increase in the incidence of pneumonia according to Artinian et al, "Effects of early enteral feeding on the outcome of critically ill mechanically ventilated medical patients." Chest. 2006 April; 129(4):960-7, hereafter "Artinian" which is hereby incorporated in its entirety herein by reference. The Society of Critical Care Medicine (SCCM) and the American Society of Parenteral and Enteral Nutrition (ASPEN) guidelines recommend early nutrition.

While guidelines recommend feeding patients early, many acute care patients may not be ready for nutrition, as evidenced by a study where up to 62.8% of ICU patients exhibited signs of feeding intolerance, and where feeding intolerance was subsequently associated with higher mortality (31% vs 16%, p<0.001) according to JC Montejo, "Enteral nutrition-related gastrointestinal complications in critically ill patients: a multicenter study." Crit Care Med. 1999 August; 27(8):1447-53, hereafter "Montejo" which is hereby incorporated in its entirety herein by reference.

Clinicians are fearful of feeding patients too early since they may be at risk for aspirating gastric contents into the lungs. Pulmonary aspiration is very common in acute care patients. For example, 62% of hospitalized elderly patients aspirate according to Murry et al., "The significance of accumulated oropharyngeal secretions and swallowing frequency in predicting aspiration." Dysphagia. 1996 Spring; 11(2):99-103, hereafter "Murry" which is hereby incorporated in its entirety herein by reference. Similarly, it has been found that 38% of stroke patients aspirate; in more than ⅔ of these patients, aspiration goes unrecognized by the clinicians caring for them according to Daniels et al, "Aspiration in patients with acute stroke." Arch Phys Med Rehabil. 1998 January; 79(1):14-9, hereafter "Daniels" which is hereby incorporated in its entirety herein by reference. Another study found that 50% of patients with stroke or brain injury aspirate, according to Veis et al, "Swallowing disorders in persons with cerebrovascular accident." Arch Phys Med Rehabil. 1985 June; 66(6):372-5, hereafter "Veis" which is hereby incorporated in its entirety herein by reference.

Aspirating these gastric contents into the lungs can result in devastating consequences, such as chemical pneumonitis or pneumonia, or even death due to asphyxiation. For example, aspiration pneumonia occurred in 19% of elderly hospitalized patients and 44% of nursing home patients according to Langmore et al, "Predictors of aspiration pneumonia in nursing home residents." Dysphagia. 2002 Fall; 17(4):298-307, hereafter "Langmore" which is hereby incorporated in its entirety herein by reference. Stroke patients who aspirate had a 6.95 times greater risk of developing pneumonia than patients who did not aspirate according to Holas et al, "Aspiration and relative risk of medical complications following stroke." Arch Neurol. 1994 October; 51(10):1051-3, hereafter "Holas" which is hereby incorporated in its entirety herein by reference. Pneumonitis (i.e., sterile inflammation) is often misdiagnosed as pneumonia, since pneumonia and pneumonitis (triggered by the presence of gastric juice and particulate matter) can be associated with similar clinical findings. Furthermore, sterile pneumonitis can lead to the development of pneumonia. Thus, 40% of cases of suspected pneumonia in nursing home residents were classified as pneumonitis based on definite or suspected aspiration event according to Mylotte et al, "Pneumonia versus aspiration pneumonitis in nursing home residents: prospective application of a clinical algorithm." J Am Geriatr Soc. 2005 May; 53(5):755-61, hereafter "Mylotte" which is hereby incorporated in its entirety herein by reference. Overall, high mortality rates (>50%) are associated with aspiration pneumonia and pneumonitis according to DeLegge et al, "Aspiration pneumonia: incidence, mortality, and at-risk populations." JPEN J Parenter Enteral Nutr. 2002 November-December; 26(6 Suppl):S19-24; discussion S24-5, hereafter "Delegge" which is hereby incorporated in its entirety herein by reference.

Many acute care patients are at greater risk for developing complications from aspiration because of trouble swallowing, also called dysphagia, impaired gag reflex and/or a compromised immune system. These include patient populations such as the elderly, patients who are heavily sedated, patients suffering from stroke, traumatic brain injury, brain tumor, or head and neck cancer. The following are risk factors for aspiration: gastroesophageal reflux, increased age with physiologic insult, cerebral vascular accident, decreased consciousness, gastroparesis, tracheal intubation, naso/oral enteral intubation, enteral feeding, anesthesia, supine position, seizure according to DeLegge.

Among patients, who are receiving enteral nutrition via (continuous or intermittent) administration of a tube feeding formula into the stomach through an orogastric or (more commonly) a nasogastric feeding tube, the risk of aspiration of gastric contents is increased when gastric emptying into the small intestine is impaired. The most common cause of impaired or delayed gastric emptying is gastric ileus (i.e., gastric dysmotility). When patients are receiving enteral nutrition via continuous administration of a tube feeding formula through a feeding tube, clinicians (nurses and physicians) commonly seek to prevent aspiration by periodic measurements of "gastric residual volume" or GRV. Typically, GRV is estimated by periodically connecting a large syringe to the orogastric or nasogastric feeding tube, and applying suction to remove the gastric contents and then measuring the volume of contents thereby removed. Often, enteral feeding is temporarily discontinued if the measured GRV is greater than some (arbitrarily determined) threshold value (e.g., 200 mL or 300 mL).

This fear of aspiration often results in clinicians underfeeding patients. For example, up to 45% of ICU patients do not receive nutrition during the first 3-5 days after admission to the unit, according to Nguyen et al, "The impact of delaying enteral feeding on gastric emptying, plasma cholecystokinin, and peptide YY concentrations in critically ill patients." Crit Care Med. 2008 May; 36(5):1469-74, hereafter "Nguyen" which is hereby incorporated in its entirety herein by reference. Surgical ICU patients on average started enteral nutrition after 57.8 hours according to Drover et al, "Nutrition Therapy for the Critically Ill Surgical Patient: We Need To Do Better!" JPEN J Parenter Enteral Nutr 2010 34: 644, hereafter "Drover" which is hereby incorporated in its entirety herein by reference.

Gastric contents typically are acidic. If acidic gastric contents enter the esophagus, the result can be the symptoms of acid reflux, such as heartburn, acid indigestion, and burning pain. If the acid reflux progresses further up the esophagus, it can possibly enter the trachea and lungs and result in pulmonary aspiration.

Thus, while clinicians want to feed patients early, they are concerned that patients might be at risk for reflux. Unfortunately, there are no reliable signs to help clinicians determine whether patients are experiencing reflux or may be at risk. The patient population appears to be quite variable with respect to which patients are exhibiting reflux and how much reflux these patients are experiencing. In one study, 22 of 24 (91%) of ventilated pediatric ICU patients exhibited reflux according to Abdel-Gawad et al, "Gastroesophageal reflux in mechanically ventilated pediatric patients and its relation to ventilator-associated pneumonia." Crit Care. 2009; 13(5): R164, hereafter "Abdel-Gawad" which is hereby incorporated in its entirety herein by reference. In this same study by Abdel-Gawad, pneumonia patients had more episodes (6.5) and longer total reflux time (50 min) compared to non-pneumonia patients (1 episode, 3 min). In another study, 6 of 11 (55%) of adult mechanically ventilated ICU patients experienced 25 reflux events, as measured by impedance monitoring according to Nind et al, "Mechanisms of gastroesophageal reflux in critically ill mechanically ventilated patients." Gastroenterology. 2005 March; 128(3):600-6, hereafter "Nind" which is hereby incorporated in its entirety herein by reference. Nind further described how there was significant inter-patient variability with one patient having 13 reflux events and five patients having no reflux events. The incidence in the overall ICU population is likely higher since the Nind study consisted only of a "healthier" population already tolerating enteral nutrition, plus the data were only recorded for one hour prior to feeding and five hours during NG feeding. In another study, 30 of 36 (83%) mechanically ventilated ICU patients aged 1 month to 7 years of age experienced 338 episodes of reflux, with a mean of 9.3 episodes per patient (SD 16, median 2, range 1-79) according to Solana et al, "Multichannel intraluminal impedance to study gastroesophageal reflux in mechanically ventilated children in the first 48 h after PICU admission." Nutrition. 2013 July-August; 29(7-8):972-6, hereafter "Solana" which is hereby incorporated in its entirety herein by reference. Solana also describes how 16 of the 338 episodes were found to reach the superior channels via impedance measurement. The incidence is likely higher since no feeding was done during the measurement timeframe.

Most commonly, feeding tubes are small bore (5 French to 12 French outside diameter) plastic tubes. Very small bore tubes are intrinsically very flexible, and therefore are difficult to pass. Accordingly, very small tubes often are provided with a thin wire stiffener, or stylet, located in the lumen. The stiffening wire, which facilitates insertion of the tube, is removed after the tube has been correctly positioned in the stomach. Most commonly, feeding tubes are inserted into one of the nares. The tube is advanced sequentially through the nasopharynx, oropharynx, hypopharynx, and esophagus, ultimately leading to placement of the distal tip of the tube in the lumen of the stomach. Occasionally, as the tube is being advanced through the hypopharynx, the tube goes through the larynx and enters the trachea, rather than passing into the esophagus. If the feeding tube has a wire stylet and is advanced all the way down the tracheobronchial tree into a distal subsegmental bronchiole, then the lung parenchyma can be perforated, leading to pneumothorax or even formation of a bronchopleural fistula. Even if the tube is not stiffened with a stylet or is not advanced into the distal tracheobronchial tree, the introduction of tube feeding formula into the airways (trachea, mainstem bronchi, or segmental bronchi), can have catastrophic consequences, including pneumonitis, pneumonia or even death. Because clinicians are aware of the risk of inadvertently introducing tube feeding formula into the airways, most institutions mandate radiographic confirmation that the tip of the feeding tube is properly located in the stomach (or the small intestine) prior to initiating tube feeding.

Enteral feeding through a feeding tube allows patients to receive nutrition when he/she cannot receive nutrition through the mouth, cannot swallow safely or to provide supplemental nutrition. Current standard of care requires periodic monitoring of the gastric residual volume (GRV) after feeding. GRV is the volume of residual gastric contents that remain in the stomach after a certain period of time has elapsed after feeding via a feeding tube. The concern is that high GRV values may indicate pulmonary aspiration, a critical issue that could lead to pneumonia with serious consequences. Usually these GRV measurements occur every 4-6 hours, and particularly during the first few days of enteral feeding to allow acceptance of the feeding tube.

The current standard method of determining GRV is via aspiration from a nasogastric tube. There are several issues with the current methods of determining GRV including:

1) Aspiration of contents to measure GRV is a burden on nursing staff. Even with expertise in the procedure, the process takes 5 minutes. With this repeated every 4-6 hours for every patient requiring GRV monitoring.

2) The process of aspirating gastric contents through manual mechanical means may increase the incidence of pulmonary aspiration.

3) Lack of standardization of means to manually measure GRV, whether through aspiration by syringe, low-wall suction, gravity drainage or other method, introduce errors in measurement.

A solution is needed which addresses these and other issues with measuring GRV in patients.

SUMMARY OF THE INVENTION

The present invention is a GRV measuring device and methods which determine the volume of gastric content by introduction of at least one additive component (a GRV indicator) that is dispersed and then changes a physical (chemical, electrical, thermal, mechanical, optical, etc.) characteristic within the stomach contents by a measureable degree. The degree of change of this physical characteristic, and/or the rate of return to the previous state, may be used to determine the GRV of a patient. If the GRV is small, the magnitude of change will likely be greater, and the rate of change of this physical characteristic back to baseline will be slower. If the GRV is large, the magnitude of change will likely be smaller, and the rate of return to baseline will be faster. The determined GRV can also be used to automatically or semi-automatically control the patient's feeding rate and/or volume and/or frequency to adequately nourish the patient but avoid complications. The physical characteristic(s) may also be used to detect that the feeding catheter or tube is in the correct location (i.e. stomach vs lung or esophagus). Note that the term "GRV" may refer to Gastric Residual Volume or Gastric Emptying or Gastric residual feed. Gastric emptying in an indicator of gastric volume, or rate of gastric emptying, either of which can indicate when a patient needs to be fed. The GRV measuring device embodiments disclosed here may measure gastric residual volume, or gastric emptying or gastric residual feed. Specifically, the GRV measuring device embodiments disclosed her may measure gastric food percentage (food vs gastric fluids), gastric residual volume, and/or gastric residual food.

One variation of an apparatus for determining a gastric residual volume may generally comprise an elongate tube defining at least one lumen therethrough, a medium having one or more GRV indicators in fluid communication with the at least one lumen, one or more sensors positioned at or near a distal tip of the elongate tube, wherein the one or more sensors are configured to measure a change in a parameter of the GRV indicators, and a controller in communication with the one or more sensors, wherein the controller is configured to determine a GRV based on the change in the parameter of the GRV indicators.

In use generally, such an apparatus may be used to determine the GRV by positioning the elongate tube defining at least one lumen therethrough into the body lumen, introducing the medium having one or more GRV indicators through the at least one lumen and into the body lumen, and sensing the one or more GRV indicators via one or more sensors positioned at or near a distal tip of the elongate tube. The one or more GRV indicators may be monitored for a change in a parameter of the GRV indicators and the GRV of the stomach may be determined based on the change in the parameter of the GRV indicators.

BRIEF DESCRIPTION OF THE DRAWINGS

Various exemplary embodiments are described in detail with reference to the following figures, wherein:

FIG. 2 is a flowchart of an exemplary method and apparatus for placing a feeding tube;

FIG. 18 is a chart of impedance data indicating a liquid reflux event;

FIG. 19 is a chart of impedance data indicating a gas reflux event;

FIG. 20 is a chart of impedance data indicating a swallow event;

FIG. 21 is a chart of impedance data indicating a swallow and liquid reflux event;

FIG. 26 shows an embodiment of the GRV measuring device in a human stomach.

FIG. 27 shows a stomach into which a substance containing a concentration of a GRV indicator is introduced.

FIG. 38 shows sensor(s) of the GRV measuring device in the pylorus

FIGS. 53 and 54 show other embodiments of the GRV measuring device.

FIG. 55 shows the conductivity of various media when % gastric acid is increased.

DETAILED DESCRIPTION OF THE INVENTION

Figure 1A:
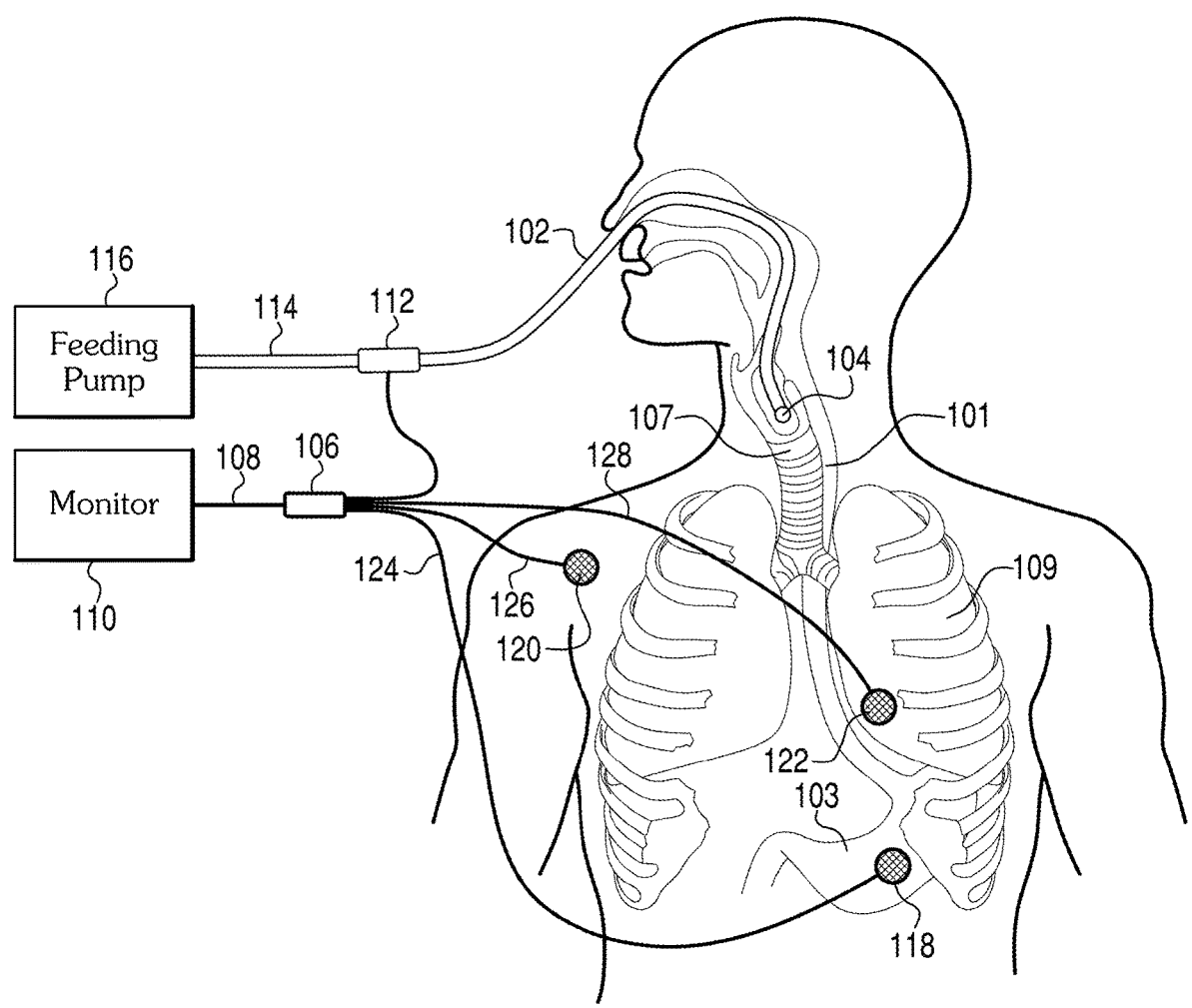
FIGS. 1A-1C are schematics of an apparatus for placing a feeding tube in accordance with an exemplary embodiment.

For convenience of explanation, exemplary embodiments are described below with reference to the figures in the context of placing feeding tubes, assessing gastric motility, and monitoring reflux in acute care patients.

A table of contents of some embodiments specifically disclosed in the Detailed Description is provided below.

I. Feeding Tube Location System and Apparatus
  A. Determine Tube Location Using Acoustic Sensor
  B. Determine Tube Location Using Magnetic Field Sensor
II. Motility Measurement System and Apparatus
  A. Determine Motility Using Acoustic Sensor
  B. Determine Gastric Residual Volume Using Temperature Sensor
  C. Determine Gastric Residual Volume Using Bioelectrical Impedance
  D. Determine Motility Using Impedance Sensors
III. Reflux Measurement System and Apparatus
  A. Reflux Measurement System
  B. Feeding Tube Design
  C. Monitor Cable Design
  D. Suction and Feeding Pump Connector Design
  E. Monitor Design
IV. Impedance Based Algorithms
  A. Data Collection for Algorithms
  B. Algorithms for Detecting Liquid Reflux
  C. Algorithms for Detecting Gas Reflux or Belching
  D. Algorithms for Detecting Swallows
  E. Algorithms for Detecting Mixed Conditions
  F. Algorithms for Smart Alarms
V. Aspiration Prevention Interventions
  A. Aspiration Prevention Via Suction of Gastric Contents
  B. Aspiration Prevention Via Adjustment of Feeding Pump
  C. Aspiration Prevention Via Esophageal Obstruction
VI. Impedance Based Local GRV Measurement
VII. Tube Localization Through Impedance Measurements
VIII. Tube Localization Through Local Conductivity Measurements The present disclosure now will be described more fully hereinafter with reference to the accompanying drawings, in which various embodiments are shown. The invention may, however, be embodied in many different forms and should not be construed as limited to the example embodiments set forth herein. These example embodiments are just that—examples—and many implementations and variations are possible that do not require the details provided herein. It should also be emphasized that the disclosure provides details of alternative examples, but such listing of alternatives is not exhaustive. Furthermore, any consistency of detail between various examples should not be interpreted as requiring such detail—it is impracticable to list every possible variation for every feature described herein. The language of the claims should be referenced in determining the requirements of the invention.

In the drawings, the size and relative sizes of layers and regions may be exaggerated for clarity. Like numbers refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

It will be understood that, although the terms first, second, third etc. may be used herein to describe various elements, components, regions, layers and/or sections, these elements, components, regions, layers and/or sections should not be limited by these terms. Unless the context indicates otherwise, these terms are only used to distinguish one element, component, region, layer or section from another element, component, region, layer or section, for example as a naming convention. Thus, a first element, component, region, layer or section discussed below in one section of the specification can be termed a second element, component, region, layer or section in another section of the specification or in the claims without departing from the teachings of the present invention. In addition, in certain cases, even if a term is not described using "first," "second," etc., in the specification, it may still be referred to as "first" or "second" in a claim in order to distinguish different claimed elements from each other.

It will be further understood that the terms "comprises" and/or "comprising," or "includes" and/or "including" when used in this specification, are open-ended and specify the presence of stated features, regions, integers, steps, operations, elements, and/or components, but do not preclude the presence or addition of one or more other features, regions, integers, steps, operations, elements, components, and/or groups thereof.

It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise.

Spatially relative terms, such as "beneath," "below," "lower," "above," "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" as used in a relative sense may encompass both an orientation of above and below in the real world. The device may be otherwise oriented (e.g., rotated 90 degrees or at other orientations) and not affect the relationships described by the spatially relative descriptors.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

I. Feeding Tube Location System and Apparatus

Determining the feeding tube location is important in a number of clinical settings. For all patients who receive a feeding tube, it is critical for the tube to be located in the stomach and not in the lungs. Feeding tubes inadvertently inserted into the trachea or lung airways occurs in 0.3% to 15% of all insertions according to Thomas et al, "Confirmation of nasogastric tube placement by colorimetric indicator detection of carbon dioxide: a preliminary report." J Am Coll Nutr. 1998 April; 17(2):195-7, hereafter "Thomas" which is hereby incorporated in its entirety herein by reference. Inserting a feeding tube into the lungs can cause a number of severe complications, such as lung tissue perforation and pneumonia. Described embodiments are designed to ensure that the feeding tube is appropriately placed in the stomach and not in the trachea, bronchi or lungs.

Proposed embodiments can be used with all types of feeding tubes, including the many different sizes (e.g., in a range of 6 Fr through 18 Fr) and feeding tube forms, which can include, but is not limited to, Levin feeding tubes, Salem Sump style feeding tubes, Dobhoff feeding tubes, Keofeed feeding tubes, small bore feeding tubes, pediatric feeding tubes, and nasojejunal feeding tubes.

A. Determine Tube Location Using Acoustic Sensor

Figure 1B:
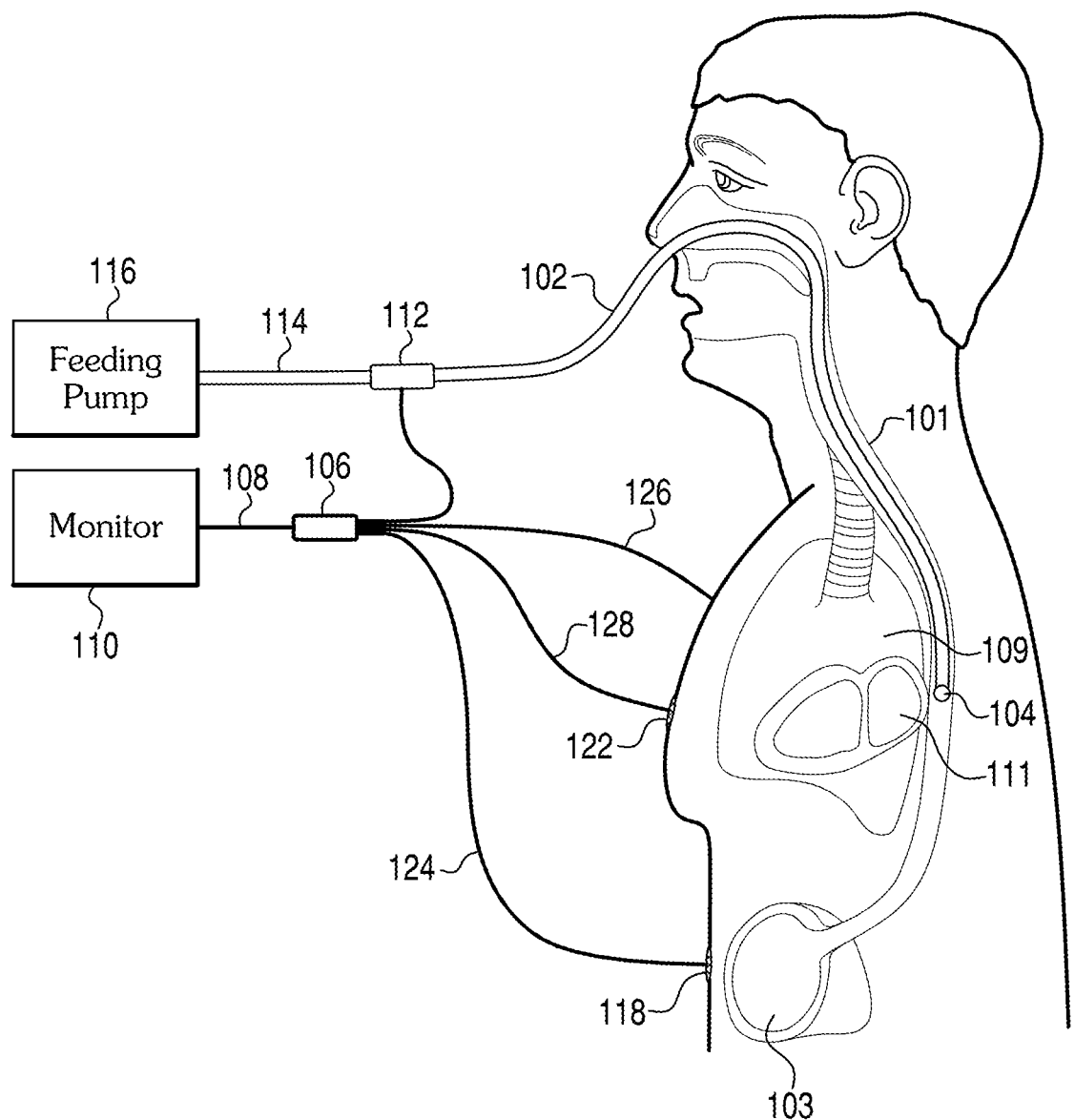
Figure 1C:
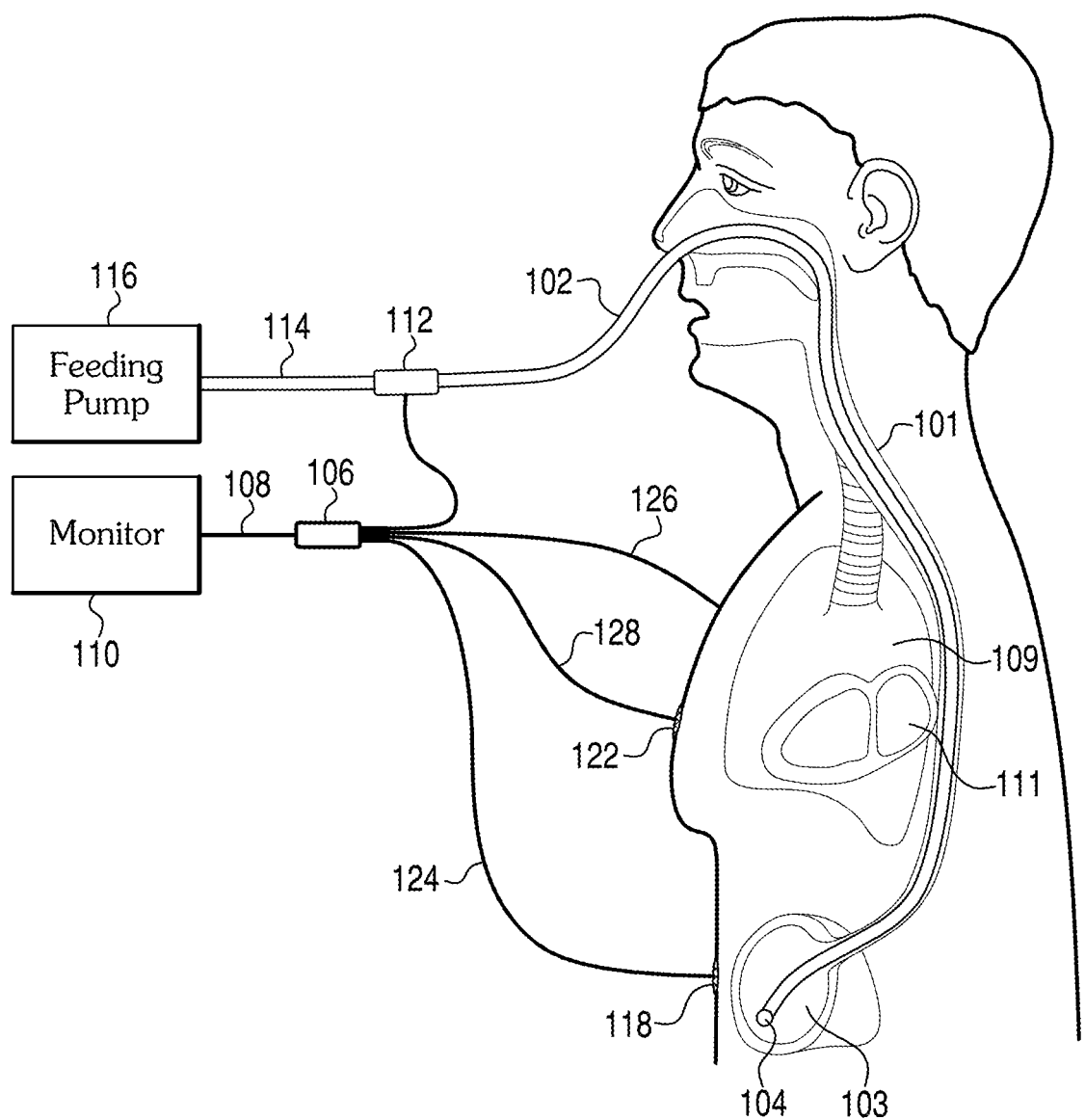

An exemplary embodiment for determining tube location is to use a sensor to measure acoustic signals to determine where the tube is positioned in the body. The acoustic sensor can measure different frequency ranges and types of vibrations including, but not limited to, vibrations associated with the frequency range of audible sounds (20-20,000 Hz). In an exemplary embodiment, a piezoelectric sensor is used to measure the acoustic signals. A number of other exemplary sensors can be used to measure acoustic signals, including but not limited to an electret, condenser, piezoelectric crystal, piezoelectric ceramic, piezoelectric film, fiber optic microphone, or contact accelerometers. FIGS. 1A-1C shows an exemplary apparatus for a feeding tube with an acoustic sensor. In this exemplary embodiment, the patient utilizes a feeding tube 102 to receive enteral nutrition into the stomach 103. The enteral nutrition is administered by a feeding pump 116, which is conveyed via a feeding pump tube 114 and a tube connector 112. This feeding tube 102 contains an acoustic sensor 104. In an exemplary embodiment, this acoustic sensor 104 is located on the distal tip of the tube. The acoustic sensor 104 may be designed to detect certain vibrations, such as audible sounds, non-audible sounds or both audible and non-audible sounds. In an exemplary embodiment, the acoustic sensor 104 is connected via a wire that is located in a second lumen that runs the length of the feeding tube 102. In some examples, the wire is embedded in the wall of the feeding tube 102. In some examples, the acoustic sensor 104 and the wire are connected into a single and separate component that is placed inside the main lumen of the feeding tube 102. This separate component is then removed after the tube insertion is completed by pulling the proximal end of the component. A hydrophilic coating can be applied in the interior of the tube to reduce the friction in the interior and thus make it easier to remove the component. A code or other unique identifier can be integrated into the component and/or feeding tube 102 such that the unique identifier is received by the monitor 110 and validated to ensure the same component and/or feeding tube 102 are not used for multiple patients. Use on multiple patients may not be safe or hygienic. In an exemplary embodiment, the code can be a series of printed alphanumeric characters or machine readable code (numeric and/or text represented by a bar code or in near field communication device) ascribed to the component and/or feeding tube that is entered into the monitor, or controller, 110 for a validation step. In an alternative embodiment, part of the component and/or feeding tube 102 can be disabled upon removal of the component and/or electrical connector 106, making it infeasible to reuse the component and/or feeding tube in multiple patients. In all of the previously described embodiments, a wire can be connected to the electrical connector 106, which is subsequently connected to the monitor 110 via the cable 108. In an alternative embodiment, the sensor can connect to the monitor via a wireless interface, such as Wi-Fi, Bluetooth, cellular, or any other advantageous wireless network. It should be noted that use of the noun "monitor" herein refers to a computer, unless the context indicates otherwise. Such a computer can be configured to track a patient's condition, other data of a patient, medical instruments or equipment used to assist a patient, etc. The monitor can preferably but optionally include a display (e.g., monitor screen) or other indicator (e.g., audible alarm) for a clinician. Although the disclosed embodiments refer to a "monitor," this usage should not be used to limit the invention.

This exemplary apparatus includes a sound emitter 118. The sound emitter 118 is used to generate sounds that are then captured by the acoustic sensor 104. The sound emitter 118 can utilize a piezoelectric transducer or other advantageous mechanisms to generate the desired sounds. "Sound" as used herein refers to any acoustic wave and is not limited to an audible sound. Thus, the emitted sounds of the sound emitter 118 may be audible or non-audible (or both). This sound emitter 118 is connected by the wire 124 to the electrical connector 106. The sound emitter 118 can be designed such that a standard ECG pad can be placed on the end of the sound emitter. Alternatively, the sound emitter 118 can be built into an ECG pad, and thus can be connected to the wire 124 with the modified ECG clip. The sound emitter 118 may be placed close to the stomach. In an exemplary embodiment the sound emitter 118 may be placed on the abdomen just caudal to the left costal margin.

In an exemplary embodiment, this apparatus also includes two electrode sensors. In this exemplary embodiment, the two electrode sensors are used to capture ECG data that can help the process of determining the location of the feeding tube. In this exemplary embodiment, electrode sensors 120-122 are connected to electrical connector 106 by wires 126-128. The electrode sensors are used to record heart patterns and interpret respiratory patterns. To determine heart patterns, the electrodes detect the electrical activity of the heart. When the electrical activity of the heart is displayed on an oscilloscope, a display of the monitor or paper chart, it is called an electrocardiogram (EKG or ECG). The respiratory pattern can be estimated from the ECG signal, hereafter called the ECG respiratory pattern, by detecting the respiratory sinus arrhythmia (RSA), that is the modulation of the R-R interval (i.e., the time between consecutive ECG R-waves) during the respiratory cycle, as described by de Geus et al, "Ambulatory measurement of respiratory sinus arrhythmia and respiration rate." Biological Psychology, vol. 41, no. 3, pp. 205-227, 1995, hereafter "de Geus" which is hereby incorporated in its entirety herein by reference. In an exemplary embodiment where another electrode is added to the apparatus, another option for estimating respiratory patterns from ECG signals is enabled. Specifically, by examining the change of cardiac axis during breathing that manifests itself as a change in QRS amplitude, according to Moody et al, "Derivation of respiratory signals from multilead ECGs," Computers in Cardiology, vol. 12, pp. 113-116, 1985, hereafter "Moody" which is hereby incorporated in its entirety herein by reference. In another exemplary embodiment, the respiratory pattern can be determined through impedance pneumography, In this case, an impedance between two electrodes is measured. The impedance increases with inspiration and decreases with expiration. The electrode sensors 120-122 can be attached to the chest, arms, or other convenient or advantageous locations. In an exemplary embodiment, the sound emitter 118 can also serve the function of an electrode sensor. For example, the same standard ECG pad may have both the sound emitter and ECG conductive electrode mounted thereon. Elements of the sound emitter and ECG conductive electrode may be shared. For example, the ECG conductive electrode may also function as a housing of the sound emitter. This can obviate the need for a second standalone electrode sensor in certain circumstances. For example, utilizing the sound emitter 118 as an electrode sensor can avoid the need for electrode sensor 122.

Figure 3:
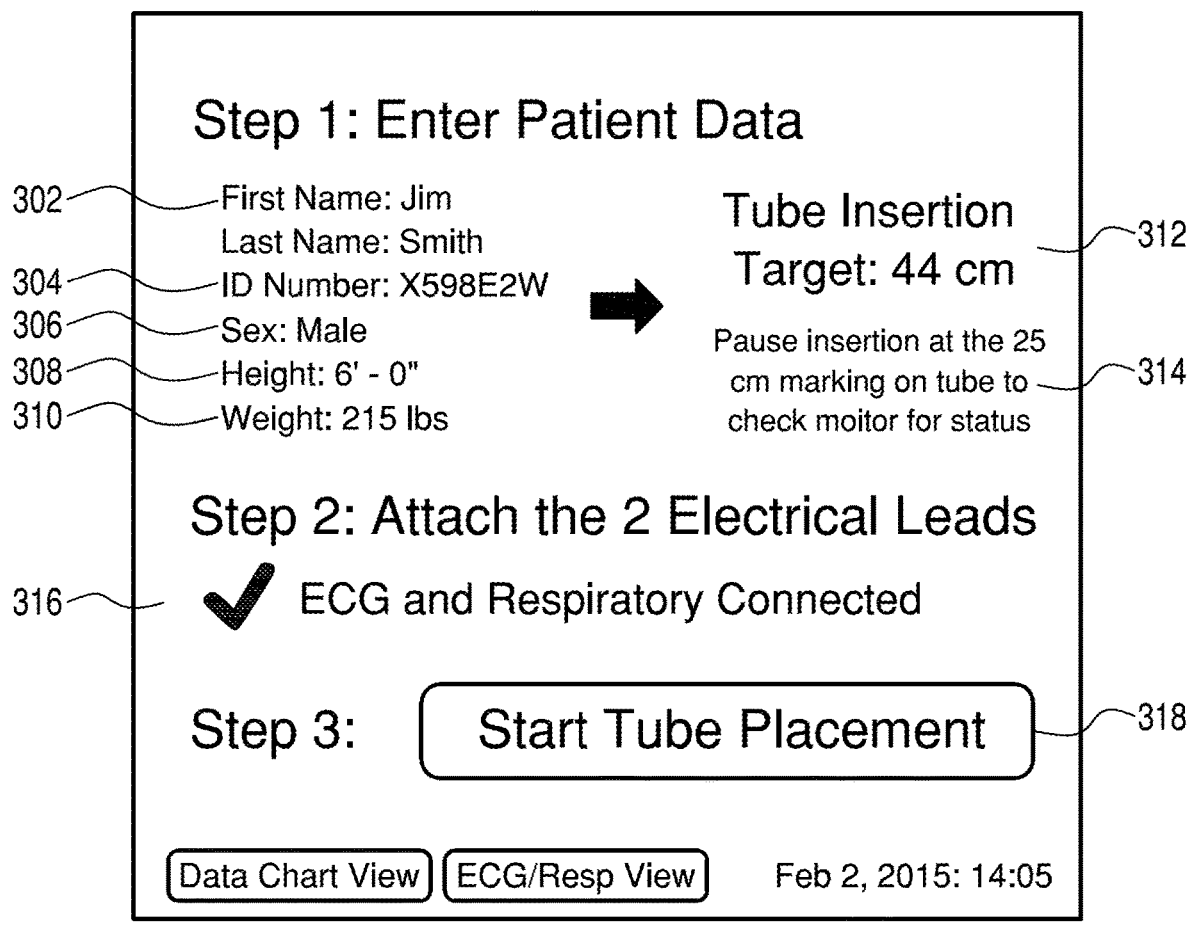
FIG. 3 is a schematic of a user interface screen of the exemplary monitor of FIG. 1.

An exemplary process for utilizing the apparatus described in FIGS. 1A-1C is provided in FIG. 2. In the first step of this exemplary process 201, the clinician enters patient data into the monitor (also referred to herein as a controller) as shown in an exemplary depiction of a monitor screen shown in FIG. 3. Patient data, such as name 302, ID number 304, sex 306, height 308 and weight 310, can be entered into the monitor manually or through an electronic data interchange. Optionally, the clinician can measure the distance between the nose, ear, and the umbilicus and enter the same into the monitor. In step 202, the monitor, based on this patient data, calculates and displays a target distance 312 for inserting the tube. This target distance indicates the length the tube should be inserted into the patient (e.g., a distance measured from the patient's front teeth, lips or nose) and can be visually verified by reference to measurement markings on the tube. The algorithm for calculating the target measurement can be based on nomogram data as described by Cirgin Ellett et al, "Predicting the Insertion Distance for Placing Gastric Tubes." *Clin Nurs Res* 2005 February; 14(1):11-27, hereafter "Cirgin Ellett" which is hereby incorporated in its entirety herein by reference. The nomogram can be used to identify an appropriate target depth for tube insertion that is determined to correspond with correct placement of the end of the tube in the stomach of the patient.

An insertion message 314 is presented instructing the clinician to pause the insertion once the tube has been inserted into the patient an intermediate distance (e.g., to a point where a specific distance marking on the tube is about to pass into the nose or mouth). In example, this intermediate distance has been calculated as 25 cm. This intermediate distance can be determined by the computer as a function of the identified target depth for tube insertion (e.g., a ratio of the identified target depth or by referencing a look-up table pairing a range of tube insertion depths to corresponding intermediate distances). This distance marking signifies the point where the clinician should pause the insertion to monitor for one or more signals consistent with the tube being correctly inserted or consistent with the tube being incorrectly inserted. The signals can be generated by the patient, such as the sound of a heartbeat or the sound of breathing. In this example, the clinician can check the monitor to make sure that the tube is not in an inappropriate part of the airway, such as in the lower respiratory tract (i.e., past the glottis opening, or past the vocal folds, in the larynx, in the trachea or in the bronchi) and/or that auscultated heart pattern is consistent with correct position. Data that indicate that the tube is correctly positioned in the esophagus might include one or more of: 1) failure to detect the characteristic sounds of air moving in the lower respiratory tract, such as in the larynx, trachea and/or bronchi ("auscultated lower respiratory tract pattern"); 2) detection of the sounds made by the beating heart ("auscultated heart pattern") within a range of appropriate intensities; 3) calculation of an appropriate distance between the acoustic sensor and sound emitter.

In step 203, the clinician attaches the two electrodes 118, 120 to the body, with 118 being ideally placed on the abdomen just caudal to the left costal margin and 120 being placed in an accessible location such as the shoulder. After attaching the two electrodes, the monitor will show a message 316, if heart and respiration signals are being correctly received and processed. Next, the clinician can proceed to step three and press a button 318 at the start of tube placement, thus initiating the capturing and analyzing acoustic signals by the monitor. In this example, the monitor continually analyzes these acoustic signals to detect three separate patterns, specifically the auscultated lower respiratory tract pattern that is associated with being located in the larynx, trachea and/or bronchi, the auscultated heart pattern, and the sound pattern from the sound emitter.

In step 204, the clinician begins to insert the feeding tube 102 into the patient. As the feeding tube 102 is inserted, it is possible for the tube to enter the trachea 107, as shown in FIG. 1a. As the tube is being inserted, the acoustic sensor 104 is capturing acoustic signals and sending this data back to the monitor 110.

In step 205, the monitor 110 analyzes these acoustic signals to determine if the signals indicate an auscultated lower respiratory tract pattern that is typically recorded when the acoustic sensor is located in the larynx, trachea 107 or a bronchus 109. The frequency of normal lung sounds auscultated from outside of the body are in the range of 50 to 2500 Hz according to Reichert et al, "Analysis of Respiratory Sounds: State of the Art." Clin Med Circ Respirat Pulm Med. 2008 May 16; 2:45-58, hereafter "Reichert" which is hereby incorporated in its entirety herein by reference. Reichert also describes how tracheal sounds can reach up to 4000 Hz. There are number of advantageous algorithms and analysis techniques to determine if the acoustic signals indicate auscultated lower respiratory tract patterns, including but not limited to Fourier transform, wave-form, wavelet, and neural networks according to Earis et al, "Current methods used for computerized respiratory sound analysis." Eur Respir Rev 2000; 10: 77, 586-590, hereafter "Earis" which is hereby incorporated in its entirety herein by reference. A Fourier transform approach to detecting and analyzing respiratory sounds is described in Charbonneau et al, "Basic techniques for respiratory sound analysis." Eur Respir Rev 2000; 10: 77, 625-635, hereafter "Charbonneau" which is hereby incorporated in its entirety herein by reference. In step 205, the monitor also analyzes the ECG signals to determine an ECG respiratory pattern, which can be accomplished via the previously described exemplary approaches of detecting the RSA or changes in QRS amplitude.

In an exemplary embodiment the monitor may perform an analysis to match the initially detected auscultated respiratory pattern with the ECG respiratory pattern that is derived from the electrodes, as shown in step 206. In an exemplary embodiment, this comparison can provide additional information that can help ensure that an auscultated respiratory pattern has been detected in the sound detected by the acoustic sensor. There are a number of exemplary approaches to determine if there is a match between the auscultated and ECG respiratory patterns. In an exemplary embodiment, the monitor performs an analysis to match the key or identifiable points in the auscultated respiration pattern with the key or identifiable points in the ECG respiration pattern. These key or identifiable points can be derived from specific aspects of inhalation and exhalation related to respiration and the timing of such key or identifiable points. For example, a key or identifiable point can be the timing of the peak of the auscultated lower respiratory tract pattern and the timing of the peak of the ECG respiration pattern. Similarly, the timing of the trough of the auscultated respiration pattern and the timing of the trough of the ECG respiration pattern can be used as a key or identifiable point. In an exemplary embodiment, one respiration pattern can be used as a starting point to determine if the other respiration pattern is a match. For example, by continually measuring the ECG respiration pattern, it is possible to generate a baseline of key or identifiable points of the respiration pattern and then analyze the auscultated respiration pattern to determine the corresponding existence of these key or identifiable points, or to analyze just these key or identifiable points to determine if there is a match or correlation of sufficient magnitude. This pattern matching can include one or more of data smoothing, time series analysis, cross-correlation analysis, convolution analysis, regression analysis, and neural networks. Matching the two patterns can be advantageous, since the auscultated respiration pattern is more likely to be a valid respiration pattern indicative of being located in the larynx, trachea or bronchi when the auscultated respiration pattern matches the continually measured ECG respiration pattern derived from the ECG signal. If the two patterns (i.e., the ECG respiratory pattern and the auscultated respiratory pattern) match or correlate to a sufficient degree, then it is highly likely that the acoustic sensor is located in the lower respiratory tract, such as the larynx, trachea or a bronchus.

The results of this respiratory pattern analysis are presented on the monitor as shown in step 207. If the results are negative, the monitor displays the message that the feeding tube is not located in the trachea or a bronchus. If an auscultated lower respiratory tract pattern is detected (e.g., a match or significant correlation with the ECG respiratory pattern is detected), the monitor can indicate a visual alarm, and/or an auditory alarm, to warn the clinician that the tube may be located within the lower respiratory tract, such as the larynx, trachea or a bronchus. The clinician can then stop tube insertion and withdraw the tube.

In step 208, the acoustic sensor detects the auscultated heart pattern as the feeding tube is being inserted. The auscultated heart pattern can be detected immediately upon tube insertion in the body since the heart can emit a strong signal, i.e., a signal that is loud and can travel significant distances within the body. The spectrum for capturing the auscultated heart pattern is generally defined as between 20 and 100 Hz according to Reichart. There are a number of advantageous means to analyze heart sounds to determine the auscultated heart pattern including but not limited to Fourier transform and wavelet transform according to Debbal et al, "Computerized heart sounds analysis." Comput Biol Med. 2008 February; 38(2):263-80. Epub 207 November 26, hereafter "Debbal" which is hereby incorporated in its entirety herein by reference.

If the monitor detects an auscultated heart pattern, in an exemplary embodiment the monitor will then perform an analysis to match the auscultated heart pattern with the ECG heart pattern that is derived from the electrodes, as shown in step 209. In this exemplary embodiment, this comparison can provide additional information that can help ensure that an auscultated heart pattern has been detected. A number of processing steps can be required to perform this pattern matching, including but not limited to data smoothing, time series analysis, cross-correlation analysis, convolution analysis, regression analysis, and neural networks. Matching the two patterns is advantageous, since the detected heart sound pattern is more likely to be an actual heart sound pattern when the pattern matches the continually measured and well-known ECG-based heart pattern derived from the electrodes. Matching these two patterns therefore increases the confidence that the acoustic sensor is correctly detecting the heart pattern.

As shown in FIG. 1b, as the clinician inserts the feeding tube 102 down the esophagus 101, the acoustic sensor 104 moves within close proximity of the heart 111. The monitor 110 is continually measuring the intensity of the heart sound as the feeding tube 102 transits the length of the esophagus 101 as it moves toward the stomach 103. As the feeding tube 102 gets closer to the heart 111 during this transit, the heart sound should increase in intensity, or amplitude. Conversely, as the feeding tube 102 moves past the heart 111 and gets close to entering the stomach 103, the heart sound should decrease in intensity, or amplitude. This increasing and decreasing intensity in the measured auscultated heart pattern can be analyzed to determine an approximate location of the feeding tube, e.g., a location of the feeding tube's relative to the heart of the patient. The measurement of the auscultated heart pattern will be analyzed over time to determine if it matches a similar increasing and decreasing pattern of intensity, as shown in step 210. A number of processing steps can be required to perform this pattern matching, including but not limited to data smoothing, time series analysis, cross-correlation analysis, convolution analysis, regression analysis, and neural networks. For example, the maximum amplitude of the auscultated heart pattern can be identified and plotted versus time. These points can then be analyzed to confirm a substantially continuous rise of the amplitudes to the maximum amplitude and/or confirm a substantially continuous decline from the maximum amplitude. In step 211, the results of this analysis are shown on the monitor, such as a message describing the status of the analysis and a chart showing the intensity of the auscultated heart pattern over time.

In step 212, the monitor analyzes the acoustic signals coming from the sound emitter 118 and captured by the acoustic sensor 104, and calculates the distance between the sound emitter and acoustic sensor. The acoustic signal can take many exemplary forms, including but not limited to a sound pulse, a continuous variable tone and can be emitted at different audible, ultrasound, or other advantageous frequencies. By knowing the precise timing of initiating the acoustic signal from the sound emitter and the timing of receiving the signal by the acoustic sensor, the monitor can perform calculations to determine the distance between the sound emitter and the acoustic sensor. For example, when a pulse is emitted at time t1 by the sound emitter 118 and received at time t2 by the acoustic sensor 104, in an exemplary embodiment, the distance x can be calculated as $x=(t1-t2) \times v$, where v=the speed of sound through the patient (v can be determined through calibration, i.e., tested on the patient from known distances, or determined from empirical data). This process therefore provides the distance between the acoustic sensor 104 and the sound emitter 118. In step 213, the monitor displays the status of the distance calculation and a chart showing these distance calculations over time. In some embodiments, the monitor may display a distance that is derived from the distance between the acoustic sensor 104 and the sound emitter 118 (e.g., a distance remaining to complete insertion of the feeding tube).

In an exemplary embodiment, the clinician pauses the insertion to check the monitor after inserting the tube approximately halfway into the patient, such as in FIG. 1b. The purpose of checking the monitor is to determine if any of the summary data would indicate the tube is located in the trachea or bronchi, or if the tube appears to be located correctly in the esophagus, as shown step 214. In this example, the clinician pauses the insertion based on tube markings close to the point of entry, such as the nose or mouth, indicating the tube had been inserted 25 cm. Other exemplary markings and insertion distances may apply, such as those having a dependence on or calculated based upon the identified target depth or otherwise calculated as a function of the data of the patient (such as size, age, sex, etc.). The clinician can check the monitor to see if there is any indication the tube tip is located in the larynx, trachea or bronchi. The clinician can also check the monitor to see if the auscultated heart pattern has increased in intensity, which would be an indication that tube has progressed down the esophagus and is near the heart. The combination of no indicated auscultated lower respiratory tract pattern along with an increase in intensity of an auscultated heart pattern indicates that the tube is progressing correctly down the esophagus towards the stomach. The clinician can also check the monitor to see if the calculated distance between the acoustic sensor and the sound emitter has decreased during the period of insertion. This decreasing distance indicates that tube has progressed down the esophagus, and conversely has not become coiled in the mouth, nasopharynx or hypopharynx. The combination of no auscultated lower respiratory tract pattern, an increase in intensity of an auscultated heart pattern, and decreasing distance between the acoustic sensor and the sound emitter provide a strong indication that the tube is progressing correctly down the esophagus towards the stomach. Any combination of an indication of an auscultated lower respiratory tract pattern, an indication that the auscultated heart pattern intensity has not increased with insertion of the tube, and no evidence of decreasing distance between the acoustic sensor and the sound emitter, may indicate the tube is not progressing correctly down the esophagus towards the stomach and may be in the trachea or bronchi or has become coiled. After reviewing these data, the clinician can then decide whether to proceed with the tube insertion or take other action, such as removing and reinserting the feeding tube or taking an X-ray to confirm the placement of the tube.

In FIG. 1c, the acoustic sensor 104 is shown in the stomach 103 and located more closely to the sound emitter 118. After the clinician has inserted the tube 102 to the recommended insertion distance, the clinician can check the monitor to see the distance between the sound emitter 118 and the acoustic sensor 104. The clinician can then compare this calculated distance with a visual identification of seeing where the sound emitter 118 is physically placed on the patient and making an assessment as to whether the distance corresponds with the feeding tube 102 being correctly placed in the stomach 103 and conversely not in the trachea or bronchi 109. As the feeding tube 102 progresses toward and into the stomach 103, the calculated distance between the sound emitter 118 and acoustics sensor 104 should decrease.

In step 215, the clinician reviews the summary information and inputs the distance marking on the tube into the monitor. This distance marking corresponds with the furthest point the tube has been inserted into the patient. The monitor then compares the inputted tube distance with the recommend insertion distance calculated in step 202. If the difference between the two insertion distances is above a defined threshold, the monitor will display a message that the tube insertion distance may not be sufficient for proper location in the stomach. If the difference between the two insertion distances is below a defined threshold, the monitor will display a message that the tube insertion distance is sufficient. In an exemplary embodiment, the threshold for the difference in tube distance is 5 cm; in another embodiment, the threshold for the difference is 10% of the identified target depth.

Figure 4:
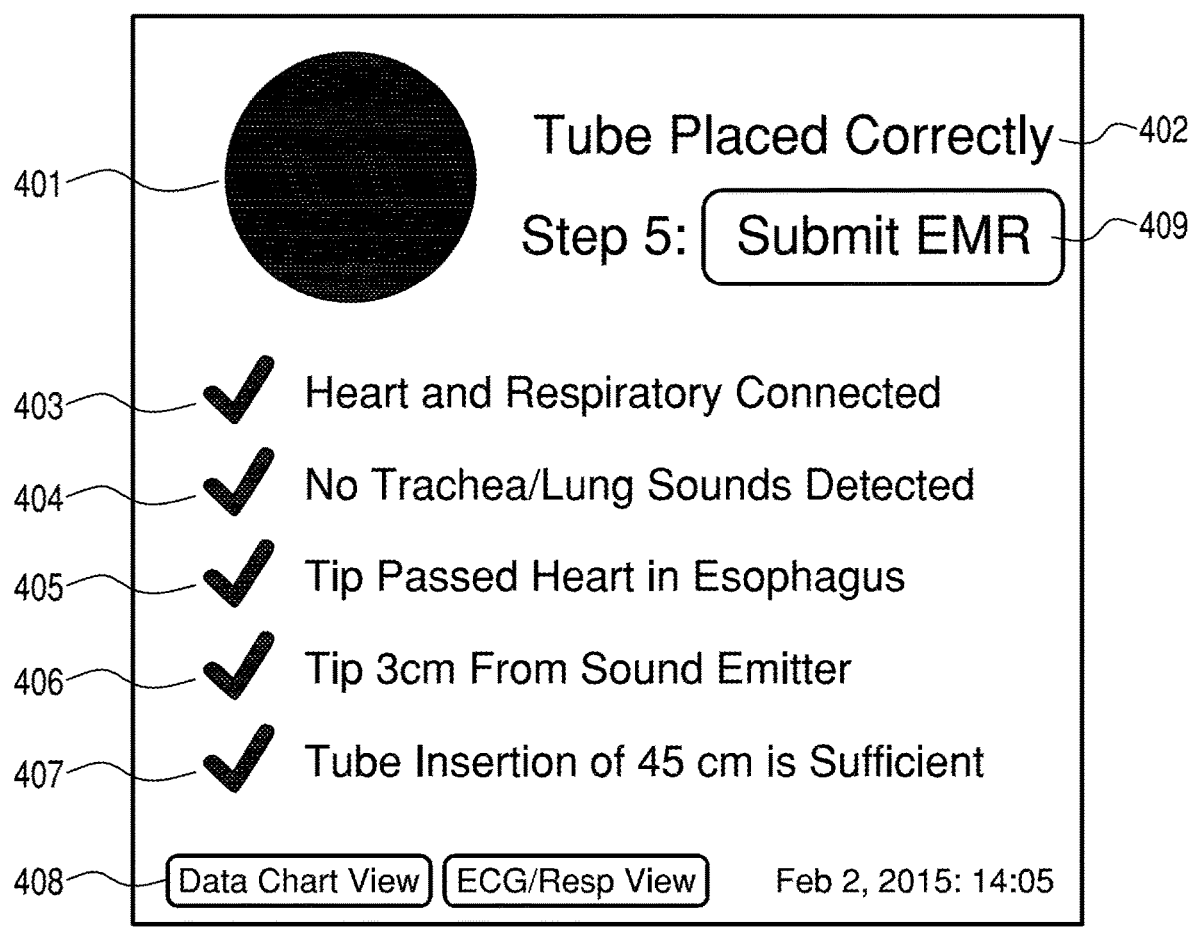
FIG. 4 is schematic of user interface screen of the exemplary monitor of FIG. 1.

FIG. 4 depicts an example monitor screen where all assessments have indicated that the tube is placed correctly in the stomach. The most visible indication on the screen is the status indicator 401, which displays the color green to signify the tube is placed correctly. If the monitor algorithm calculations result in an indication that the tube is not placed correctly, or if there is not enough information to determine if the tube is placed correctly, the status indicator 401 displays the color yellow. If the monitor algorithm calculations result in an indication that the tube is placed in the trachea or a bronchus, the status indicator 401 displays the color red. In addition, a text status indicator 402 conveys the status of the tube placement. In the scenario for FIG. 4, the text status indicator indicates the "Tube Placed Correctly". The heart and respiratory signal indicator 403 displays a message, "Heart and Respiratory Connected", signaling that the heart and respiratory signals from the electrodes are being correctly captured. The trachea and lung sounds signal indicator 404, displays a message, "No Trachea/Lung Sounds Detected", signaling that the acoustic sensor and monitor are currently not detecting any trachea or lung sounds, and thus indicating the feeding tube tip is not in the trachea or bronchus. The heart transit indicator 405, displays a message, "Tip Passed Heart in Esophagus", signaling that the acoustic sensor and monitor detected the pattern of the tube tip passing by the heart during transit down the esophagus. The indication of the tube tip passing by the heart during transit down the esophagus is further confirmation that the tube tip is not located in the trachea or bronchus. The sound emitter distance indicator 406, displays a message, "Tip 3 Cm from Sound Emitter", signaling the acoustic sensor is located 3 cm from the sound emitter. The indication that the acoustic sensor is located a short distance from the sound emitter, which should be located caudal to the left costal margin, is further confirmation that the tube tip is located in the stomach, and conversely is not located in the trachea or bronchus. The tube insertion indicator 407 displays a message, "Tube Insertion of 45 cm Is Sufficient", signaling that the inputted tube insertion distance is sufficient for the tube to be placed correctly in the stomach. If the clinician is satisfied that the data presented on the monitor is sufficient to confirm the tube is correctly placed in the stomach, the clinician can then submit the electronic medical record by pressing button 409.

Figure 5:
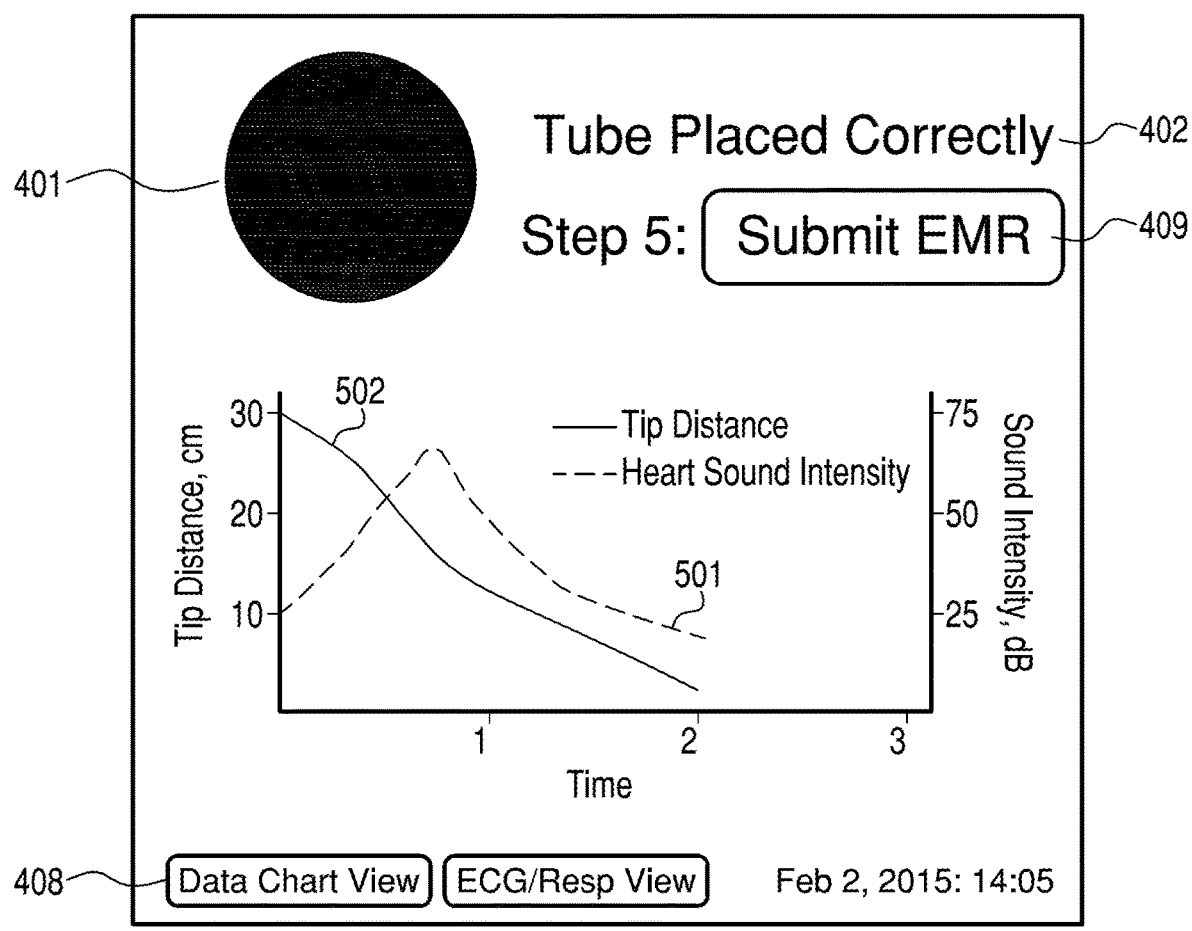
FIG. 5 is schematic of user interface screen of the exemplary monitor of FIG. 1.

The clinician also has the option to review more detailed data on the monitor. By pressing the Data Chart View button 408, the clinician can view more detailed information in chart form. FIG. 5 shows this optional view to review the data in chart form. For example, the clinician can review the Heart Sound Intensity chart 501 to see a time-based view of the heart sound intensity data. If the feeding tube transited the esophagus correctly, this would be indicated by an increase in auscultated heart pattern intensity as the tube tip gets closer to the heart and a decrease in intensity as it passes the heart on the way towards the stomach. The clinician can also view feeding tube tip distance 502 over time (e.g., graphically), which should generally indicate a decrease in tube tip distance from the sound emitter as the tube is being inserted. Alternatively, the clinician may review the heart sound intensity with respect to the measured feeding tube tip distance. In this example, the measured feeding tube tip distance may be plotted along the x-axis and the heart sound intensity may be plotted along the y-axis. The clinician may repetitively sample the heart sound intensity at the same distances by inserting and retracting the feeding tube.

After the tube has been inserted, the clinician can still refer to the monitor to see an update of the distance between the acoustic sensor and the sound emitter. This may be valuable to determine if the tube has moved during treatment and if the tube insertion may need to be adjusted.

In an exemplary embodiment, the clinician can utilize the same monitor for multiple patients. In this embodiment, the monitor associates a unique ID with each feeding tube. If the feeding tube was disconnected from the monitor and subsequently reconnected, the monitor can utilize the unique ID of the feeding tube to associate all previously entered and measured data from that feeding. Therefore, a clinician can utilize one monitor to insert feeding tubes into multiple patients, and as necessary reconnect the monitor to a tube to assess the location of the tube without having to reenter any patient data. A history of patient data is stored such that any previously entered patient data can also be accessed and associated with any new feeding tubes.

Figure 6:
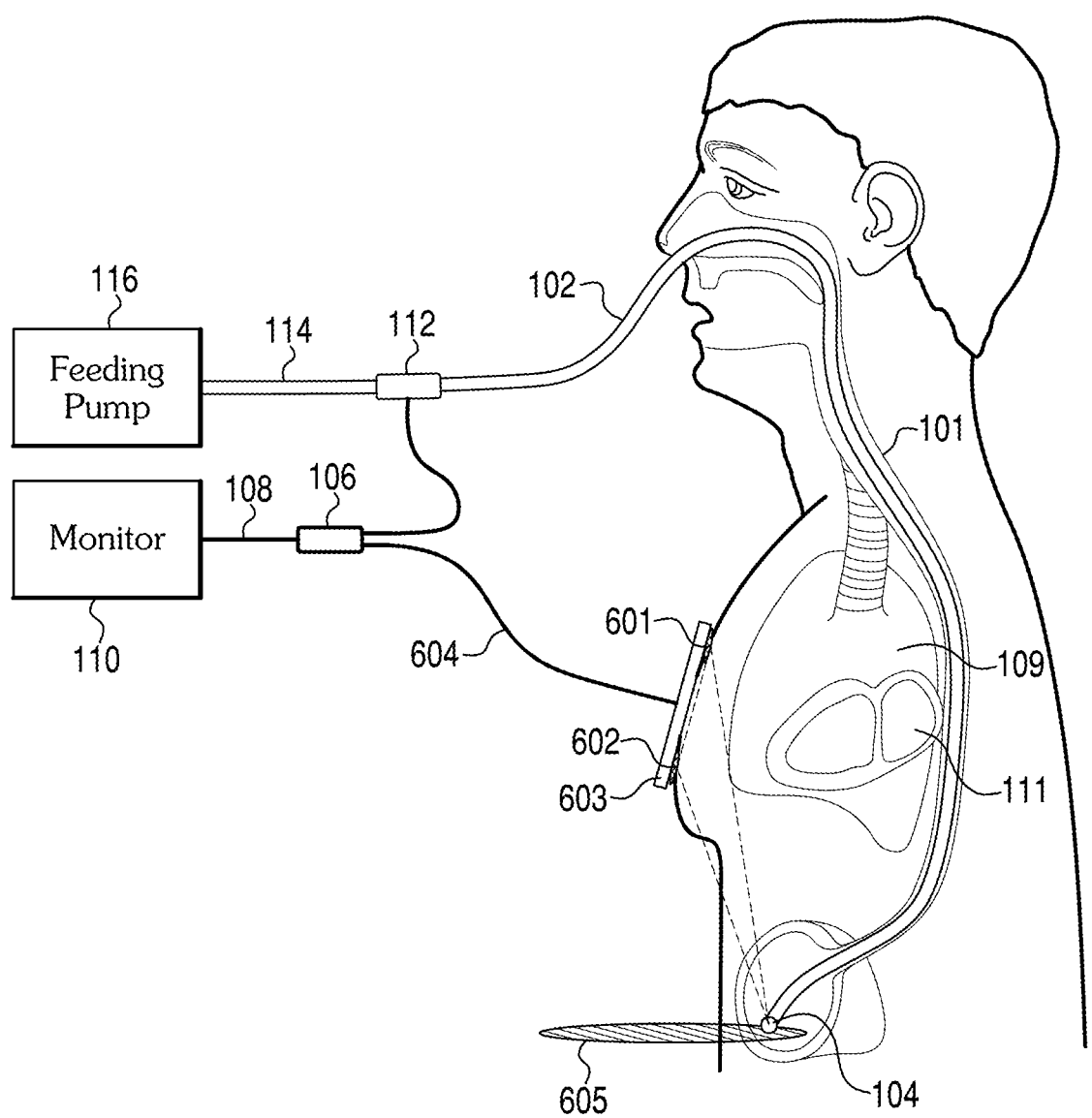
FIG. 6 is a schematic of an apparatus for placing a feeding tube in accordance with another exemplary embodiment.

FIG. 6 shows an alternative embodiment of the apparatus to determine feeding tube location. In this exemplary embodiment, two sound emitters 601 and 602 are used to determine the distance from the acoustic sensor 104 to the sound emitters. The sound emitters 601 and 602 are connected to a rigid member 603. The rigid member 603 is connected via wire 604 to electrical connector 106. The two sound emitters 601 and 602 also serve as electrodes to capture heart and respiratory signals. The distance between the acoustic sensor 104 and the sound emitters 601 and 602 that can be calculated in the same fashion as described elsewhere herein. Therefore, in each instance in time, the distance between acoustic sensor 104 and sound emitter 601 is known and the distance between acoustic sensor 104 and sound emitter 602 is known. Additionally, the distance between sound emitter 601 and sound emitter 602 is known given their fixed location on the rigid member 603. These three distances form a triangle, so knowing the lengths of each side of the triangle makes it possible to calculate the angles of this triangle and thus determine the location of the acoustic sensor. With one sound emitter (e.g., just one of 601 and 602), you can determine the location of the acoustic sensor as being a certain distance away from the one acoustic sensor (e.g., determined to be on a point of the surface of an imaginary three-dimensional sphere having the location of the one acoustic sensor as its center). In this exemplary embodiment with two sound emitters, you can determine the location of the acoustic sensor as being on a point of the circumference of an imaginary two-dimensional circle 605. This level of accuracy in determining the location of the acoustic sensor 104 may be advantageous. For example, when the two sound emitters 601 and 602 are arranged vertically, the imaginary circle on which the acoustic sensor 104 is determined to lie will be horizontal. Thus, a vertical location of the acoustic sensor 104 can be accurately determined even if its horizontal location has been determined via this calculation to be on the horizontal imaginary circle. Using three sound emitters (not shown in FIG. 6) that are arranged in a triangle and spaced apart known distances (i.e., not linearly arranged) allows for further precision in determining the location of the acoustic sensor. Triangulation can be used to calculate a point in space relative to the location of the three sound emitters. For example, for each of the three sound emitters, a sphere with the corresponding sound emitter as its center can be determined, with the radius of the sphere representing the determined distance between the sound emitter and the acoustic sensor and the surface of the sphere representing a possible location of the acoustic sensor. The intersection of these three determined spheres can be determined as the location of the acoustic sensor. Another approach is to use each pair of the three sound emitters to calculate possible locations along a corresponding imaginary circle. The intersection of these three imaginary circles will correspond to a determined location of the acoustic sensor 104.

Figure 7:
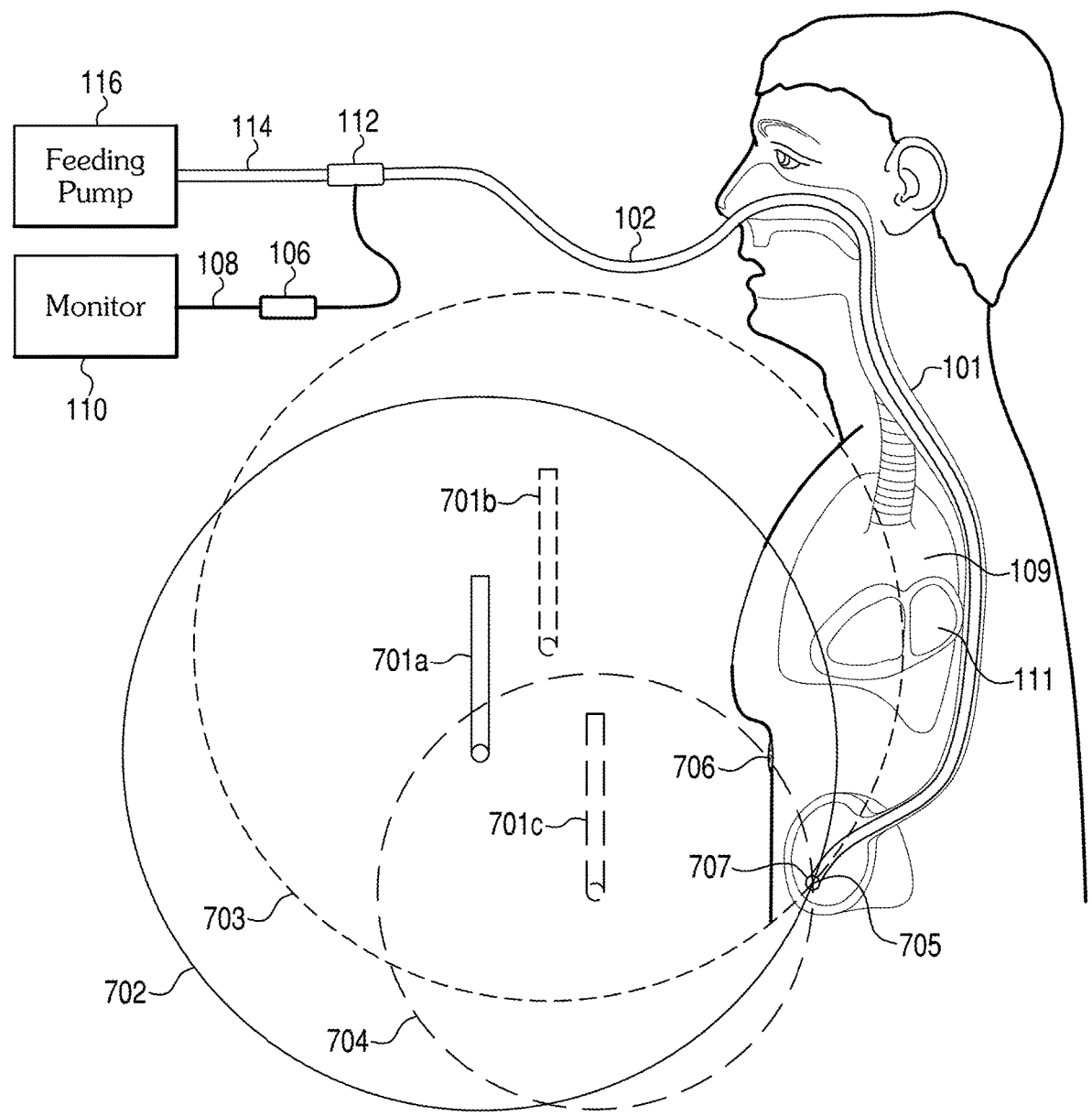
FIG. 7 is a schematic of an apparatus for placing a feeding tube in accordance with another exemplary embodiment.

FIG. 7 shows an alternative embodiment of the apparatus to determine feeding tube location. In this exemplary embodiment, the apparatus utilizes a mobile device 701 (shown as 701a, 701b and 701c at respective different locations). This mobile device 701 can take the form of a mobile phone, tablet, or other advantageous mobile device. In this embodiment, the mobile device 701 uses a wireless connection to communicate with the monitor 110. A tip component 707 is located in the tip of the feeding tube and, in this embodiment, is used to sense the acoustic signals from the mobile device 701. In an exemplary embodiment, the mobile device 701 continuously emits a acoustic signal. In this embodiment, the tip component 707 is the acoustic sensor 104. The signal received by the tip component 707 is used by the monitor 110 to calculate the distance between the tip component 707 and the mobile device 701.

An exemplary process is to move the mobile device 701 while the tip component 707 receives the sound signals. In a first position, mobile device 701a is a calculated first distance from tip component 707 where the distance can be visualized as the radius of a first sphere 702 (with mobile device 701a at the center) and the location of the tip component 707 is somewhere on the surface of that first sphere 702. In a second position, mobile device 701b is a calculated second distance from tip component 707 where the distance can be visualized as the radius of a second sphere 703 (with mobile device 701b at the center) and the location of the tip component 707 is somewhere on the surface of that second sphere 703. In a third position, mobile device 701c is a calculated third distance from tip component 707 where the distance can be visualized as the radius of a third sphere 704 (with mobile device 701c at the center) and the location of the tip component 707 is somewhere on the surface of that third sphere 704. If you assume the acoustic sensor is not moving between the three positions then the intersection point 705 where each of the three spheres intersects is the location of the tip component 707 in three-dimensional space. Determining location via this process is called trilateration, as described by Wikipedia, "Trilateration". Wikipedia. Web. 3 Mar. 2015. Web. <http://en.wikipedia.org/wiki/Trilateration>. To determine this intersection point 705, you need to first determine the location of the mobile device 701 in each position relative to the other positions.

In an exemplary embodiment, the location of each position relative to the other positions can be determined by utilizing an accelerometer and gyroscope contained in the mobile device 701. The accelerometer and gyroscope can enable calculating the position, orientation and velocity of the mobile device and thus enable determining a relative location at each time interval. In an exemplary embodiment, the mobile device emits sound signals at 20 Hz, or 20 times per second, and therefore continually calculates relative location 20 times per second. Other exemplary frequencies for emitting a sound signal and calculating relative location can be used.

In an exemplary embodiment, the accuracy of determining the relative location of the mobile device 701 can be enhanced by using an additional reference point. In an exemplary embodiment, a known visual reference 706 can be utilized. In this embodiment, a camera contained in the mobile device 701 can be utilized to view the visual reference 706. An exemplary form for this visual reference 706 can be a two dimensional rectangle with a length of 2 cm on one side and 4 cm on the other side attached to the body of the patient. Another exemplary form for this visual reference 706 can be a high contrast, two dimensional marker of known dimensions which lacks reflection symmetry and/or rotation symmetry attached to the body of the patient. Other forms and dimensions can be used. Since the form and dimensions are known, algorithms in the sound emitter 701 can analyze data from the camera to calculate the distance from the visual reference 706 to the mobile device 701 based on the characteristics of the visual reference 706, such as calculated diameter of the disk compared to the known diameter and the shape of the disk compared to the known shape.

In an exemplary embodiment, the relative position of tip component 707 can be communicated to the clinician via an augmented reality interface on a screen contained in the mobile device 701. Augmented reality is defined as viewing data in what appears to be a camera field of view. In this embodiment, the clinician can look at the screen of the mobile device 701 and see what appears to be a real-time video feed of the patient. The clinician can first wave the mobile device 701 forward, then backward, and from side to side over the patient to calculate a relative location of the tip component 707. The clinician can then see on the screen of the mobile device 701 a representation of the tip component 707 on the screen relative to its position within the patient's body. The visual representation of the patient's body on the screen can exhibit a transparency effect to create the illusion that you can see the tip component 707 within the patient's body. An exemplary embodiment of this transparency effect can be within the sight line of the tip component 707, the patient's body has an algorithm generated surface appearance that makes it look as if you're looking beneath the surface of the patient's body. The clinician should therefore be able to see the location of the tip component 707 relative to the patient's anatomy and determine if the tip component 707 is correctly placed in the stomach, and conversely is not placed in the trachea or bronchus. In an exemplary embodiment, an algorithm-generated appearance can also simulate a visual representation of organs such as the stomach, lungs and heart to assist the clinician and determining the location of the acoustic sensor.

B. Determine Tube Location Using Magnetic Field Sensor

In an exemplary embodiment, an alternative (or additional) apparatus can be used in a similar process previously described for the mobile device 701 and the tip component 707. This alternative (or additional) apparatus comprises a magnetic field sensor, or magnetometer, contained within the mobile device 701. The magnetometer can measure the strength of the magnetic field that is around the mobile device 701. In an exemplary embodiment, the tip component 707 can contain magnetic material with a known magnetic moment. In an alternative embodiment, the tip component 707 consists of coiled wiring that upon application of a known electric signal creates a known magnetic moment. In an exemplary embodiment, the clinician can also wave the mobile device 701 forward, then backward, and from side to side over the patient. Instead of measuring distance between the mobile device 701 and the tip component 707 based on the elapsed time for the sound signal to travel between them, the distance is instead calculated based on the strength of the magnetic field measured from the magnetic material in the tip component 707. The measurement of distance (measured in meters) from the mobile device 701 in the tip component 707 can be calculated using the following exemplary formula:

$$d = \sqrt[3]{\frac{\mu_0}{4\pi}\frac{2\mu}{B}}$$

In this formula $\mu_0$ represents the permeability constant ($4\pi \times 10^{-7}$ T m/A), $\mu$ is the magnetic moment of the magnetic material in the tip component 707, and B is the magnetic field (measured in tesla). The clinician can similarly be able to view an augmented reality visual representation of the tip component 707 relative to the patient's body on the screen of the mobile device 701. In an exemplary embodiment, the accuracy of determining the relative location of the mobile device 701 can also be enhanced by using a known visual reference 706, as previously described.

II. Motility Measurement System and Apparatus

Figure 8:
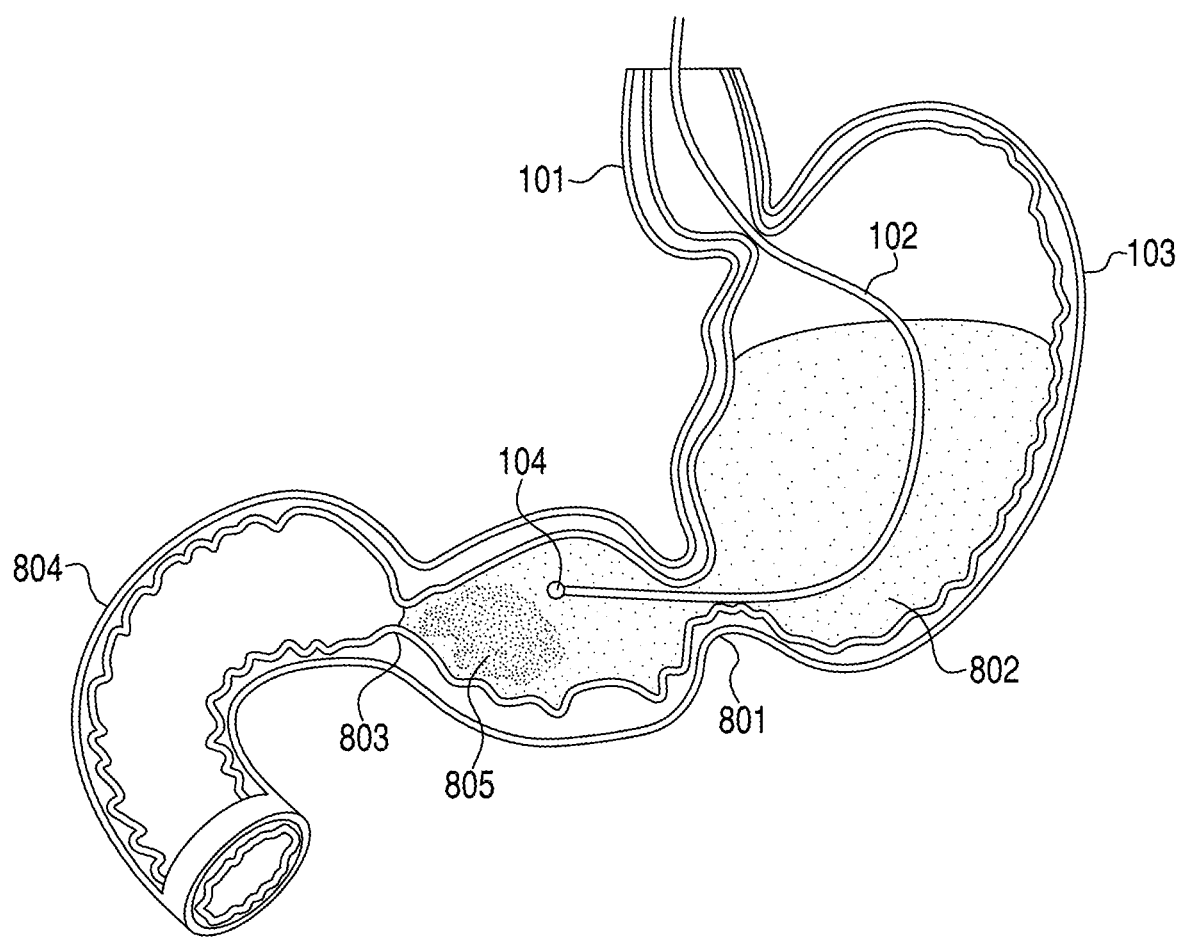
FIG. 8 is a schematic of an apparatus for assessing gastric motility in accordance with an exemplary embodiment.

Determining if the patient is tolerating enteral nutrition is critically important in delivering effective care and avoiding devastating complications. Determining whether the patient has satisfactory gastric motility can indicate if enteral nutrition will be tolerated. Normal gastric motility can be defined as periodic or occasional peristaltic movements of the stomach that propel the contents of the stomach into the small intestine. FIG. 8 shows an example of this peristaltic movement. In FIG. 8, a peristaltic wave 801 is shown moving through the stomach 103. These peristaltic waves 801 move the food through the stomach 103 and out through the pyloric sphincter 803 into the duodenum 804 according to Ehrlein et al, "Gastrointestinal Motility." Class Tutorial, Technische Universitat Munchen, 2014, hereafter "Ehrlein" which is hereby incorporated in its entirety herein by reference. During the movement of a peristaltic wave 801, muscles in the stomach 103 contract to push food 802 from the proximal stomach 103 towards the pylorus 803 at the distal end of the stomach. In addition to peristaltic waves 801, the stomach 103 moves food 802 towards the pylorus 803 by generally contracting and thus shrinking the size of the overall stomach 103; this phenomenon is called tonic contraction. The peristaltic waves 801 and tonic contraction encourage the food 802 to be further broken down and thus digested. Food that is broken down to a point where it is more of a liquid is referred to as gastric chyme 805. The peristaltic waves 801 more easily move this gastric chyme 805 past the pylorus 803 and into the duodenum 804, and conversely larger undigested pieces of food 802 are pushed back into the stomach 103 to be further digested in an effect called retropulsion. Understanding gastric motility can be helpful to the clinician in many ways. First, if the patient appears to have good motility, there is less risk the patient may reflux gastric contents into their lungs. Second, good motility may indicate the clinician can accelerate the level of nutrition for the patient, which would potentially assist with recovery. Certain embodiments provide advantageous means for measuring motility.

A. Determine Motility Using Acoustic Sensor

In an exemplary embodiment, an acoustic sensor is used to measure gastric motility. This acoustic sensor 104 can be located on the distal tip of the feeding tube 102, as shown in FIG. 8. This acoustic sensor 104 can measure different frequency ranges and types of vibrations including, but not limited to, vibrations associated with frequency range of audible sounds (20-20,000 Hz). In an exemplary embodiment, a piezoelectric sensor is used to measure the acoustic signals. A number of other exemplary sensors can be used to measure acoustic signals, including but not limited to an electret, condenser, piezoelectric crystal, piezoelectric ceramic, piezoelectric film, or contact accelerometers. The vibrations measured by the acoustic sensor 104 can originate from a number of sources, including but not limited to peristalsis, gas bubbles, flatulence, and sounds from nearby organs, such as the lungs, heart, or small bowel. The study of phonoenterography revealed that bowel sounds increased in intensity during a meal and high intensity persisted for more than two hours after the meal according to Watson et al, "Phonoenterography: the recording and analysis of bowel sounds." Gut. 1967 February; 8(1): 88-94, hereafter "Watson" which is hereby incorporated in its entirety herein by reference. Bowel sounds are complex with a mixture of tones and often in a sequence of closely connected sounds in a frequency range of 150 to 5,000 Hz.

A number of sources of vibration may be detected. In a study by Campbell et al, "Surface vibration analysis (SVA): a new non-invasive monitor of gastrointestinal activity." Gut, 1989 January; 30(1):39-45, (hereafter "Campbell" which is hereby incorporated in its entirety herein by reference) Campbell attempted to quantify these bowel sounds and measured vibrations in the 40-10,000 Hz frequency range with a piezoelectric sensor. Specific patterns of bowel sounds can be associated with the fasting state and the postprandial state associated with the food being digested and thus monitored to determine the same.

In one embodiment, an acoustic sensor detects the vibrations associated with the movement of a peristaltic wave. In this exemplary embodiment, the acoustic sensor 104 can be a piezoelectric-based accelerometer. In addition (or in the alternative), the accelerometer is capable of measuring movement (e.g., physical movement of the accelerometer itself), such as the peristaltic wave 801 that moves down the stomach 103. For example, the peristaltic wave 801 can be detected by detecting a pattern having a frequency of one to three contractions per minute, as shown in FIG. 8.

A positive indication of gastric motility (e.g., between 1 and 3 contractions/waves per minute) should correlate with the patient tolerating enteral nutrition, and therefore have sufficient sensitivity. In contrast, a negative indication of motility (e.g., less than 1 contractions/waves per minute) can help identify patients that are not tolerating nutrition, enabling the clinician to adjust care and monitor the patient more closely.

To ensure that the acoustic sensor 104 is functioning correctly, the monitor can routinely monitor other body sounds as a means to check if the apparatus is functioning correctly. In an exemplary embodiment, the monitor routinely captures an auscultated heart pattern. If the auscultated heart pattern is routinely captured correctly, this indicates the acoustic sensor is functioning correctly, and thus it can be inferred it is also correctly capturing gastric motility vibration measurements. In an alternative embodiment, the monitor can routinely capture acoustic signals from the sound emitter 118 to confirm the acoustic sensor 104 is functioning correctly.

In an exemplary embodiment, an acoustic sensor measures the vibrations associated with oscillating gas bubbles in the small intestine. In this exemplary embodiment, the acoustic sensor 104 can be a piezoelectric-based accelerometer. There is evidence these gas bubbles are continually present in the small intestine according to Liu et al. "Oscillating Gas Bubbles as the Origin of Bowel Sounds: A Combined Acoustic and Imaging Study." Chin J Physiol. 2010 Aug. 31; 53(4):245-53 hereafter "Liu" which is hereby incorporated in its entirety herein by reference. Bubbles can be identified by their oscillating frequencies. Further, the size of the bubbles can also be determined by the measured frequency. The size of the bubbles can change as they move within the different sized structures of the small intestine. In one embodiment, the pattern and frequency of the bubbles is analyzed to assess gastrointestinal motility and other gastric functions. The analysis of gas bubbles in the small intestine can be combined with the analysis of peristaltic waves in the gastric environment, or other sensor data, to assess overall gastrointestinal motility.

In an exemplary embodiment, the various gastric motility measurements can additionally be used to determine the effectiveness of the type and amount of enteral nutrition. In an exemplary embodiment, the patient condition can also be a factor in determining the effectiveness of the type and amount of enteral nutrition. By collecting data on the patient condition, the type and amount of enteral nutrition and/or the resulting measurement of gastric motility, it may be possible to guide the type and amount of enteral nutrition and/or obtain the optimal gastric motility for each patient condition. Conversely, analyzing these data can provide insights on which enteral nutrition types and amounts should not be used for specific patient conditions.

B. Determine Gastric Residual Volume Using Temperature Sensor

It is standard of care in hospitals to measure the volume of the gastric contents of patients receiving enteral nutrition. This procedure is referred to as measuring Gastric Residual Volume (GRV). Gastric residual volume is typically measured by attaching a large syringe to the proximal opening in the feeding tube and suctioning all of the gastric contents into the syringe. The syringe has measurement markings denoting the volume in milliliters, which is then recorded in the patient's medical record. A low volume of gastric contents may indicate the patient is tolerating enteral nutrition and has sufficient gastric motility. A high-volume of gastric contents may indicate the patient is not tolerating enteral nutrition and does not have sufficient gastric motility. A high-volume of gastric contents is defined as 250 mL according to McClave et al, "Guidelines for the provision and assessment of nutrition support therapy in the adult critically ill patient." JPEN J Parenter Enteral Nutr. 2009 May-June; 33(3):277-316, hereafter "McClave" which is hereby incorporated in its entirety herein by reference. A clinician can adjust the care of the patient based on receiving a high gastric residual volume measurement, such as reducing the rate of tube feeding, prescribing pro-kinetic agents or raising the head of bed. However, a high gastric residual volume may not always correspond to a gastric motility problem. In some cases, a gastric residual volume of over 250 mL may be required to trigger gastric emptying by the stomach into the small intestine, and thus a gastric residual volume of over 250 mL may be part of normal digestion. In addition, these gastric residual measurement calculations are often performed every four hours in acute care patients receiving enteral nutrition. This procedure therefore takes time away from the clinicians that otherwise can be used in treating patients. The procedure is also often unsanitary due to the removal and reinsertion of gastric contents.

In an exemplary embodiment, an indicator dilution technique is used to measure GRV. Indicator dilution techniques are well known and are widely used in medicine, scientific work and industry for measuring fluid (gas or liquid) volumes or flow rates. As described by Schoeller "Indicator Dilution Methods." Quality of the Body Cell Mass. Serono Symposia USA 2000, pp 55-67, hereafter "Schoeller" which is hereby incorporated in its entirety herein by reference, indicator dilution methods for measuring volume (or flow rate) are based on the principle of conservation of mass. The addition of a known quantity of tracer (indicator) to the pool of tracee yields, after equilibration, a solution wherein the final concentration of indicator is equal to the amount of indicator added divided by the pool volume. If volume is the desired read-out, then the equation is re-arranged: volume (pool size)=dose of tracer/concentration of tracer.

The validity of indicator dilution approach depends on four assumptions. First, the indicator mixes rapidly and thoroughly with the fluid in the pool. Second, after mixing is complete, the concentration of the indicator is homogeneous in the pool volume. Third, the indicator is distributed only to the pool volume of interest. Fourth, the tracer is stable (over the time period required for the measurements).

Although these assumptions are often valid in vitro, when indicator dilution techniques are applied in vivo (such as, for medical applications) some or even all of the assumptions typically are not satisfied perfectly. Thus, for medical (or other in vivo biological) applications, indicator dilution methods are rarely perfectly accurate. Nevertheless, these approaches are often accurate enough to be clinically useful. Moreover, as will be discussed below, it may be possible to partially adjust for systematic errors in measurement by incorporating empirically derived coefficients into the final equations that are employed for converting the measured signal into clinically useful information.

Indicators often are chemicals that can be easily detected, using appropriate analytical means. Examples include: radio-labelled compounds (e.g., tritium-labelled water), stable isotope-labelled compounds (e.g., 13C-labelled glucose), dyes (e.g., indocyanine green dye), or easily detected chemical entities (e.g., Li+cation, polyethylene gycol).

GRV has been measured, using an indicator dilution approach. In the laboratory, a model stomach showed that dilution of phenol red dye can be employed to determine "gastric" volume according to Hurwitz, "Measuring gastric volume by dye dilution." Gut 1981 February; 22(2):85-93, hereafter "Hurwitz" which is hereby incorporated in its entirety herein by reference. Subsequently, GRV measurement in patients was demonstrated using polyethylene glycol (PEG) as the tracer and turbidometry as the means for measuring PEG concentrations according to Hardy et al, "Determining gastric contents during general anaesthesia: evaluation of two methods." Can J Anaesth. 1987 September; 34(5):474-7, hereafter "Hardy" which is hereby incorporated in its entirety herein by reference. These authors showed that GRV measured using the indicator dilution technique was not significantly different from the GRV measured by aspiration (via a Levin nasogastric tube) of the gastric contents.

Temperature also can be a useful tracer. For example, cardiac output (i.e., the flow rate of blood through the heart) is commonly measured in clinical practice by injecting a known quantity of cold normal saline solution into the venous side of the circulation and detecting the resulting change in blood temperature in the pulmonary artery. In an exemplary embodiment, gastric residual volume is determined by measuring the temperature of gastric contents before and after a control. In this embodiment, a temperature sensor is located on the distal tip of the feeding tube, which can be connected via a wire to the monitor. The monitor 110 can take continuous temperature measurements of the gastric contents. The apparatus is similar to that shown in FIG. 8, but instead of an acoustic sensor 104 located the distal tip, a temperature sensor or thermistor is used. Of course, a combination of multiple sensors can be used, such as those sensors disclosed herein and other sensors, and such combinations should be considered within the scope of this invention. The monitor can then control a known amount of fluid to be introduced through the feeding tube and into the stomach, which in an exemplary embodiment can be 50 mL of distilled water cooled to a temperature of 1° C. Utilizing water as a control can be advantageous, since acute care patients require hydration and water is a safe substance. The temperature sensor can then continually measure the change in temperature of the gastric contents after introducing this control of cooled water. In an exemplary embodiment, the GRV can be calculated using the following equation:

$$GRV = k_1 \times k_2 \times V_{injectate} (T_{before} - T_{injectate}) / (T_{before} - T_{after})$$

In this equation, $V_{injectate}$ is the volume of cold water injected into the stomach via the feeding tube. $T_{before}$ is the temperature of the gastric contents prior to injecting the aliquot of cold water. $T_{injectate}$ is the temperature of the cold injectate. $T_{after}$ is the temperature of the gastric contents after the injection of the indicator. $k_1$ is a dimensionless constant that depends on the specific heat content of water, the density of water, the specific heat content of gastric contents and the density of gastric contents. $k_2$ is a dimensionless constant that accounts for the dead space volume of the feeding tube and perhaps other unmeasured sources of systematic error. In an exemplary embodiment, the rate in which the temperature change occurs throughout the gastric contents can be used to calculate GRV. Calculating the rate of change of the temperature can add information to improve the calculation of GRV or provide other insights that may prove helpful to the clinician. The nature of the stomach environment and the gastric contents are such that significant mixing occurs as part of digestion and the subsequent measured temperature change will be reflective of the entirety of the gastric contents. Other factors that can be used to calculate GRV include the rate of enteral nutrition, the rate of gastric emptying, and medicines that may be introduced into the gastric environment. Since there may be unaccounted—for factors that may influence the accuracy of the gastric residual volume calculation, the algorithm can also present a probability measurement associated with the volume calculation to help the clinician understand the relative certainty in the GRV calculation.

C. Determine Gastric Residual Volume Using Bioelectrical Impedance

In an alternative embodiment, Gastric Residual Volume can be determined in certain circumstances by measuring changes in the impedance of an alternating current applied in the abdominal region by electrodes according to Soulsby et al, "Measurements of gastric emptying during continuous nasogastric infusion of liquid feed: electric impedance tomography versus gamma scintigraphy." Clin Nutr. 2006 August; 25(4):671-80, hereafter "Soulsby" which is hereby incorporated in its entirety herein by reference. In the approach described by Soulsby, 16 electrodes (ECG pads) are applied in a circumferential pattern around the abdomen. Impedance changes are measured by passing a sinusoidal alternating current (50-100 kHz; 1 to 10 mA) between one pair of electrodes on the abdomen and measuring the resulting voltage drop between another pair of electrodes. In the approach described by Soulsby, impedance is measured from all the possible combinations of pairs of electrodes, and an impedance versus time curve is generated by a proprietary algorithm. The system is "calibrated" by introducing a 100 mL bolus of tube feeding into the stomach. The conductivity of the calibrating bolus of tube feeding formula is increased by dissolving 17 g/100 mL of table salt (NaCl) in the formula prior to introducing it into the stomach.

A similar approach to Soulsby is described by McClelland et al, "Epigastric impedance: a non-invasive method for the assessment of gastric emptying and motility." Gut. 1985 June; 26(6):607-14, hereafter "McClelland" which is hereby incorporated in its entirety herein by reference. There is also a similar approach described by Sutton et al, "Measurement of gastric emptying rates by radioactive isotope scanning and epigastric impedance." Lancet. 1985 Apr. 20; 1(8434): 898-900, hereafter "Sutton" which is hereby incorporated in its entirety herein by reference. The approach described by McClelland and Sutton is similar to the one described above, except that only four electrodes are employed (two on the anterior epigastrium and two on corresponding locations on the back). The system described by McClelland and Sutton uses "standard" impedance cardiography equipment for signal generation and detection, but employs appropriate low-pass filtering to exclude interference from cardiac signals. In the approach described by McClelland and Sutton, gastric volume is not measured; rather, the impedance based system is designed only to measure fractional changes in gastric volume after a test meal as a function of time. Thus, the primary read-out is the half-time ($t_{1/2}$) for gastric emptying.

Figure 9:
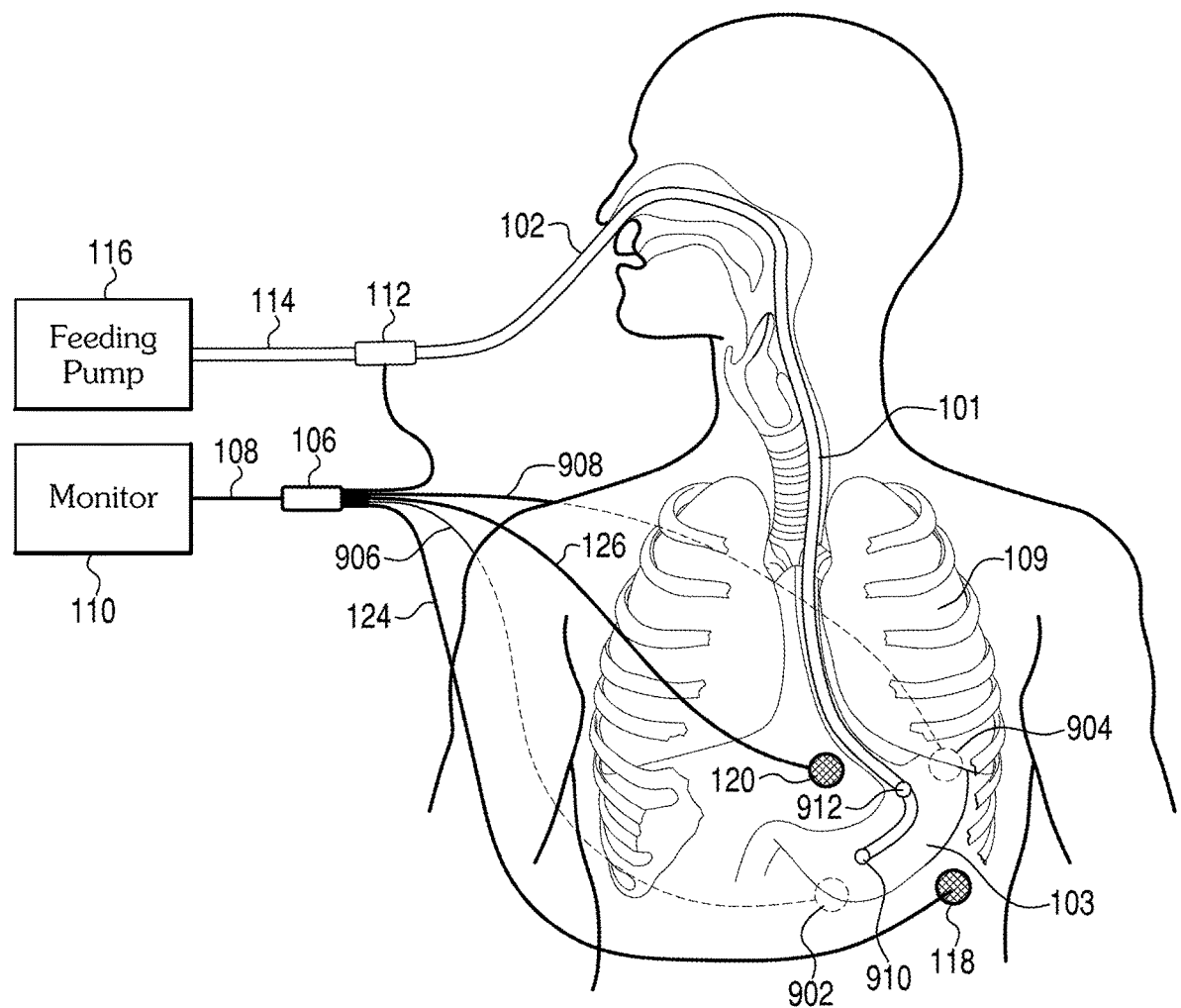
FIG. 9 is a schematic of an apparatus for measuring gastric residual volume in accordance with an exemplary embodiment.

In one embodiment, a GRV monitoring device can employ the electrode placement strategy described by McClelland and Sutton, as shown in FIG. 9. In an exemplary embodiment, a plurality of electrodes are placed on the abdomen. Here, four electrodes 118, 120, 902 and 904 are placed on the abdomen. An alternating electric current is driven through the patient's body between electrodes 118 and 902. The voltage between electrodes 120 and 904 may also be measured. The voltage measurement is filtered to only reflect the changes within the frequency range of the alternating current between electrodes 118 and 902. The voltage measurement comprises an impedance measurement whose amplitude depends in part on the GRV. Electrodes can have plural functions. For example, electrode 118 can record ECG signals during tube placement and serve as an anterior electrode that inputs alternating current for subsequent impedance measurement. Electrode 118 can be placed in the angle between the left costal margin (of the rib cage) and xyphoid process of the sternum (breast bone). Similarly, the electrode 120 can record ECG signals and also serve as an anterior electrode for measuring voltage for impedance measurement. Electrode 120 can be placed just caudal to the left costal margin at location that is about 4 finger-breadths (about 4-5 cm) to left of the midline. In this embodiment, electrode 902 can be placed on the posterior of the patient and input alternating current for subsequent impedance measurement. Electrode 904 can also be placed on the posterior of the patient and measures voltage along with electrode 120 for impedance measurement. In another embodiment, the same electrode placement strategy can be employed, except instead of placing a pair of electrodes on the posterior, these electrodes instead can be located on the distal end of the feeding tube and connected by wires (or conductive ink) to an appropriate fitting on the proximal end of the tube. In this exemplary embodiment, electrode 120 on the anterior abdominal wall and electrode 910 on the feeding tube can input, or "inject", an alternating current (50-100 kHz; 1 to 10 mA) into the patient. Each of the second electrode 912 on the distal end of the feeding tube and electrode 118 on the anterior abdominal wall can receive an alternating current from each of electrodes 120 and 910. Detecting the voltage and current between two of the electrodes, the impedance of the gastric contents plus other relevant tissues (e.g., fat, muscle, and skin) between the two electrodes can be determined. In an exemplary embodiment, the patient is electrically isolated from the external environment during this procedure.

Figure 10:
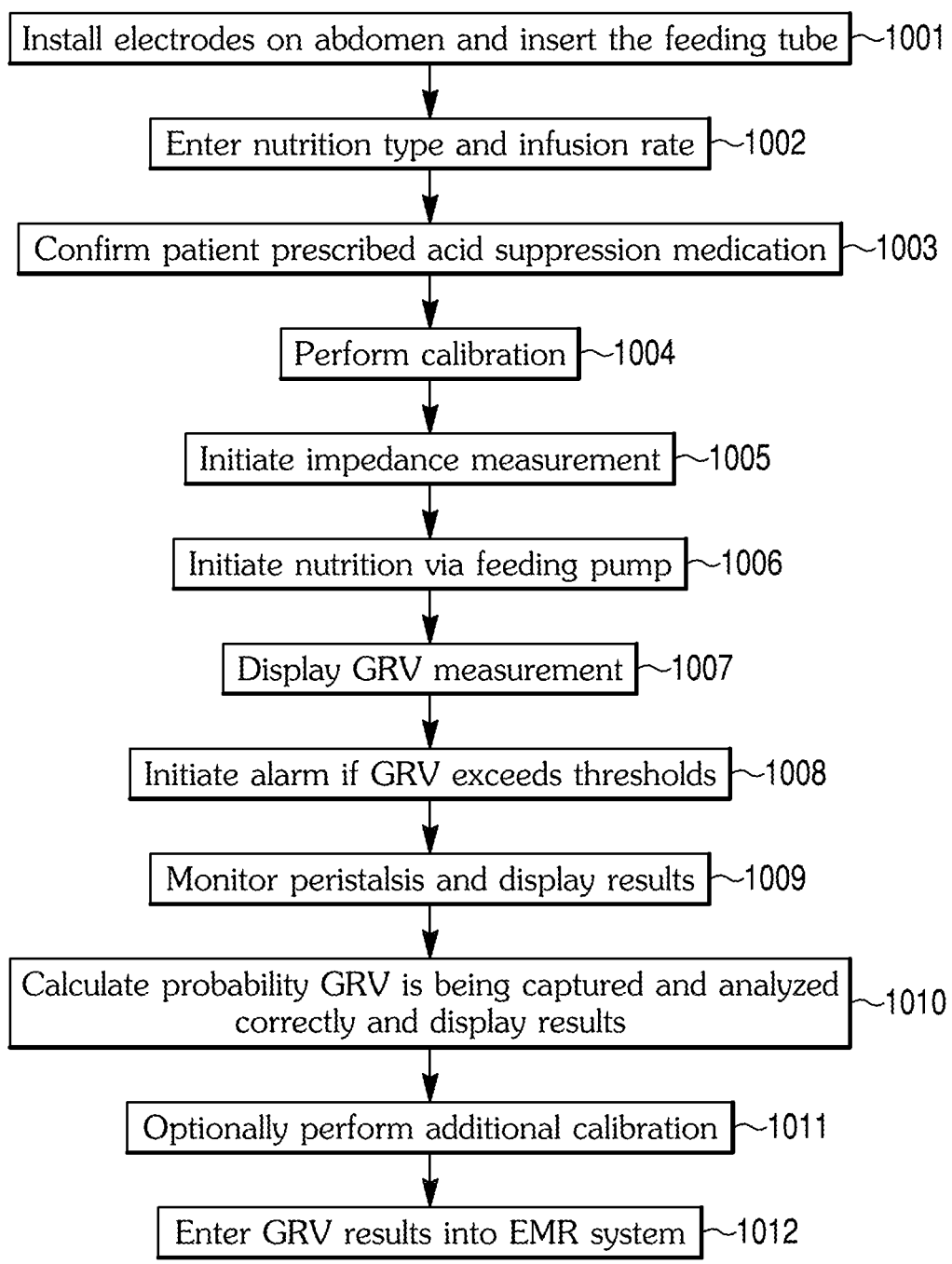
FIG. 10 is a flowchart of an exemplary method and apparatus for measuring gastric residual volume.

An exemplary process for utilizing the apparatus described in FIG. 10 to measure GRV via impedance is provided in FIG. 10. In the first step of this exemplary process 1001, the clinician installs electrodes on the abdomen and inserts the feeding tube. In step 1002, the nutrition type and infusion rate is entered into the monitor 110. In step 1003, the clinician confirms that the patient is prescribed acid suppression medication via the monitor 110. In step 1004, the system is calibrated by first emptying the stomach completely (by aspiration of contents via the feeding tube). Impedance is then measured with GRV=0. Then, a known quantity (e.g., 50 mL) of the prescribed tube feeding formula is injected into the stomach via the feeding tube and impedance measured again (e.g., with GRV=50 mL). For more accuracy, three-point calibration can be achieved by injecting a second bolus of tube feeding formula (e.g., another 50 mL aliquot) and again recording impedance. In step 1005, impedance measurement is initiated via the monitor 110. In step 1006, nutrition is initiated via the feeding pump 116. GRV measurement is then displayed on the monitor 110 per step 1007.

In step 1008, in audible and/or visual alarm is initiated if the GRV exceeds a defined threshold. This defined threshold of GRV measurement can be customized via a setup configuration of the monitor 110, and may include a default configuration based on patient sex, height, weight, feed type, fluid restriction, propofol rate, etc. In step 1009, the monitor 110 can display whether peristalsis has been detected or not. Knowing if peristalsis has been detected can help the clinician determine if nutrition is being tolerated. Peristalsis can be detected through described embodiments or other advantageous means. In step 1010, a probability is calculated to determine if the GRV measurement is being captured and analyzed correctly. This probability will be based on a number of factors, including but not limited to the GRV measurement value, the trending of GRV measurement values, nutrition type and infusion rate, prescription of acid suppression medication, calibration results, and peristalsis detection. The results of this probability calculation can be displayed on monitor 110. In step 1011, the clinician may decide to perform an optional additional calibration. In this optional calibration, the impedance measurement is noted via the monitor 110. The stomach is then emptied completely by aspiration of contents via the feeding tube. The clinician then manually measures the volume of the aspirated gastric contents. The clinician then enters the manually measured volume of the gastric contents into the monitor 110. The monitor 110 then utilizes the manually measured volume to calibrate the GRV measurements going forward. In step 1012, the GRV measurement results are entered into the EMR system.

In an exemplary embodiment, a conductivity sensor can be located at the distal end of the feeding tube. In an exemplary embodiment, the conductivity sensor can take the form of electrode 910. The conductivity sensor can be utilized to determine the conductivity (inverse of resistivity) of the gastric contents. This conductance measurement can be helpful for estimation of GRV, since the estimation of GRV using measurements of epigastric impedance (see FIG. 10) depends on conductivity of the gastric contents and the other structures (e.g., skin, muscle tissue, adipose tissue) and their volumes in the epigastric region being interrogated by the impedance measurement electrodes. The stomach contains relatively conductive material and when GRV increases, the measured impedance decreases. An increase in the conductivity of the gastric contents will also cause a drop in the measured impedance. By measuring the conductivity, this confounding variable can be factored out from the estimation of GRV. By extension, the measurement of GRV via impedance depends on a difference in impedance of the gastric contents and these other structures (e.g., skin, muscle tissue, adipose tissue). If the ionic strength of the tube feeding formula is too low, then the difference in impedance between the gastric contents and the other structures in the epigastric region of interest will be insufficient to provide a reliable signal for estimating GRV. In the research laboratory, this problem can be solved in a simple way by adding a large quantity (e.g., 9 g/L; 154 mEq/L) of sodium chloride (NaCl; table salt) to the standard tube feeding formula to ensure that the ionic strength of the tube feeding formula is sufficient to provide a good impedance signal for estimation of GRV. In the clinical setting, however, it would be ill-advised to add large quantities of sodium chloride to the tube feeding formulas that are administered to patients, since many patients cannot tolerate large loads of either sodium ion (Na+) or chloride ion (Cl−). Some commercial tube feeding formulas contain high concentrations of Na+ and potassium ions (K+), and therefore have sufficient ionic strength to permit reliable estimates of GRV, using the epigastric impedance methodology. One such formula is Osmolite 1.2, which contains 58 mEq/L of Na+ and 46 mEq/L of K+. Other commercial tube feeding formulas contain relatively low concentrations of Na+ and K+, and therefore may not have enough ionic strength to permit reliable estimates of GRV, using the epigastric impedance methodology. An example of this type of tube feeding formula is Nutrihep, which contains 7 mEq/L of Na+ and 33 mEq/L of K+. The ionic strength (and, hence, the conductivity) of the gastric contents is determined not only by the ionic composition of the tube feeding formula, but also by the secretion of ions (H+, K+, Cl−) by the gastric mucosa into the lumen of the stomach. Thus, in order to determine whether the contents of stomach at any given point in time have a composition that is suitable for determination of GRV would be desirable to continuously monitor the conductivity of the gastric contents. Moreover, since calibration of the epigastric impedance monitoring system (by injecting into the stomach a known volume of tube feeding formula) will be done only intermittently and the rate and composition of gastric secretion of ions can change on a minute to minute basis, it would be useful to adjust the GRV calibration settings continuously by taking into consideration measured changes (relative to the value measured at the time of calibration) of the conductivity of the gastric contents.

D. Determine Motility Using Impedance Sensors

In an exemplary embodiment, impedance sensors like those described in this disclosure to measure reflux in the esophagus, can be used in the stomach to measure the patient's motility. In one embodiment, this measurement can function the same way as impedance sensors in the esophagus. While in the stomach, food and gastric secretions that span two sensors typically have a lower impedance measurement than if no food/secretions were spanning the sensors. Measuring the pattern of impedance that results from food coming into the stomach and draining into the small intestine can create data that can be interpreted as a measurement of motility. The timing, duration, sequencing, and other measurements from the impedance sensors can be interpreted and correlated with either normal or potentially abnormal motility. In an exemplary embodiment, the measurements from the impedance sensors can be correlated with the peristalsis waves within the stomach that are a normal function of digestion. This information can be used by the clinician to modify the nutrition delivery or potentially trigger other types of care. In the case where an algorithm determines there is abnormal motility, the level of nutrition can be automatically reduced to prevent the risk of aspiration. In another example, abnormal motility can trigger suction of gastric contents.

This impedance sensor data in the stomach can also be combined with sensor data in the esophagus, so the combination of motility data and reflux data, can then automatically reduce the feeding level, trigger an alarm, trigger suction, trigger a balloon, or actuate other features. Conversely, the sensor data can trigger an increase of the feeding level if proven algorithms determine that the patient has good motility, no reflux, and is tolerating the nutrition well.

III. Reflux Measurement System and Apparatus

Some embodiments are directed to methods and apparatus for addressing a reflux event in an esophagus. More particularly, some embodiments are directed to determining initiation of a reflux event, and taking remedial measures.

A. Reflux Measurement System

Figure 11:
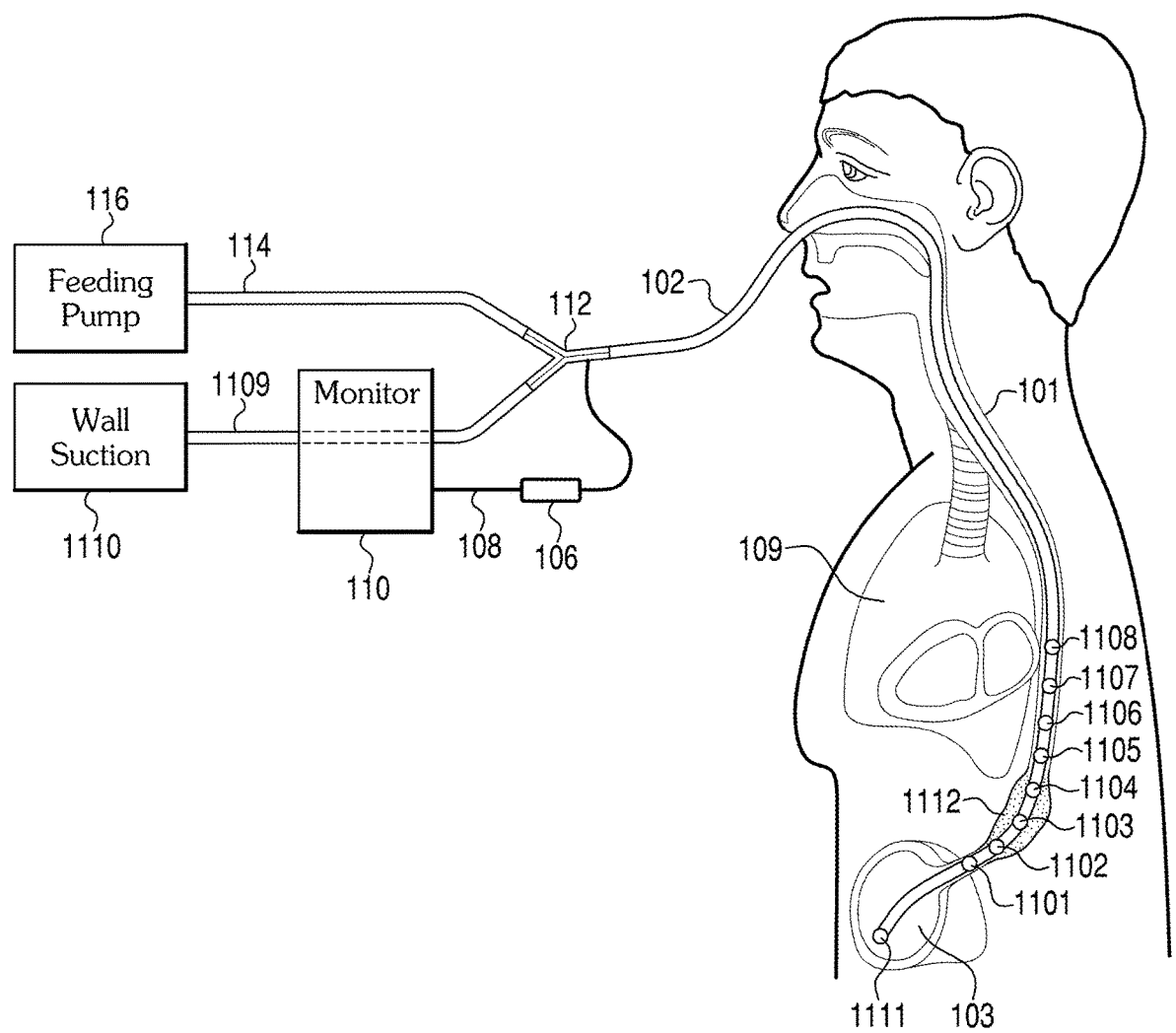
FIG. 11 is a schematic of an apparatus for monitoring reflux in accordance with an exemplary embodiment.

An exemplary apparatus for monitoring reflux and providing some protection from aspiration is shown in FIG. 11. In this exemplary embodiment, the patient utilizes a feeding tube 102 to receive enteral nutrition into the stomach 103. The enteral nutrition is administered by a feeding pump 116, which is conveyed via a feeding pump tube 114 and a tube connector 112. This feeding tube 102 contains impedance sensors 1101-1108 that are positioned on the outside of the tube 102 and along the tube section that is located in the esophagus 101. In an exemplary embodiment, there are eight impedance sensors 1101-1108 that comprise a conductive electrode in order to measure the impedance between two different sensors. When reflux material spans two sensors, the electrical impedance between the two sensors is reduced. This difference in measured impedance is captured by the monitor 110 via a cable 108 and electrical connector 106 that connects the impedance sensors 1101-1108 on the feeding tube 102 to the monitor 110. In specific circumstances, it can be determined that the patient is at risk for immediate aspiration, so in an exemplary embodiment the gastric contents are suctioned to prevent the gastric contents from being aspirated. In this embodiment, suctioning is accomplished via a suction tube 1109 that is connected to the feeding tube 102 via a tube connector 112. The suction tube 1109 is connected to wall suction 1110, which passes through monitor 110. Monitor 110 contains a valve that controls the level of suction from wall suction 1110 that is applied to suction tube 1109.

Figure 12:
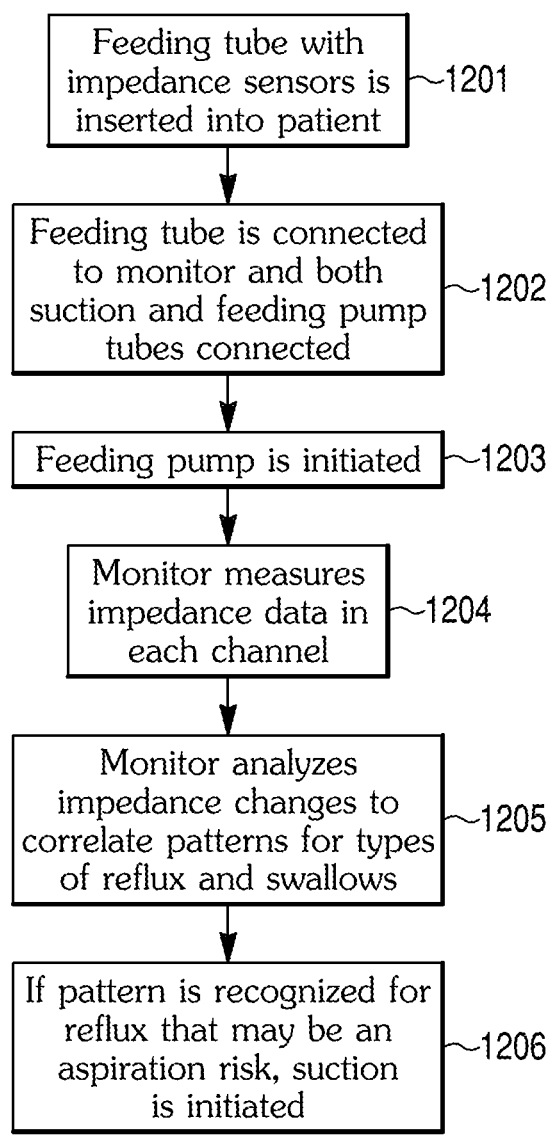
FIG. 12 is a flowchart of an exemplary method and apparatus for monitoring reflux.

An exemplary process for utilizing the apparatus described in FIG. 11 is provided in FIG. 12. The first step of this exemplary process 1201 is to insert the feeding tube 102 into the patient. This can be accomplished via the standard methods for inserting feeding tubes. In step 1202 the feeding tube 102 is connected to the monitor via cable 108, to wall suction 1110 via suction tube 1109 and tube connector 112, and to the feeding pump 116 via the feeding pump tube 114. In step 1203, the feeding pump 116 is initiated and enteral nutrition starts to flow through the feeding pump tube 114 into the feeding tube 102 via the tube connector 112. In step 1204, the monitor 110 continually measures impedance data from the impedance sensors 1101-1108 on the feeding tube 102. In step 1205, the monitor 110 continually analyzes the changes in the impedance data to determine if the changes correlate to patterns that may indicate reflux or swallows. In step 1206, suction can be initiated if a pattern is recognized for reflux. This suction is initiated by monitor 110 opening a valve that enables wall suction 1110 through suction tube 1109 and feeding tube 102 via the tube connector 112.

B. Feeding Tube Design

An exemplary embodiment for the device that captures data in the reflux monitoring system is a feeding tube. In this embodiment, the feeding tube can be any relevant feeding tube used in acute care or delivering enteral nutrition to patients. In one exemplary embodiment, the feeding tube is of size 14 Fr., which has an outer diameter 4.7 mm. Other exemplary embodiments can include other feeding tube sizes, which can include, but is not limited to 10 Fr., 16 Fr., and 18 Fr. In an exemplary embodiment, the tube is in the form of a Levin Feeding Tube. This is a non-sterile standard Levin type feeding tube for nasogastric or orogastric insertion. Other exemplary embodiments can include other feeding tube forms, which can include, but is not limited to, Salem Sump style feeding tubes, Dobhoff feeding tubes, Keofeed feeding tubes, small bore feeding tubes, pediatric feeding tubes, and nasojejunal feeding tubes. In one exemplary embodiment, the feeding tube is 48 inches (122 cm) long. Other exemplary embodiments can include other feeding tube lengths.

In an exemplary embodiment, the feeding tube is made of polyurethane. In another exemplary embodiment, the feeding tube is made of PVC. In another exemplary embodiment, the feeding tube is made of silicon. Other exemplary embodiments can include other feeding tube materials.

In an exemplary embodiment, the feeding tube has holes in the distal tip of the tube to allow enteral nutrition to enter the gastric environment, or enable suction to remove gastric contents. These holes can be of a different number, sizes and shapes and can additionally include a hole in the tip of the feeding tube.

In an exemplary embodiment, the tube includes radio opaque material to confirm placement in the stomach 103 and esophagus 101 with an X-ray. In an exemplary embodiment, radiopaque markings can be placed at 30 cm, 40 cm, 50 cm and 60 cm from distal end. Other exemplary embodiments can include other placements of radiopaque markings or radiopaque material can be included in the tube material. In an exemplary embodiment, radiopaque material can be placed along the length of the feeding tube, and potentially be integrated into the feeding tube via the tube extrusion process. In another exemplary embodiment, the impedance sensors can potentially serve as the radiopaque markings. Other radiopaque materials and placements can be used. These radiopaque markings can be used in combination with other techniques to determine tube placement. For example, if the nomogram recommends a depth of 50 cm from the nose, and the tube is inserted to this distance, the likelihood is higher that the plain film X-ray will show the feeding tube to be in the correct position. It is desirable for the impedance sensors to be radio-opaque enough to be visible on a plain X-ray film, e.g. regular chest X-ray. In general, correct position is defined as all impedance sensors being located in the thoracic region of the esophagus, i.e. the sensor closest to the feet is above (superior to) the stomach.

In an exemplary embodiment, it may be desirable for half the sensors to be above the carina (a clear landmark on chest X-ray) and the other half of the sensors to be below (inferior to) the carina but still above the diaphragm. A potentially accurate method of measuring the extent of reflux is measuring based on the location of the carina. This apparatus and method allows for reporting of the height of reflux events relative to a fixed part of the body, e.g. the carina, rather than relative to the feeding tube. In this exemplary embodiment, the feeding tube has radio-opaque markers that are numbered or otherwise distinguishable from one another. For example, the most distal sensor (closest to the feet) can be 1 bar. The next sensor can be 2 bars, so on and so forth, until the most proximal (the $6^{th}$ sensor) can be 6 bars. After insertion to the recommended depth (using an acoustic sensor, nomogram, or any other method) a plain X-ray may be taken. Description of the acoustic sensor and its use described elsewhere herein may be implemented as all or part of sensor 1111. The monitor then asks the user to input the number of bars for the impedance sensor that is closest to and below the carina. The carina may be a preferred reference point since it is both easily identified by most clinicians and it is located approximately in the midpoint of the thoracic, so it represents the point approximately half way up the esophagus. Once the sensor information is inputted (as above) the monitor can then report whether reflux is occurring "below" or "above" the carina. Therefore, instead of (or in addition to) reporting height of reflux relative to the feeding tube, e.g. 10 cm, the reporting of height is relative to the approximate midpoint of the esophagus, with higher reflux, i.e. superior to the carina, being more extensive.

An alternative embodiment for confirming the location of a feeding tube is to measure the tube insertion relative to the location of the Lower Esophageal Sphincter (LES). In an exemplary embodiment, a small balloon is integrated into the feeding tube. This is similar to an endotracheal tube in concept. After inserting the feeding tube into the stomach, one inflates a high volume (e.g. 100 ml) low-pressure balloon at or near the distal end of the tube. After inflation with 100 mL of air using a standard syringe, one gently pulls the tube out until there is pressure resulting from the balloon hitting the LES. It may be desirable for the balloon to be 10 or 15 cm from the tip of the feeding tube such that when resistance is met, the tube is taped in place, and one knows that the tip of the feeding tube is in the stomach to allow for administration of tube feeds and medications into the stomach. Using this approach, it would be desirable for the most distal (closest to tip) impedance sensors to be located 5-10 cm from the area of the balloon that is closest to the head. At the conclusion of placement of the feeding tube, the balloon is deflated (i.e. air removed) and the feeding tube is taped, bridled, or otherwise affixed to the nose in the example of nasal insertion. This method and apparatus may accurately locate the LES, and more particularly, a length of the passage from the point of tube insertion (e.g., mouth or nose) to the LES. The approach may alleviate the need to confirm tube placement with an X-ray since the feedback of knowing the tube is located proximal to the LES may also confirm it is not in the lungs or curled up in the stomach given the known length of the tube proximal to the balloon.

In an exemplary embodiment, the tube includes tube length markings or other indicia to indicate a length of the tube from its distal tip and thus be used by the clinician to determine a length of a tube inserted into the patient. For example, the tube length markings may start at 25 cm from the distal tip to 85 cm in 5 cm increments. These tube length markings will allow the clinician to determine how much of the feeding tube has been inserted into the patient. Other exemplary embodiments can include other tube length markings.

Exemplary feeding tubes may utilize sensors to measure potential reflux in patients. In one exemplary embodiment, impedance sensors may be utilized, which generally contain sensor material that is conductive in order to measure the impedance between two different sensors. In one example, a bolus 1112 of stomach contents moves up the esophagus 101 in a retrograde movement, as shown in FIG. 11, and simultaneously comes into contact with multiple impedance sensors 1102, 1103 and 1104. The impedance between each adjacent pair of impedance sensors may be continually measured. In an exemplary embodiment, this continuous measurement is at a frequency of 50 Hz. Other advantageous frequencies can be used in the successful operation of the product. When bolus 1112 spans two sensors, 1102 and 1103, the electrical impedance between the two sensors, 1102 and 1103, is reduced. This measurement of the impedance between two sensors may be referred to as measuring the impedance of a channel. Additionally in this example, the bolus 1112 spans sensors 1103 and 1104, reducing the impedance in this additional channel. In an exemplary embodiment, the impedance sensors 1101-1108 are spaced 2 cm apart. Other exemplary embodiments can include other sensor space locations. In an exemplary embodiment, the feeding tube 102 will contain six channels and thus eight impedance sensors located approximately 25 cm to 50 cm from the distal tip, such as being located at 30 cm for sensor 1101, 32 cm for sensor 1102, 34 cm for sensor 1103, 36 cm for sensor 1104, 41 cm for sensor 1105, 43 cm for sensor 1106, 45 cm for sensor 1107 and 47 cm for sensor 1108, from the distal tip. These locations assume the gastro-esophageal junction, also the location of the LES, is located approximately 25 cm from the distal tip. Other exemplary embodiments can include other total number of impedance sensors and other locations of sensors.

In one exemplary embodiment, sensor 1111 may be implemented as a pH sensor 1111 that is located on or adjacent the distal tip of the feeding tube at 0 cm location, as shown in FIG. 11, or at a location 0 cm to 5 cm or 0 cm to 15 cm. The pH sensor 1111 may be used to measure the pH of the gastric contents. In an exemplary embodiment, this pH sensor 1111 is used in conjunction with a drug to determine if a patient may tolerate enteral nutrition. In this embodiment, the feeding tube may measure the pH change before and after administration of the drug.

The pH sensor 1111 can be placed in other locations along the feeding tube. One exemplary embodiment is to place a pH sensor 1111 at approximately 25 cm from the distal tip and to use the sensor to measure pH and help determine if there is reflux present. This pH information can augment the impedance information or be used independently. In an exemplary embodiment, if pH drops at the same time the impedance sensors measure a drop in impedance, the pH drop can be considered additional confirming evidence there is reflux Additionally, the pH sensor 1111 can provide the pH of the potential reflux helping to determine the relative acidity of the reflux. The level of acidity can be used in determining the appropriate level of care. For example, reflux at a low pH can be more damaging to the esophagus and lungs, so specific care can be initiated, such as prescribing acid suppressants, prescribing pro-kinetic agents, or further raising the head-of-bed.

In an exemplary embodiment, the pH sensor 1111 will conform to the following specifications. The pH sensor material consists of antimony. The pH sensor 1111 may measure and display pH to at least one decimal place, i.e. x.x. The sensor accuracy (offset) of the initial pH measurement may have a margin of error of +/−0.3. Subsequent pH measurements may have precision of +/−0.1. The pH sensor 1111 can have an internal reference for ease of use. The pH sensor 1111 may have a useful life of 3 days.

In one exemplary embodiment, the impedance sensors can take the form of metal rings that are to be applied to the feeding tube to measure impedance between the metal rings. An exemplary material for these sensors can be stainless steel, but other exemplary metal materials can be used that satisfy the impedance measurement requirements. Impedance sensors utilizing metal rings, and specifically stainless steel, may have a similar design, for example, as those provided with the Sandhill Scientific ZepHr catheters that are used to measure reflux to assist in the diagnosis of Gastro-Esophageal Reflux Disease (GERD) (see http://www.sandhillsci.com/index.php?activePage=reflux&page=zprobes) but have a size to wrap around a feeding tube that is sized 10-18 Fr.

In an exemplary embodiment, metal rings are integrated into the feeding tube 102 to measure impedance in patients that are receiving enteral nutrition. An exemplary embodiment for integrating metal rings can be to create the feeding tube with two lumens. The main lumen is utilized to deliver food to the stomach and to apply suction to remove stomach contents. A second lumen is utilized to route wires that will connect to the metal rings to help complete an impedance measurement circuit. In this embodiment, the metal rings are attached by bending around the outside of the feeding tube, staying in place by either friction, bonding via an adhesive material, or some exemplary combination. These metal rings can substantially cover the circumference of the feeding tube, partially cover the circumference or cover the entire circumference. In this embodiment, each wire that is drawn through the lumen is drawn through a hole in the feeding tube at each location of a metal ring and soldered to the metal ring. Exemplary embodiments can include various sizes, shapes, and different locations in the lumen to sufficiently connect the metal rings.

In an exemplary embodiment, the proximal end of the feeding tube has an electrical connector that connects the wires in the second lumen to a cable that will enable connectivity to a controller or a monitor. The electrical connector can connect these wires in many different ways.

In an exemplary embodiment, an electrical connector 106 will connect the wires attached to the sensors 1101-1108 to a cable 108 that will connect with a monitor 110. In an exemplary embodiment, this cable 108 is 2 m in length, although other exemplary lengths can be used. In an exemplary embodiment, this cable 108 has an RJ-45 connector at the end that will connect to the monitor 110, although other exemplary connectors can be used.

Figure 13:
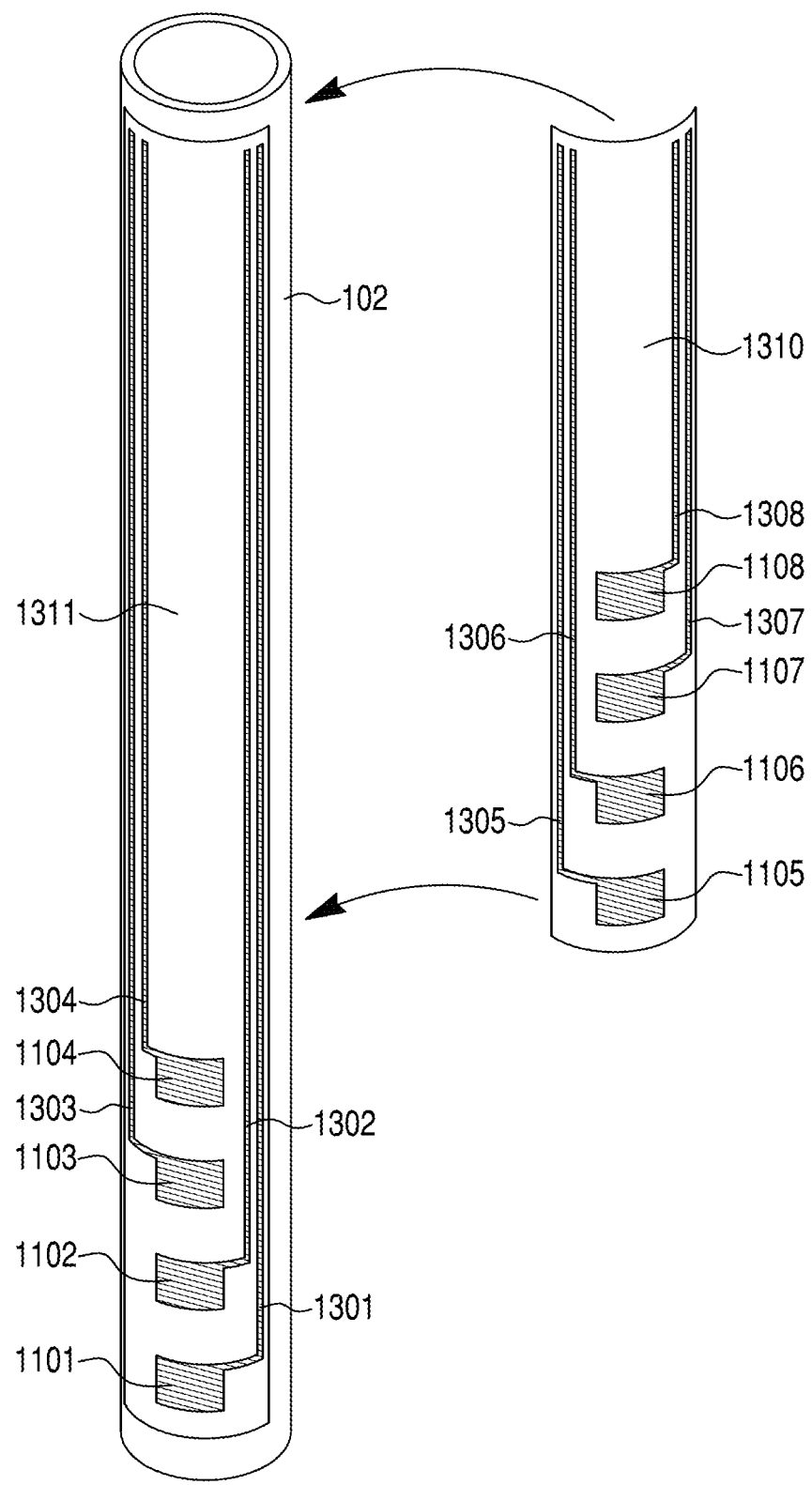
FIG. 13 is a schematic of an exemplary conductive ink approach for measuring impedance.

In an exemplary embodiment, conductive ink is utilized as the sensors 1101-1108 instead of metallic rings, as shown in FIG. 13. In an exemplary embodiment, the wires 1301-1308 that connect to the sensors 1101-1108 may instead be formed of a conductive ink. Many different types of conductive ink can enable effectively collecting this data. In an exemplary embodiment, the conductive ink used is AGCL-675 Silver/Silver Chloride Ink provided by a company called Conductive Compounds. In these embodiments, the conductive ink is printed or otherwise applied directly to the surface of the feeding tube. In one exemplary embodiment, the conductive ink wires 1301-1308 and sensors 1101-1108 are applied by a printing process to thin films 1310-1311. The conductive ink can be applied in other exemplary processes such as a pad, pen, inkjet, laser, screen print, nano-based processes and other processes that may prove advantageous. An exemplary pattern for printing the conductive ink wires 1301-1308 and sensors 1101-1108 is in a design that does not allow the wires or the sensors to overlap on the printed thin films 1310-1311 surface. An exemplary design can be made of different layers of ink and dielectric. One exemplary embodiment is to print these different layers as part of a printing process. An exemplary process for printing is to first print a dielectric material in a pattern that matches the wiring pattern. In this exemplary process, no dielectric is printed where the design specifies sensors 1101-1108. In this exemplary process, the conductive ink wires 1301-1308 are printed on top of the dielectric pattern. In this exemplary process, the sensors 1101-1108 are then printed on the thin films 1310-1311 in such a way as to be in contact with the conductive ink wires 1301-1308. In this exemplary process, an adhesive material is then printed on top of the wires 1301-1308 and sensors 1101-1108.

In an exemplary process, the conductive ink wires 1301-1308 and sensors 1101-1108 are applied to the feeding tube 102 via a combination of pressure and heat. In this exemplary process, specific tooling is created for the size of tube 102 where the conductive ink is applied. The conductive ink film 1310-1311 and tube 102 are placed in the tooling and then heat is applied to activate the adhesive material. The tooling also applies pressure to press the conductive ink onto the tube 102. After this process, the film 1310-1311 is removed from the tube 102, leaving only the printed conductive ink and dielectric material remaining on the tube 102. The resulting tube 102 includes a plurality of sensors 1101-1108 adhered to the tube and exposed to the external through openings in the dielectric material to the environment. Each of the plurality of sensors 1101-1108 are connected to a corresponding one of the conductive ink wires 1301-1308, also adhered to the outer surface of the tube but insulated from the external environment from the dielectric material.

The size and shape of the conductive ink sensors can take many exemplary forms. In one exemplary embodiment, the sensors 1101-1108 are in the form of a rectangle that covers a portion of the circumference of the tube 102, as shown in FIG. 13. Other exemplary shapes can be used, such as a square, oval, circle, etc. Per FIG. 13, an exemplary approach to connecting the sensors 1101-1108 to the monitor 110 is via conductive ink wires 1301-1308 that transverse the tube from the sensors 1101-1108 to an electrical connector 106. An exemplary pattern for the conductive ink wires 1301-1308 is to run parallel to the length of the film 1310-1311 and connect to the sensors 1101-1108 via a right angle. There may be other exemplary patterns for efficiently printing the conductive ink wires 1301-1308 to each sensor 1101-1108. An exemplary thickness of the conductive ink wires is about 0.020 inches, but other thicknesses can be used.

The size and shape of the films 1310-1311 the conductive ink wires 1301-1308 and sensors 1101-1108 are printed on and the number of sensors 1101-1108 printed can vary depending on the size of the tube 102, the location of the sensors 1101-1108 to capture sensor data, and the number of sensors 1101-1108 required to capture the data. An exemplary size and shape is shown in FIG. 13, where two conductive ink films 1310-1311 can be utilized to capture the required sensor data. In this exemplary embodiment, the tube 102 to which the conductive films 1310-1311 are applied is a 14 Fr. Levin tube that is 4.67 mm (3/16 inch) outer diameter and 122 cm (48 inches) long. In this exemplary embodiment, each of the films 1310-1311 can cover an arc of 120 degrees when placed on the 14 Fr. tube 102, equating to a film width of 4.92 mm (0.193 inches). The length of the first film 1310 can be 50 cm (19.66 inches), and the length of the second film 1311 can be 62 cm (24.41 inches). Each film can contain 4 impedance sensors, which enables three channels of sensor data collection since two adjacent sensors can form a channel.

The positioning of each film 1310-1311 depends on factors such as tube length and the area to be monitored. In this exemplary embodiment, the proximal end of both films 1310-1311 can be placed starting at 90 cm from the distal tip of the feeding tube. In this exemplary embodiment, each film 1310-1311 can be positioned 180 degrees with respect to the other, so they effectively cover opposite sides of the tube. This embodiment should enable effectively capturing the data and positioning the films 1310-1311 optimally for ease of production.

In this embodiment, the first sensor 1101 can be positioned approximately 30 cm from the distal tip. This position should be advantageous since the lower esophageal sphincter is located approximately 25 cm from the distal tip. Therefore, reflux is measured starting at 5 cm above the lower esophageal sphincter. As a comparison, the clinical diagnosis of GERD is reflux reaching 5 cm above the lower esophageal sphincter. In this embodiment, each impedance sensor is located approximately 2 cm from the other.

At the proximal end of the tube 102 near where the thin films 1310-1311 are positioned at 90 cm, conductive ink can be designed and applied to facilitate connecting to electrical connector 106 and cable 108. The conductive sensors 1101-1108 and wires 1301-1308 need to be connected to an electrical connector 106 that is part of cable 108 that then connects to the monitor 110. A specially designed conductive ink pattern will facilitate connecting the conductive ink wires 1301-1308 to this electrical connector 106. In an exemplary embodiment, the electrical connector 106 has conductive connection points lining the inner diameter that when placed over the outer diameter of the tube 102 makes electrical contact with the conductive ink pattern and completing an electrical circuit.

C. Monitor Cable Design

In an exemplary embodiment, a cable 108 is used to connect a monitor 110 with the feeding tube 102. In this exemplary embodiment, this cable 108 is approximately 2 m long. At one end of the cable 108, a female RJ-45 connector can connect with a male RJ-45 from the electrical connector 106. At the other end of the cable 108, a male RJ-45 can connect directly into the monitor 110. The cable 108 can have protective material that is appropriate for a clinical setting, such as resisting bodily fluids. The cable 108 is meant to be reusable.

D. Suction and Feeding Pump Connector Design

Figure 14A:
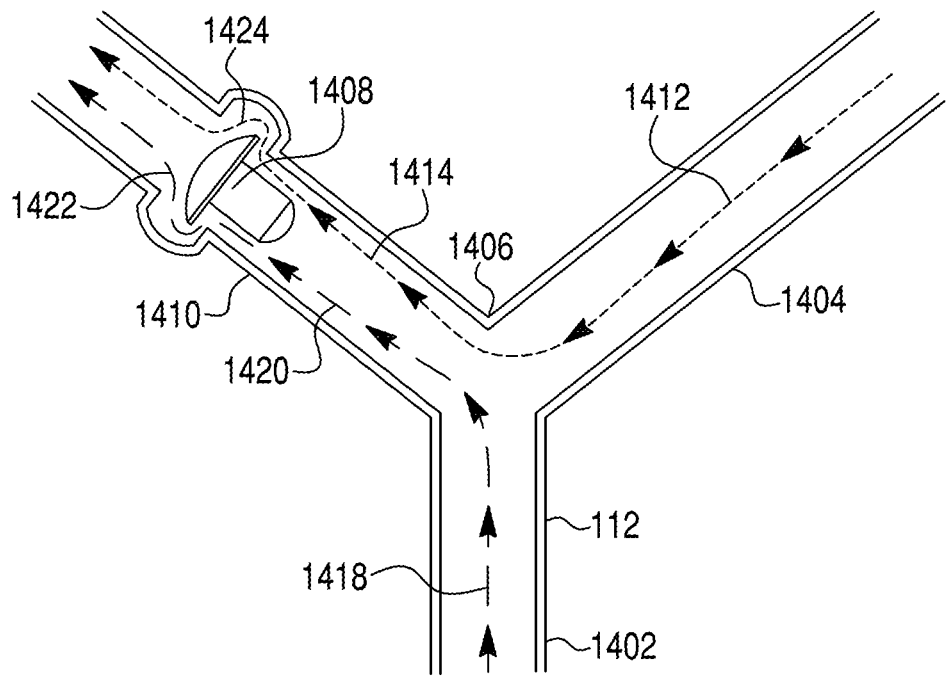
FIGS. 14A-14B are schematics of an exemplary tube connector.
Figure 14B:
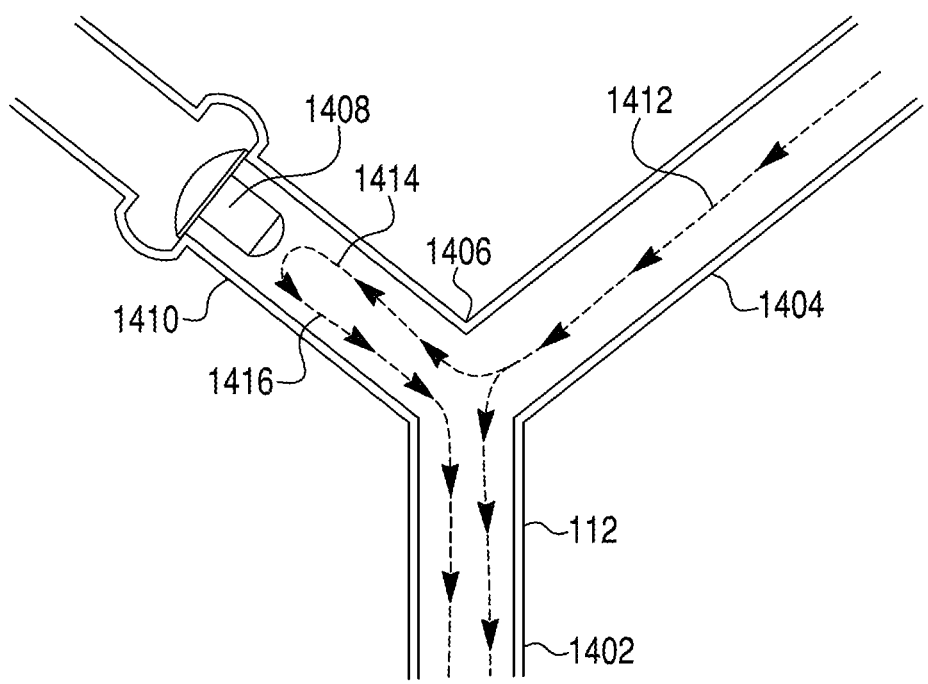

A tube connector 112 connects the feeding tube 102 to the tubes leading to the feeding pump 116 and the wall suction 1110. In an exemplary embodiment, the feeding tube 102 is used both to deliver the enteral feed and to enable suction of stomach contents. In an exemplary embodiment as shown in FIG. 14a, the connector can have a "Y" pattern. The bottom portion 1402 of the connector 112 can connect to the feeding tube 102. The right side 1404 of the connector 112 connects to the feeding pump tube 114 leading to the feeding pump 116. The left side 1410 of the connector 112 connects to the suction tube 1109 leading to the wall suction 1110. Enteral nutrition can follow the general path from the feeding pump 116, down the feeding pump tube 114 into the tube connector 112, and then into the feeding tube 102. The specific path of enteral nutrition within the connector 112 is the enteral nutrition enters the connector 112 at point 1412 and as the nutrition passes corner 1406 some tube feeds may go toward the left side 1410 of the connector, but the nutrition will be blocked by valve 1408 that is closed. Having been blocked by valve 1408, the enteral nutrition will pass point 1416 and proceed to back to bottom portion 1402. The valve 1408 can take many exemplary forms with the key operating criteria that when suction is applied the valve pulls open, but when fluid tries to push into the valve, it remains closed given the large pressure differences between suction and the feeding pump. Many exemplary valves may meet these criteria such as the umbrella type valve shown in FIGS. 14A-14B, which may include, but is not limited to, butterfly valves, belleville valves, and duckbill valves. In some examples, a deformable suction may be created on the vacuum pump side which collapses because of the pressure difference between the suction and atmospheric pressure. This deformable region may permit the check valve to open in the deformed state and/or lower its stiffness.

In an exemplary embodiment as shown in FIG. 14A, suction can be applied to remove the gastric contents. The wall suction 1110 is controlled at the monitor 110 to a setting of being on or off. After the suction is turned on, the valve 1408 opens and enables the suctioning and removal of all gastric contents. These gastric contents are sucked up into the lumen of feeding tube 102 in a retrograde motion and into connector 112. Once in connector 112, they first pass point 1418, and then are drawn to the left side 1410 and pass point 1420. The gastric contents then continue around valve 1408, past point 1422, and onward to a collection trap at the wall suction 1110 or monitor 110 location. In this illustration, valve 1408 is in an open position due to the suction force. When suction is turned on, any tube feeds that may be coming from the feeding pump may also be suctioned into the suction tube 1109. Specifically, the tube feeds will enter on the right side 1404 and pass point 1412. The suction force then draws all or a portion of the tube feed around corner 1406 and past point 1414, where it continues around valve 1408 and past point 1424. This suctioning of any tube feeds is not detrimental to the patient since it is intermittent and clinicians can decide whether to discontinue or change the rate of administration of tube feeds. This connector 112 is designed to come with the feeding tube 102 and thus be disposable along with the tube.

E. Monitor Design

The monitor 110 may comprise a computer (e.g., controller) and a display. The computer may be programmed (e.g., have access to a software program) to monitor patient conditions by receiving sensor data as described herein, and to initiate and control actions of apparatuses as described herein (e.g., provide commands or other signals to servos, pumps, voltage supplies, etc.). The monitor 110 may include a user interface to allow input of data and commands to the monitor 110, such as a touch screen display, a mouse, a track pad, a keyboard, a microphone and voice recognition software, buttons, etc.

A "computer" refers to one or more apparatus and/or one or more systems that are capable of accepting a structured input, processing the structured input according to prescribed rules, and producing results of the processing as output. Examples of a computer may include: a stationary and/or portable computer; a computer having a single processor, multiple processors, or multi-core processors, which may operate in parallel and/or not in parallel; a general purpose computer; a supercomputer; a mainframe; a workstation; a micro-computer; a controller; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC); etc.

"Software" refers to prescribed rules to operate a computer that may be stored in a computer-readable medium. Examples of software may include: code segments; instructions; applets; pre-compiled code; compiled code; interpreted code; computer programs; and programmed logic.

A "computer-readable medium" refers to any storage device used for storing data accessible by a computer. Examples of a computer-readable medium may include: a magnetic hard disk; a floppy disk; an optical disk, such as a CD-ROM and a DVD; a magnetic tape; a flash removable memory; a memory chip; and/or other types of media that can store machine-readable instructions thereon.

A "computer system" refers to a system having one or more computers, where each computer may include a computer-readable medium embodying software to operate the computer. Examples of a computer system may include: a distributed computer system for processing information via computer systems linked by a network; two or more computer systems connected together via a network for transmitting and/or receiving information between the computer systems; and one or more apparatuses and/or one or more systems that may accept data, may process data in accordance with one or more stored software programs, may generate results, and typically may include input, output, storage, arithmetic, logic, and control units.

A "network" refers to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet. Exemplary networks may operate with any of a number of protocols, such as Internet protocol (IP), asynchronous transfer mode (ATM), and/or synchronous optical network (SONET), user datagram protocol (UDP), IEEE 802.x, etc.

Monitor 110 may serve several functions. For example, the monitor 110 may function may analyze the reflux data, present a summary to the clinician in a simple and intuitive manner, analyze the reflux data in real-time, initiate auto-suction if warranted, etc.

The specific design of the monitor and display may differ from the existing GERD related products that may also use impedance sensors. The physical design needs may include a display and a pole mounting connector to be conducive to an ICU or acute care setting. The data display may include both a summary of the reflux and suction events and the ability to see the raw data captured by the sensors. For the summary of reflux events, the data may be presented in text and/or graphical form as presented in the exemplary embodiment shown in FIG. 15. In this exemplary embodiment, viewing the specific time period for when the impedance data was collected can be set by input 1502 to a period of the last 3 hours, 6 hours, 12 hours, or 24 hours. In this exemplary embodiment, the text can be presented as a summary of the number of reflux and suction events over the past 24 hours and the range of height of the reflux events. For example, the display 1504 shows the number of times suction was triggered. The total number of reflux events in the last 24 hours is shown in display 1506, as well as a summary of how many reflux events achieved a specific height. The total number of swallow events during the 24-hour period is shown in display 1508, and the number of belching events is shown in display 1510. An option for providing more information on the patient history is to also have an arrow next to the number of events to denote whether the incidence of reflux is increasing (up arrow) or decreasing (down arrow).

In graphical form, time may be represented on the x-axis, as shown in display 1512, and reflux height may be represented on the y-axis, as shown in display 1514. A summary of the impedance data that is determined to be a reflux event is represented as arrows, such as in display 1516, that are positioned at the time of the reflux event on the x-axis and with the height of the reflux represented as the length of the arrow along the y-axis. Suction events can also be noted on the y-axis, such as in display 1518. A suction event or high level of reflux may also be indicated by a visual alarm condition, such as the red circle in display 1520. The area for display 1520 can also be used for conveying a non-alarm status, such as a green colored circle signifying that all measurements represent a normal or safe condition. Similarly, a low level of reflux or other combination of measurements can be represented by a yellow colored circle signifying caution. Swallow events can be shown, such as display 1522 and belching events can be shown, such as display 1524. The monitor may enable scrolling between time periods and zooming into specific time periods (expansion of selected time periods) to see more detail. The monitor can also enable input of other relevant data, such as when bolus feeding occurred, when there was a relevant event, such as spit-up/vomit, or when certain gastrointestinal-related medicines were taken. These additional data may help put the impedance data in better context and thus help the clinician understand how the patient is doing. In addition to the impedance data, the display can show a summary view of current and historical pH data, both for esophageal and stomach pH sensors.

Figure 16:
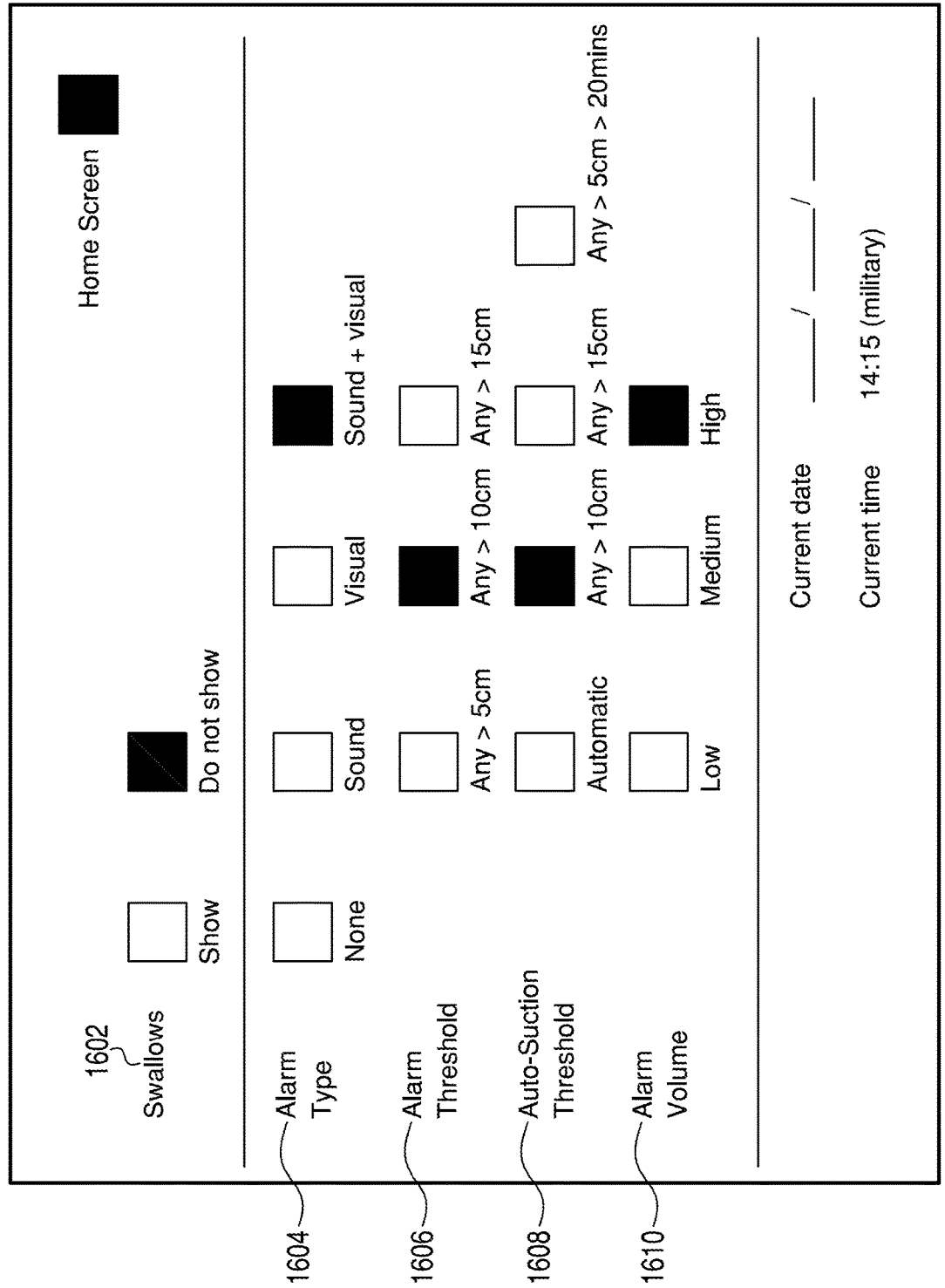
FIG. 16 is schematic of a user interface screen of the exemplary monitor of FIG. 11.

In an exemplary embodiment, the monitor 110 can provide access to an interface that enables setting preferences for the monitor 110 and feeding tube 102, as shown in FIG. 16. For example, setting preferences can include actions such as determining whether to monitor swallows or not, such as via input 1602. Settings can also include determining whether an alarm, as well as which type of alarm, should be initiated, such as via input 1604. Other alarm settings include the threshold upon which alarm is initiated, such as via input 1606, as well as the volume of the alarm, such as via input 1610. Settings may also include configuring the auto suction threshold, such as via input 1608. For example, the threshold can be configured to automatic, which is a combination of factors, or specifically to factors such as measured reflux greater than 10 cm, greater than 15 cm, or greater than 5 cm for over 20 minutes.

In an exemplary embodiment, the detailed impedance and pH data are recorded to a storage medium for later analysis. This storage medium can be a flash card, or something else that is simple to access and transfer to a PC for further analysis. Via an offline PC, the clinician can view the detailed impedance data collected since the measurements began. While viewing the data offline on a PC, a clinician may be able to input into the monitor 110 to add a reflux event and have it saved along with the other noted reflux events.

In an exemplary embodiment, the form factor of the monitor may be a small LCD or similar display adequate for readout. The monitor can have a size at least 3.5 inches diagonal and a minimum resolution of 320×480 pixels in color. The monitor can have a flat bottom, and thus the ability to rest on a shelf. A clamp accessory can enable connecting to a rolling IV type poll.

The monitor 110 can run on wall current and have battery backup containing replaceable batteries. In another exemplary embodiment, the monitor 110 can have a battery backup containing an internal rechargeable battery.

In an exemplary embodiment, hardware buttons are designed to facilitate both capturing and reviewing information. These buttons can facilitate capturing events, such as the feeding, reflux, vomiting, feeding intolerance, and medication administration events. These buttons can also have standard inputs for navigating and selecting items within the monitor UI. The buttons and monitor user interface can allow input of the patient's name and Medical Record Number.

In an exemplary embodiment, the screen is touch enabled, which can allow interacting with the software user interface via touch gestures directly on the screen. The monitor can also have a combination of a touchscreen and hardware buttons for interaction.

In an exemplary embodiment, the electronics of the monitor can be integrated into an alternative device, such as the electrical connector 106, tube connector 112, or a cloud-based computing device. In an exemplary embodiment, the electrical connector 106 can have all the electronics integrated into its packaging. This can include all processing, memory and data connectivity. In this scenario, the processing of the impedance data can occur at the electrical connector 106. The output of this processing can then be managed in multiple ways. For example, if during the processing of impedance data the algorithms determined auto-suction should be initiated, a solenoid valve can be integrated directly into the electrical connector 106 to initiate suction. In this embodiment, the electrical connector 106 is no longer a disposable part of the tube, but instead can be reusable. Another way the data can be managed is to enable viewing the summary data on an alternate device. This alternate device can be a PC, a mobile phone, a tablet, feeding pump, modular patient monitor or any other device capable of viewing the summary data. All set up and management functions for the feeding tube 102 that were previously described as occurring on the monitor 110 can instead be accomplished via an alternative device.

In this embodiment, power can be supplied to the electrical connector 106 to power the electronics. One option is to have a power cord that connects the electrical connector 106 to a wall outlet. This power cord can be advantageously attached to the suction tube 1109. Alternatively, in combination with low voltage processing and memory technology it can be possible to harvest the power from a number of potentially advantageous mechanisms, such as piezoelectric, thermoelectric, solar, and battery technologies. In one exemplary embodiment, this battery can be a standard battery situated within the electrical connector 106.

IV. Impedance Based Algorithms

A. Data Collection for Algorithms

Figure 17:
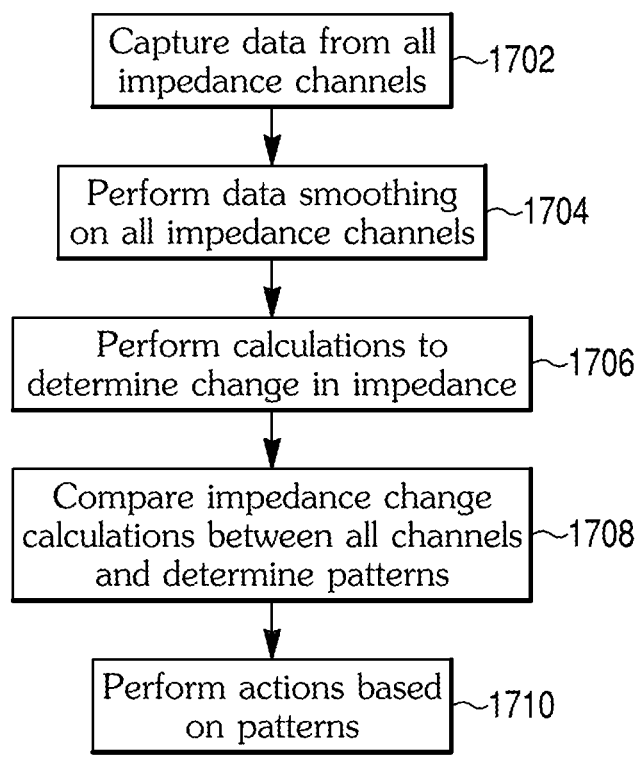
FIG. 17 is a flowchart of an exemplary method and apparatus for algorithms to determine presences of reflux.

In an exemplary apparatus, eight impedance sensors are utilized, consisting of two thin films where each thin film has four impedance sensors, as shown in FIG. 13. These impedance sensors are located approximately 2 cm apart. Two impedance sensors form one channel for data collection. Therefore, among the four impedance sensors there are three channels. Impedance is constantly measured between the two sensors in each channel. An exemplary process for collecting data from these impedance sensors is shown in FIG. 17.

The first step 1702 in the process is to capture data from all of the impedance channels. The data collected from the impedance sensors is the measurement of ohms between two sensors. The sensors do not necessarily have to be adjacent along the feeding tube. In the exemplary apparatus, the eight impedance sensors will therefore collect data as six channels. This data will naturally have small variations in a normal state within the esophagus, given factors such as minor changes in the esophageal environment. These small changes can be considered noise from an interpretation perspective, so the raw data needs to be smoothed in step 1704 in order to be processed in algorithms. Smoothing, which is a form of filtering, is the process of removing these minor variations in the data so the data can be more easily processed in algorithms to determine the patterns associated with specific conditions such as liquid reflux, gas reflux (belching), a swallow, or any combination. There are many exemplary techniques for data smoothing that can be utilized in this embodiment, including but not limited to moving average, least squares, exponential smoothing, and LOESS/LOWESS regression. The output of this smoothing step is to create an impedance measurement that can be used in the algorithms.

In an exemplary embodiment, the impedance data smoothing is calculated using an exponential moving average, as depicted by the formula below:

$$B_t = \alpha \times I_t + (1-\alpha) \times B_{t-1}$$

The coefficient α (alpha) represents the degree of weighting decrease. The coefficient alpha is a constant smoothing factor, where a higher alpha value discounts older impedance measurements faster. The variable $I_t$ is the impedance measurement at any time period t. The variable $B_t$ is the resulting impedance measurement after data smoothing at any time period t.

The impedance measurement can then be analyzed in step 1706 to provide information about the status of the patient. In an exemplary embodiment, the derivative of the above impedance function can be calculated to provide an indication of the rate of change in the impedance measurements. One exemplary way of calculating the derivative of the function Bt is via the following formula using Leibniz's notation:

$$d(B_t)/dt = (B_n - B_{n-1}) \ast F_s$$

The derivative of impedance may provide additional information for helping to understand how quickly the impedance measurements are dropping, and therefore that a liquid reflux event may be occurring. It can also provide an indication if the impedance has reached a minimum or a maximum.

In another exemplary embodiment, the second derivative of the above $B_t$ function can be calculated to provide an indication of when the impedance has reached a minimum as opposed to a maximum. A shorter period to reach the lowest impedance measurement can better indicate a reflux event, or potentially signify a stronger or faster reflux event that may put the patient at risk of aspiration.

One exemplary way of calculating the second derivative of the function $B_t$ is via the following formula using Leibniz's notation:

$$d^2(B_t)/dt^2 = (B_n - 2*B_{n-1} + B_{n-2})*F_s^2$$

In an exemplary embodiment, the percent change in the impedance measurement is calculated to determine if there is a trend of impedance increasing or decreasing. One exemplary way of calculating the percent change of impedance is the following:

$$\frac{B_m - B_n}{B_n}$$

In this exemplary embodiment, factor n, denoting the beginning time period for calculating the summation, and the factor m, denoting the ending time period for calculating the summation, can be determined by a number of advantageous means. In one exemplary embodiment, the time period for n or m can be calculated based on when the sign changes in the percentage change calculation. In another exemplary embodiment, the factor m can be calculated based on the second derivative of the impedance measurement since the second derivative signifies when the impedance measurement has reached a local minimum. In another exemplary embodiment, the factor n, can be a fixed difference with factor m, where values of the impedance measurement at time n and m are compared. If a predefined threshold based on the difference of the impedance measurement at time n and m is exceeded, n is set as the starting period for the summation. For example, the difference between time n and m can be set as a fixed number such as (m−5) seconds. If the ratio of the resulting impedance measurement of time m over time n is 0.75, then time n and is set as the starting point for the summation.

After the change in impedance is calculated for each channel, this change data is then compared between all eight channels in step 1708. For example, the time interval for any changes in baseline impedance in one channel is compared to the time interval of baseline impedance changes in the other channels.

The change in the baseline impedance measurement for each channel is processed continually by algorithms to determine if the impedance change satisfies the definition for a condition such as liquid reflux, gas reflux (belching), a swallow, or any combination. If the algorithm determines the definition of a condition has been met, this information is then acted on a number of ways in step 1710, such as displayed on a monitor, signified as an alert, or processed in an algorithm to determine any further action.

B. Algorithms for Detecting Liquid Reflux

The use of impedance sensors to measure reflux has been well established by products used to diagnose Gastroesophageal Reflux Disease (GERD). The measurement principle for impedance sensors is when reflux passes over adjacent sensors the impedance measured between these two sensors decreases. Impedance data collected from two sensors is defined as a channel. Liquid reflux has been generally defined as a retrograde 50% drop in the measured impedance in at least two adjacent channels, as described by Zerbib, Frank et al, "Normal Values of Pharyngeal and Esophageal Twenty-four-Hour pH Impedance in Individuals on and off Therapy and Interobserver Reproducibility." *Clin Gastroenterol Hepatol*. 2013 April; 11(4):366-72, hereafter "Zerbib," which is hereby incorporated in its entirety herein by reference. This definition of reflux is based on relatively healthy patients being diagnosed for GERD. Zerbib also describes how only impedance drops lasting more than 3 seconds are counted.

An example liquid reflux episode is shown in FIG. 18. In this figure, the x-axis represents time and the y-axis represents the impedance measurements for each channel 1801-1806. In this exemplary embodiment, the six channels represent the eight impedance sensors 1101-1108. Specifically, channel 1 1801 represents the impedance measurement of impedance sensors 1101 and 1102. Similarly, channel 2 1802 represents the impedance measurement for sensors 1102 and 1103, channel 3 1803 represents sensors 1103 and 1104, channel 4 1804 represents sensors 1105 and 1106, channel 5 1805 represents sensors 1106 and 1107, and channel 6 1806 represents sensors 1107 and 1108. As the impedance is measured in channel 1 1801 at time one 1810 the impedance measurement starts to drop. The channel 1 1801 impedance measurement reaches a local minimum at time two 1812. If the difference in impedance between time one 1810 and time two 1812 is greater than 50% that can signify that reflux has been detected in channel 1 1801. A similar pattern of a drop in impedance measurement is seen in channels 2 1802, 3 1803 and 4 1804. Since the time of the impedance drop is delayed in each successive channel, it can signify that reflux is moving retrograde up the esophagus over time and is currently present in the location of channels 1 through 4, 1801-1804. In channel 1 1801 at time three 1814 the impedance measurement starts to increase. This increase continues to time four 1816, where the impedance measurement then levels off. This increase and leveling off of the impedance measurement can signify the reflux is no longer present in the location of Channel 1 1801. This increase in impedance measurement first started in channel 4 1804, and then successively in channels 3, 2 and 1 1803-1801. This signifies the reflux reached a maximum height in the location of Channel 4 1804 and then began to drop down in an antegrade motion through the locations of channels 3, 2 and 1 1803-1801. FIG. 18 illustrates a typical reflux event, where reflux is seen moving retrograde up the esophagus and then coming back down antegrade into the stomach.

While the same impedance measurement principles can be applied to measuring reflux in acute care patients, the algorithm may need to be adjusted to account for the unique parameters and condition of acute care patients.

For example, in an acute care setting the emphasis is on protecting the patient from the immediate threat of reflux potentially leading to aspirating gastric contents. This immediate threat is in contrast to the existing use of impedance measurement and algorithms to diagnose GERD, which is a non-real time analysis performed hours or days after collecting all the impedance data from the patient. Therefore, the measurements that trigger an alarm or suction event in an acute care setting may be a lower threshold to ensure the patient is safe. For example, in an exemplary embodiment, liquid reflux may be defined as a retrograde 30% drop in the measured impedance from a combination of two distal sensors compared to at least the next one or two proximal sensors. This definition may improve how potential reflux events are captured and processed in the algorithm.

This definition can also account for the fact that many acute care patients are taking acid suppression medication, such as proton pump inhibitors and H2 blockers. This acid suppression medication would result in a higher pH value overall in acute care patients. This higher pH liquid is typically not as conductive as the lower pH liquid, potentially resulting in a smaller impedance change. The level of impedance may also change over time given the changing material in the gastric environment. Different medicines, foods, and the changing condition of the acute care patient may also affect the impedance measurements.

A key difference in how existing impedance measurement systems work in identifying GERD is the data is analyzed off line usually hours or days after the reflux events have already occurred, and thus not processed in real time. Therefore, the current algorithms designed for GERD diagnosis are defined to identify the entire reflux episode, from the initiation of reflux until termination. The emphasis in a GERD diagnosis is to make sure the data is accurate in diagnosing a GERD condition, which will then drive decisions about medication usage, such as acid suppressants, and diet. In contrast, in the acute care setting the data needs to be processed in real time and decisions on whether to initiate an alarm or suction need to be made quickly in order to reduce the risk of aspiration. In the acute care setting, therefore, the emphasis is on determining if reflux has potentially been initiated in each channel, and not waiting to determine if it has terminated. These are key distinctions between modern impedance measuring systems and the proposed embodiment.

Given the importance of determining if reflux has been initiated, in an exemplary embodiment, it may be beneficial to use probability analysis to determine the relative probability that reflux has been initiated. For example, impedance measurements that indicate a larger impedance drop over time may be assigned a higher probability. This may be implemented on a graduated scale, such that the larger the impedance measurement drop, the higher the assigned probability. In contrast, a smaller impedance drop can be assigned a lower probability. This probability analysis can also account for the measurements of multiple sensors. For example, as shown in FIG. 18, if there is a progression of lower impedance measurements starting from the distal channels and continuing to the more proximal channels, the measurements from each channel can be assigned a higher probability since data from multiple channels reinforces the definition that a reflux event is occurring. In contrast, if only a proximal impedance channel were to suddenly show lower impedance measurements with no other neighboring impedance channels showing reflux, the measurement can be assigned a lower probability.

C. Algorithms for Detecting Gas Reflux or Belching

The same apparatus and methods of use can also be used to detect reflux of a gas, often referred to as belching or burping. The proposed embodiment can discriminate air, or any belched gas, since it is a very poor conductor and thus typically causes an increase in impedance (e.g. from 4000 to 5500) versus the decrease in impedance caused by liquid (e.g. from 4000 to 2000) which is much more conductive. Traditionally, gas reflux is defined as a rapid (3 Kohm/s) increase in impedance >5 Kohm, occurring simultaneously in at least two impedance channels, as described in Zerbib. An example of gas reflux is showing in FIG. 19.

In this figure, the x-axis represents time and the y-axis represents the impedance measurements for each channel 1801-1806. In this exemplary embodiment, the six channels represent the eight impedance sensors 1101-1108. As the impedance is measured in channel 1 1801 at time one 1910 the impedance measurement increases very quickly. At time two 1912 the impedance measurement subsequently drops very quickly. The impedance measurement for channels 2 through 6 1802-1806 also increase and decrease at time one 1910 and time two 1912 respectively. This pattern can signify a belch event, since the impedance rises very quickly and simultaneously across each channel, representing gas from a belch moving retrograde quickly up the esophagus.

Detecting gas reflux in patients may be beneficial by allowing detection of those with gas forming bacteria in their stomach or small bowel. This can be an indicator of overgrowth with non-resident bacteria, which also causes other symptoms (e.g. bloating) and signs (e.g. diarrhea). Belching is a sign of feeding intolerance. Therefore, a patient that exhibits excessive belching may require different treatment by the clinician. Treatment can generally follow treatment for feeding intolerance, such as reducing tube feeds, raising the head of bed, administration of prokinetic agents, etc.

D. Algorithms for Detecting Swallows

The same apparatus for measuring reflux can also detect, record and report swallowing events. A swallow is an antegrade movement of a conductive material, e.g. saliva, food, drink, down the esophagus. Impedance measurement data of a typical swallow is shown in FIG. 20.

In this figure, the x-axis represents time and the y-axis represents the impedance measurements for each channel 1801-1806. In this exemplary embodiment, the six channels represent the eight impedance sensors 1101-1108. The impedance measurement in channel 6 1806 begins to drop at time one 2010. Since the first change in impedance measurement comes from the proximal channel 6, it signifies bolus material such as food or liquid is moving antegrade from the oropharynx and down the esophagus. The channel 6 1806 impedance measurement reaches a local minimum at time two 2012. If the difference in impedance between time one 2010 and time two 2012 is greater than 50% that can signify that bolus material has been detected in channel 6 1806. A similar pattern of a drop in impedance measurement is seen in channels five 1805, 4 1804, 3 1803, 2 1802 and 1 1801. Since the time of the impedance drop is delayed in each successive channel, it can signify that bolus material is moving antegrade down the esophagus over time and is successively present in all six channels 1801-1806. In channel 6 1806 at time three 2014 the impedance measurement starts to increase. This increase continues to time four 2016, where the impedance measurement then levels off. This increase and leveling off of the impedance measurement can signify the bolus material is no longer present in the location of Channel 6 1806. This increase in impedance measurement first started in channel 6 1806, and then successively in channels 5, 4, 3, 2 and 1 1805-1801. This signifies the bolus material progressed from Channel 6 1806 and dropped down in an antegrade and motion through the locations of channels 5, 4, 3, 2 and 1 1805-1801. FIG. 20 illustrates a typical bolus material swallow event, where bolus material is seen moving antegrade down the esophagus and into the stomach.

Understanding the frequency and pattern of swallowing can be helpful to clinicians. For example, it may be a sign that they are becoming more conscious. This can be important for patients who are sedated in an ICU where their level of sedation and consciousness needs to be monitored closely in order to titrate the administration of sedative drugs. If a patient requires paralysis, e.g. for life threatening hypoxemia, the frequency of swallows can also be used to titrate the administration of paralytic drugs, e.g. cisatricurium, rocuronium, with initiation of swallowing revealing a wearing off of the desired paralysis. In another example, a patient after a traumatic brain injury or after a severe stroke may be in a coma and also have impaired swallowing. Seeing a resumption of swallowing or increase in the frequency can be an important clue to clinicians that the patient is recovering neurologic function. In contrast, failure to resume such swallowing can be a potential sign that the brain injury is not improving.

E. Algorithms for Detecting Mixed Conditions

The algorithms need to account for scenarios where there are mixed conditions. For example, a patient that is swallowing may also be simultaneously refluxing gastric contents. An example of impedance measurements showing both swallowing and reflux is shown in FIG. 21.

In this figure, the x-axis represents time and the y-axis represents the impedance measurements for each channel 1801-1806. In this exemplary embodiment, the six channels represent the eight impedance sensors 1101-1108. The impedance measurement in channel 6 1806 begins to drop at time one 2110 and begins to level off at time three 2114. Since the first change in impedance measurement comes from the proximal channel 6, it signifies a swallow, i.e. bolus material is moving antegrade from the oropharynx and down the esophagus. At time two 2112, the impedance measured in channel 1 1801 starts to drop and then levels off at time four 2116. The change in channel 1 1801 signifies that reflux is present. Channels 5 1805 and 4 1804 also indicate a swallow event. Channels 2 1802 and 3 1803 indicate reflux is present. FIG. 21 illustrates a combination event where the swallow and reflux event occur at roughly the same time.

A swallow measurement can potentially mask a reflux event. Therefore, it is important to ensure that reflux is accurately assessed in these mixed conditions since the patient may be at risk for aspiration.

Another example of a mixed condition is a combination of liquid and gas reflux, or mixed reflux. This mixed reflux may be measured as gas reflux occurring immediately before or during a liquid reflux measurement. In an exemplary embodiment, additional algorithms can be created to correlate gas reflux with liquid reflux. For example, if there is a pattern where gas reflux occurs before liquid reflux, interventions can potentially be initiated before any liquid reflux is measured. Another exemplary embodiment is correlating swallows with liquid reflux. A lack of swallows measurements can indicate the patient is at a higher risk for aspiration. Therefore, interventions may be initiated earlier or more quickly, and based on alternative interpretations of potential reflux.

F. Algorithms for Smart Alarms

Alarms may be beneficial for warning of potential aspiration based on reflux and other measurements. The device can have an option for turning on one or more alarms. An alarm can be triggered, for example, for any reflux event. This, however, may lead to "alarm fatigue" in a patient with multiple small episodes of reflux. Therefore, it is desirable to allow customization of alarms based on the clinician's preferences with respect to a particular patient. For example, it may be desirable to set the threshold for triggering the alarm to be if any of the following conditions are met: 1) any reflux event of at least 10 cm in excursion/height, 2) the presence of at least 5 episodes of reflux less than 10 cm in height over a 6 hour period, 3) the continuous presence (at least 15 minutes) of a conductive material (likely liquid) spanning the sensors closest to the head, 4) a rapid rate of detecting an impedance drop in multiple channels.

Figure 15:
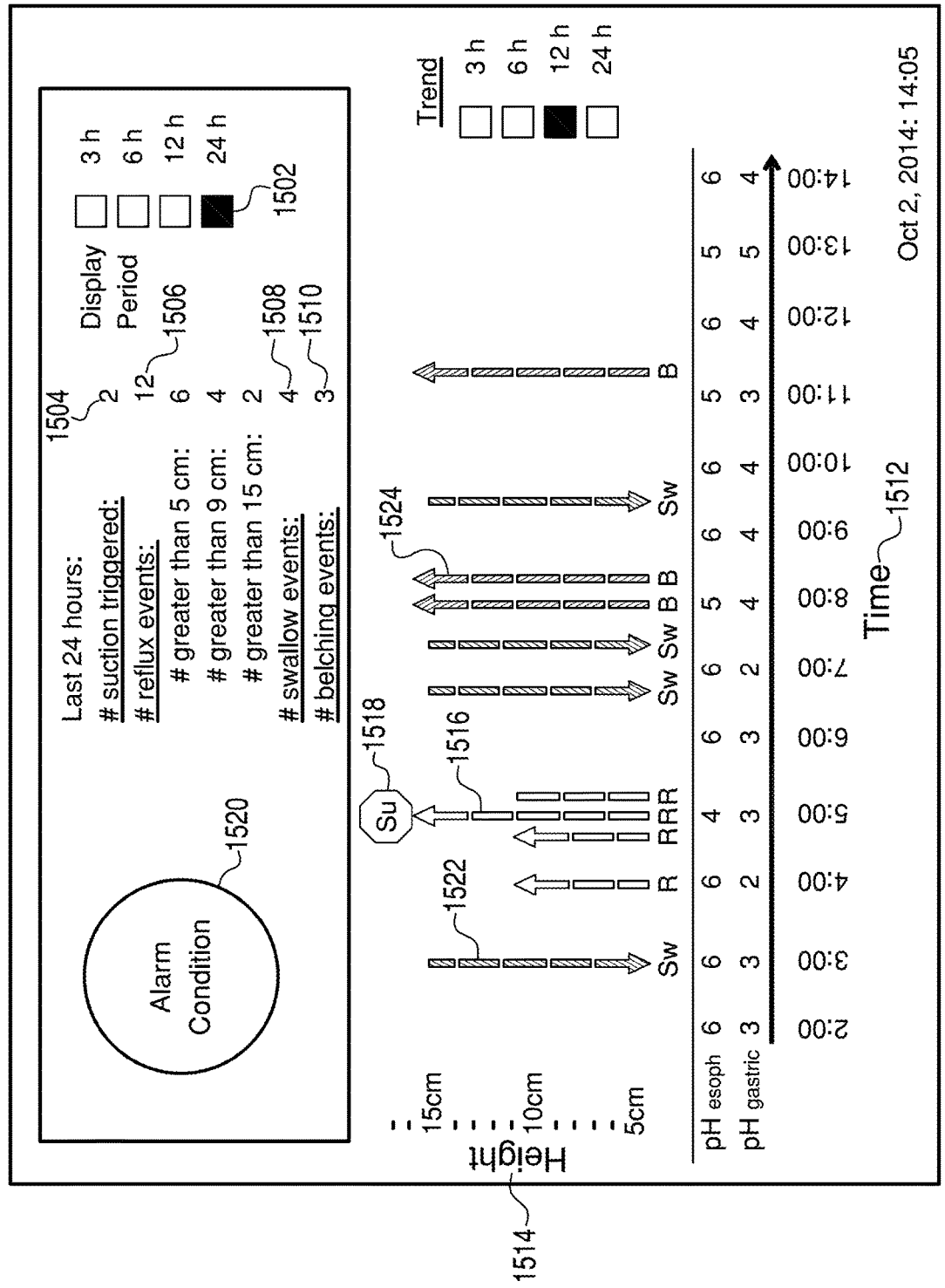
FIG. 15 is schematic of a user interface screen of the exemplary monitor of FIG. 11.

There can be an option for a visual alarm only, an audio alarm only, or a combination of a visual and audio alarm. The visual alarm can consist of a blinking red light that is part of the user interface, as shown in FIG. 15. There can be an option to allow customization of the sound level of the audio alarm. In addition, there can be an option to for different levels of alarm based on the nature of the reflux. For example, it may be desirable to have a visual alarm only for reflux events that may be of less concern, for example, less than 5 cm in height. However, if a reflux event between 10-15 cm in height is observed this can trigger the addition of the audible alarm. The system can also allow for escalation of the alarm volume, for example, if the "alarm silence" button is not enabled to show acknowledgement of the alarm state, the alarm volume can escalate over 5 minutes to the highest volume possible. The alarm state can also be transmitted, for example, wirelessly to a nurse's station, mobile phone, PC, feeding pump, modular patient monitor, or other device. In addition to use of reflux frequency and height, the alarm triggering threshold can also take into account data such as pH data, level of feeding, level of motility, plus specific data on the patient, i.e. medical condition, age, weight, etc.

V. Aspiration Prevention Interventions

There are several approaches to preventing aspiration in enterally fed patients, including "passive" and "active" systems.

A passive system may simply provide information to the clinician and solely relies on the clinician's response to this information to change the management of the patient. In one example, the feeding tube continuously records the presence of a conductive material (e.g. gastric contents) in the esophagus, and a pattern of retrograde bolus movement consistent with reflux of gastric contents is observed. These data are presented on the monitor. If the clinician is concerned about these data they can change the management of the patient. Some common responses include, but are not limited to, one or more of the following: 1) temporarily stop or reduce the rate/volume of tube feeds; 2) initiate administration of a prokinetic agent, e.g. erythromycin or metoclopramide, to enhance gastric emptying; 3) increase the elevation of the head of bed, e.g. from 30 to 45 degrees, in order to use gravity to minimize superior excursion of refluxed gastric contents; 4) switch feeding tube from gastric tube (naso- or oro-gastric) to a post-pyloric tube, ideally distal to the Ligament of Treitz; 5) manually suction out gastric contents.

After one or more of these interventions, the clinicians can determine if they have achieved a reduction in the frequency and/or superior excursion of refluxed gastric tube feeds. They can also determine if there is reduced bolus presence in the esophagus.

While there are many benefits to a passive system, in many clinical contexts there can be substantial incremental benefit from an active system. In addition to sharing the data collection features of the passive system, an active system has at least one automated intervention. This automated intervention has the benefit of being executed immediately once specific criteria have been met. In an exemplary embodiment, impedance data is captured and then analyzed via algorithms to determine if the specific criteria have been met. In one exemplary embodiment, the criterion is reflux detected at the highest impedance channel, signifying a higher probability of a potential aspiration event. In another exemplary embodiment, the criterion is the occurrence of reflux events at lower channels over a specific period, also potentially signifying a higher probability of a potential aspiration event. A number of exemplary data and criteria can be used to initiate an active process of intervention.

In one exemplary active system, once the criteria have been met the computer 110 may initiate processes (e.g., control appropriate pumps) so that gastric contents are automatically suctioned out of the stomach, which may assist in preventing gastric contents from being aspirated. In another exemplary active system, once the criteria have been met the feeding pump is automatically turned off by the computer so no additional feeds are introduced into the stomach, which may reduce any gastric contents from potentially being aspirated. In another exemplary active system, the computer may cause an obstruction to be automatically created in the esophagus, which may assist in preventing gastric contents from being aspirated.

A. Aspiration Prevention Via Suction of Gastric Contents

Applying suction to the feeding tube removes gastric contents and thus can potentially prevent or minimize subsequent aspiration since less material is present in the stomach and esophagus that can potentially be aspirated into the lungs. The general concept is an apparatus and system as shown in FIG. 11 that monitors reflux. When a certain frequency or superior excursion of reflux is measured or when there is a certain level of bolus presence in the esophagus, suction is transiently (e.g. 3 minutes) applied to the feeding tube to remove most or all of the gastric contents. In an exemplary embodiment, it may be desirable to set the threshold for triggering automatic suction to be if any of the following conditions are met: 1) any reflux event of at least 10 cm in excursion/height, 2) the presence of at least 5 episodes of reflux less than 10 cm in height over a 6 hour period, 3) the continuous presence (at least 15 minutes) of a conductive material (likely liquid) spanning the sensors closest to the head, 4) a rapid rate of detecting an impedance drop in multiple channels.

In an exemplary embodiment, the auto-suction product is comprised of a reflux detecting feeding tube, a connector for attaching the enteral feeding tube and suction tube, a monitor with auto-suction capability or control and containing a software component with customizable options to manage the process, as shown in FIG. 16.

In one exemplary embodiment, the feeding tube/impedance catheter has a dedicated suction lumen. For the apparatus containing a dedicated suction lumen, one lumen can be accessed for delivery of enteral feeds as well as medications, and the other lumen is connected to the monitor's suction device.

In an exemplary embodiment, there is a shared lumen such that no space within the tube is wasted on a lumen for suction that may never be needed. In a feeding tube with the shared lumen, an exemplary connector is attached to the proximal side of the feeding tube and has 2 connections or ports as shown in FIG. 14. One port connects to the enteral feeding tube where feeds are introduced, either bolus or via an infusion pump. The other port connects to a tube that is connected to a device which provides suction which can be provided by the monitor with a built-in suction capability, or it can be provided by standard hospital wall suction where the monitor exercises control of the suction.

During suction, one can envision automation of the feeding infusion pump to decrease or transiently stop infusion of tube feeds, however, this is not necessary, as a transient vacuum is more than adequate to reduce the stomach contents. Infusion rates of food are generally no more than 1.5 ml/min, therefore, even if feeding is not stopped there is minimal additional gastric contents achieved over the short run. In addition, there may be a benefit to not stopping tube feeds in patients who are at increased risk for hypoglycemia, e.g. patients on insulin who may become hypoglycemic if feeding is completely stopped.

The monitor's auto-suction system has several embodiments. In one embodiment, the monitor contains its own vacuum source, e.g. internal to the monitor. This must be able to generate 50 to 150 mm Hg negative pressure. In this embodiment, plastic tubing is connected from the "patient side" connector on the monitor to the suction port of the feeding tube connector. For ease of use this tubing can be connected to the feeding tube's electronic connecting apparatus and tubing used for infusing feeding, so only one apparatus contains up to 3 functional groups, i.e. wiring, feeding tubing, suction tubing. If the monitor detects specific triggering criteria, the vacuum system in turned on for a transient period, e.g. 3 minutes, in order to remove all or most of the gastric contents. An alarm can be triggered to notify the clinicians that such an intervention occurred. The system can automatically reset such that if it detects additional triggering criteria additional suction is applied. A lockout can be set such that if desired the apparatus must wait at least 15 minutes in between suctioning events, to minimize potential damage to the stomach's mucosa (lining).

In a preferred embodiment, the system relies on externally provided suction, e.g. the hospital's wall suction, as shown in FIG. 11. In this embodiment, the monitor controls a 2 way normally closed solenoid valve. In this embodiment, plastic tubing is connected from the hospital's routine wall suction regulator (reduces maximum pressure to approximately 150 mm Hg and allows for manual adjustment of suction pressure), passes through the monitor, and then connects to the suction port of the feeding tube connector, as shown in FIG. 14. For ease of use this tubing can be connected to the tube's electronic connecting apparatus and the tubing used for infusing feeding, so only one apparatus contains up to 3 functional groups, i.e. wiring, feeding tubing, suction tubing.

If the monitor detects specified triggering criteria, the solenoid valve is energized for a transient time (e.g. 3 minutes) resulting in it being opened such that the external vacuum source is connected with the tubing connected to the patients feeding tube, in order to remove all or most of the gastric contents. An alarm can be triggered to notify the clinicians that such an intervention was made. The system can automatically reset such that if it detects additional triggering criteria an additional suction is applied by reenergizing the solenoid valve. A lockout can be set such that if desired the apparatus must wait at least 15 minutes in between suctioning events.

Regardless of whether suction is internally or externally acquired, there is a need for a disposable suction trap as routinely employed during suction events. For example, the disposable suction trap can be located between the feeding tube connector 112 and the monitor 110.

The valve mechanism can be located in multiple places. For example, the valve for opening and closing suction can be located at the actual monitor. Another embodiment is to locate the valve at the head of the feeding tube. This can allow the feeding pump tube and the suction tube to be attached as-is to the feeding tube. In one exemplary embodiment, the valve can be connected via the wires that run back to the monitor and thus controlled via the monitor. In another exemplary embodiment, the control of the valve can be integrated directly into the valve assembly. In this embodiment, there may not be a physically separate monitor. The monitor functions are essentially integrated into the connector component. This includes functions such as monitoring the impedance measurements, controlling the valve for suction, initiating any alarms and managing settings.

There are a number of criteria for triggering suction. In one exemplary embodiment, a higher frequency of reflux events triggers suction regardless of the height of this reflux event, e.g. 1 event 5 cm in height may not trigger suction, however, 5 of these events over 30 minutes may trigger suction. In another exemplary embodiment, superior excursion of reflux, e.g. reaching 10 or 15 cm, triggers suction, even if there is only 1 such event. Alternatively, a single event of reflux rising to above the carina can trigger the suction. The rate of detecting reflux in each channel can also trigger suction. For example, suction can be initiated when reflux is detected in each successive channel at a fast rate, such as one channel per second (2 cm/s) starting in the distal channels. This fast rate of detected reflux can signify aspiration may occur imminently and thus the patient is at a higher risk. The size of the reflux, or bolus, can also be a trigger for suction. For example, a bolus spanning two channels, therefore 4 cm, can trigger suction if measured in the more proximal channels that are closer to the tracheal opening 107. This may also be customized based on patient factors. For example, in another exemplary embodiment, in a patient who is 3 days postoperatively from a lung transplant it may be desirable to suction tube feeds if any reflux is detected, e.g. only one 5 cm high event. In another exemplary embodiment, the monitor may compute a risk factor based many inputs such as the number of refluxes within a time period, the extent of those refluxes, the rate of the retrograde motion of the reflux, the number of swallows within a time period, the number of belches in a time period, etc. For example, each reflux may be assigned a numerical severity based on its extent, rate of retrograde motion, and volume of the reflux. The risk factor may be computed from these severities with a sliding weight function. This weight function may place the most weight on the severity of the most recent refluxes with a decreasing weight given to the severity of refluxes which happened earlier. The risk factor may be computed as the sum of the weighted severities of each of the refluxes. The suction may be initiated if the risk factor was above a certain threshold. The weighing and severity functions may be designed to produce a risk factor above a default threshold for a rapid and extensive reflux happening in real time. Other events such as swallows or even suction may be assigned a negative severity and consequently reduce the risk factor. The clinician may be able to view this risk factor displayed on the monitor. The embodiments of the display risk factor include but are not limited to text, a colored indicator, the risk factor plotted with respect to time, and a bar graph.

Suction is routinely applied to gastric tubes, typically either as continuous low suction (e.g. 30-50 mm Hg) or intermittent high suction (e.g. 150 mm Hg). There is generally a desire to minimize continuous suctioning with high suction in order to avoid damage to the gastric mucosa (i.e. stomach lining). Therefore, a default setting may call for 3 minutes of suctioning, however, this can be changed based on clinician desire. In addition, the suctioning duration can escalate based on recorded data. For example, if reflux is still very active after 3 minutes of suctioning, the monitor (in addition to alarming and alerting the caregiver) can apply constant suction (up to a maximum of 30 minutes) until the reflux abates. In addition, it may be possible for the monitor to vary the suction strength. For example, for the monitor with the internal vacuum source, it is possible to customize the system such that upon less concerning reflux (e.g. 3 events×5 cm in height over 1 hour) 3 minutes of low vacuum pressure (e.g. 50 mm Hg) is applied, however if there is very concerning reflux (e.g. 2 events×15 cm in height) then full strength suction (e.g. 150 mm Hg) is applied. Similarly, in the case where the monitor is controlling suction, an exemplary valve can open up part way to initiate low vacuum pressure (e.g. 50 mm Hg), but be open fully to initiate full strength vacuum pressure (e.g. 150 mm Hg). In other exemplary embodiments there can be variations of this transition from low vacuum pressure to full strength vacuum pressure. For example for the first minute the monitor can initiate full strength vacuum pressure but then lower it to low vacuum pressure for the remaining two minutes. In another exemplary embodiment, the monitor can initiate full strength vacuum pressure until the level of reflux has declined to a sufficient point.

To help the clinician understand the suction events, there can also be the option for a report that tells the clinician how many suctioning interventions were triggered in a time period, e.g. 6 or 24 hours. This report can contain detailed information about the measurements before, during, and after the suction event.

In such a setting where reflux of gastric contents is monitored and either passive or active interventions can be triggered there may be no need for routine, manual measurements of Gastric Residual Volume (GRV). This can reduce the workload of nurses since measurement of GRV is a time consuming task. It is done to try to identify patients at higher risk for reflux and aspiration since currently there is no way of detecting if patients are exhibiting reflux.

In an exemplary embodiment, the algorithm may be adjusted to reflect how the head of bed angle affects the measurement of reflux and the potential risk of aspiration. A lower head of bed angle is common in acute care patients. The guidelines recommend a head of bed angle of at least 30° for acute care patients. Often these patients slide down in their beds for an effective angle of less than 30°. Many patients are not monitored that closely, so the effective angle of the patient is quite often less than 30°. The specific sensor location of any measured reflux and the length of time the patient is refluxing can affect when to initiate suction. In an exemplary embodiment, a lower proximal location of reflux and a shorter length of time refluxing may be utilized to initiate auto suction given patients are often at a lower effective head of bed angle and may more easily reflux and aspirate gastric contents. For example, reflux measured at a sensor location of 5 cm, which is approximately 5 cm above the LES, is may be specified to initiate suction. In another example, reflux measured for a period of five minutes at a location of 5 cm above the LES may be specified to initiate suction.

The ability to detect reflux and suction gastric contents can even enable a lower head of bed than is now routinely prescribed due in the absence of these useful tools. This lower head of bed may enable a number of benefits. In some patients with head injuries, it is beneficial to have a lower head of bed angle to assist in the recovery of the patient. It may also be feasible that a lower head of bed angle can help prevent subglottic secretions that contain oropharyngeal bacteria from colonizing the trachea 107 and raising the risk of aspiration pneumonia. In each case, the suction capability of the product can reduce the patient's risk of aspirating gastric contents and potentially developing aspiration pneumonia.

Acute care patients with a feeding tube may be more susceptible to reflux since the feeding tube passes through the LES and therefore can sometimes compromise the effectiveness of the LES in preventing gastric contents from entering the esophagus. Therefore, reflux may be detected in the distal channels, such as 5 cm above the LES, more frequently. In an exemplary embodiment, suction may only be initiated if reflux reaches the higher proximal channels, since reflux may be more common at the lower distal channels.

B. Aspiration Prevention Via Adjustment of Feeding Pump

Data provided by the impedance sensors may be used to adjust feeding levels. For example, if the patient is experiencing reflux past a predetermined level, the feeding pump may be instructed to decrease the level of feeding, e.g. from 80 ml/hr to 40 ml/hr. This decrease in feeding may allow the patient to further digest the nutrition, and may prevent a more severe episode(s) of reflux from occurring that would increase the risk for aspiration. In this example, the smart feeding tube is connected to a feeding pump, enabling a direct connection to capture and process impedance data and then make changes to the delivery of nutrition. An alarm may also be added to the device to communicate to clinicians of any reflux events and when the feeding level has been reduced.

Many clinicians initiate nutrition at a very low rate given the fear of reflux and aspiration of gastric contents. Such a system as described above can enable clinicians to initiate feeding at a higher rate and with more confidence, knowing that if any clinically significant reflux is detected, the feeding rate can be automatically decreased and/or the gastric contents automatically removed via suction. This can enable acute care patients to receive more nutrition, and therefore recover more quickly and effectively while also being protected from potential aspiration of gastric contents.

C. Aspiration Prevention Via Esophageal Obstruction

Another exemplary embodiment prevents aspiration by automatically initiating an obstruction in the esophagus in response to the impedance sensor data that can prevent gastric contents from traveling up the esophagus to the trachea's opening 107. A balloon device may be located somewhere between the LES and trachea 107, automatically inflate based on the sensor data. If the level of reflux measured by the sensors 1101-1108 is high enough to indicate that the patient is at risk of aspiration, the monitor may control a pump to pump air into the balloon and inflate the balloon. The inflated balloon creates a barrier in the esophagus 101 that prevents the reflux from getting to the trachea 107 and potentially entering the lungs. This same approach may also be used to prevent vomiting upon detection of a risk of vomiting by the monitor. The balloon mechanism should inflate quickly enough to block any reflux. The algorithm for determining when to inflate can correspond with the speed of inflation. The materials of the balloon and level of inflation are designed to accomplish the goal yet not injure the esophagus 101. After inflating, the balloon can ideally be used again. The monitor can show information about the balloon being deployed. An alarm may also be triggered to warn clinicians when such a severe reflux or vomit event occurs so they can potentially attend to the patient. As the balloon is inflated, the gastric contents may automatically be removed via suction as discussed elsewhere herein.

It should be emphasized that the embodiments disclosed herein are not mutually exclusive but are useable with one another, in whole or in part—it is impracticable to set forth a separate description to for each possible combination of features of the embodiments described herein, and thus a particular combination of features according to the invention may be described in connection with separate embodiments in this disclosure. Some embodiments utilize sensors to assist the clinician place the feeding tube correctly in the patient. Such embodiments may reduce time and expense to confirm the placement (e.g., via an X-ray). These embodiments may allow clinicians to insert feeding tubes and provide timely feedback to indicate that the insertion is correctly placed, or progressing correctly or that the feeding tube is not in a correct location, such as the lumen of the trachea or a bronchus. Some embodiments provide feedback to indicate that enteral nutrition is being tolerated, or, as appropriate, warning the clinician that enteral nutrition is not being tolerated. Gastric residual volume may be automatically measured via a sensor, which may ease the burden on clinicians in connection with manual measurements or other labor intensive measurements. Some embodiments assess gastric motility, a clinical read-out that can help clinicians determine if patients are tolerating enteral nutrition. According to other embodiments, reflux in the esophagus may be monitored, providing both a warning to clinicians and an automatic suction capability to remove the gastric contents and the risk of aspiration. While example embodiments have been particularly shown and described, it will be understood by one of ordinary skill in the art that variations in form and detail may be made therein without departing from the spirit and scope of the attached claims.

VI Impedance Based Local GRV Estimation

In an exemplary embodiment, a sensor located at the distal end of the feeding tube is used to measure GRV. The GRV sensor may be composed of two or more electrodes. When these electrodes are placed in the patient's stomach, they measure the impedance of nearby tissue and fluids. This impedance measure will depend on the conductivity and distribution of the tissues and fluids surrounding the electrodes. Since the gastric chyme typically has a high conductivity relative to the stomach or other surrounding tissue, as the volume of the stomach increases due to an increase in gastric chyme, the impedance measured by these electrodes will decrease. This decrease in impedance may occur due to the creation of a larger path width between the electrodes created by the gastric chyme. If the GRV sensor is composed of just two electrodes, this will be referred to as a bipolar impedance sensor/measurement. With two electrodes, impedance may be measured by injecting a current between the two electrodes and simultaneously measuring the resulting voltage on the same two electrodes. These two electrodes simultaneously work as both the current source electrodes and the voltage sensing electrodes. If the GRV sensor is composed of three electrodes, this will be referred to as a tripolar impedance sensor/measurement. With three electrodes, impedance may be measured by injecting a current between a common electrode and a source electrode. The voltage is then measured between a sensing electrode and the common electrode. The common electrode functions as both a source electrode and a sensing electrode simultaneously. If the GRV sensor is composed of four electrodes, this will be referred to as a tetrapolar impedance sensor/ measurement. With four electrodes, impedance may be measured by injecting a current between two source electrodes and the voltage may be measured between two sensing electrodes. In some embodiments, impedance may also be measured by applying a voltage to the source electrodes and measuring the resulting current on the sensing electrodes in bipolar, tripolar, and tetrapolar impedance measurement configurations. Two or more electrodes may be ganged together to form a single electrode. For example, two or more electrodes on a conductivity sensor may function as a single electrode for the GRV sensor by electrically connecting these electrodes, such as outside the patient, such as within the monitor.

In an exemplary embodiment, a conductivity sensor may also be located at the distal end of the feeding tube along with the GRV sensor. The conductivity sensor can be utilized to determine the conductivity (inverse of resistivity) of the gastric contents. The conductivity sensor functions in the much the same way as an impedance sensor, but it is intended to only measure the intrinsic property of electrical conduction of a relatively well-known volume of tissue or liquid. By contrast, the impedance measurement of the GRV sensor is a reading of the extrinsic property of electrical conduction of a volume of liquids and tissues whose conductivity and distribution is unknown. Similar to the GRV sensor, the conductivity sensor may be composed of two, three, or four electrodes. If the conductivity sensor is composed of just two electrodes, this will be referred to as a bipolar conductivity sensor/measurement. With two electrodes, conductivity may be measured by injecting a current between the two electrodes and simultaneously measuring the resulting voltage on the same two electrodes. These two electrodes work as both the current source electrodes and the voltage sensing electrodes. If the conductivity sensor is composed of three electrodes, this will be referred to as a tripolar conductivity sensor/measurement. With three electrodes, conductivity may be measured by injecting a current between a common electrode and a source electrode. The voltage is then measured between a sensing electrode and the common electrode. The common electrode functions as both a source electrode and a sensing electrode simultaneously. If the conductivity sensor is composed of four electrodes, this will be referred to as a tetrapolar conductivity sensor/measurement. With four electrodes, conductivity may be measured by injecting a current between two source electrodes and the voltage may be measured between two sensing electrodes. In some embodiments, conductivity may be also be measured by applying a voltage to the source electrodes and measuring the resulting current on the sensing electrodes in bipolar, tripolar, and tetrapolar conductivity measurement configurations.

Figure 22A:
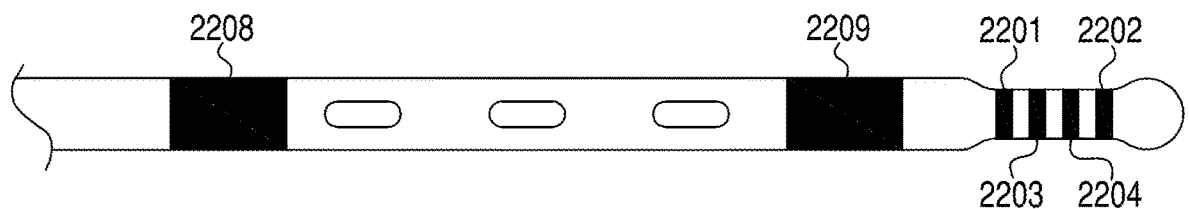
FIGS. 22A-22E are schematics of an apparatus for measuring impedance and conductivity in accordance with exemplary embodiments.
Figure 22B:
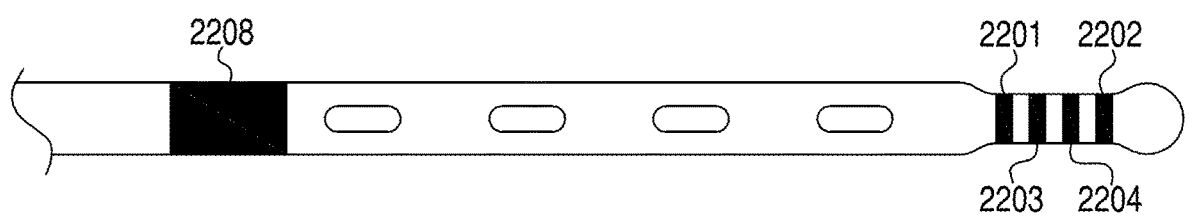
Figure 22C:
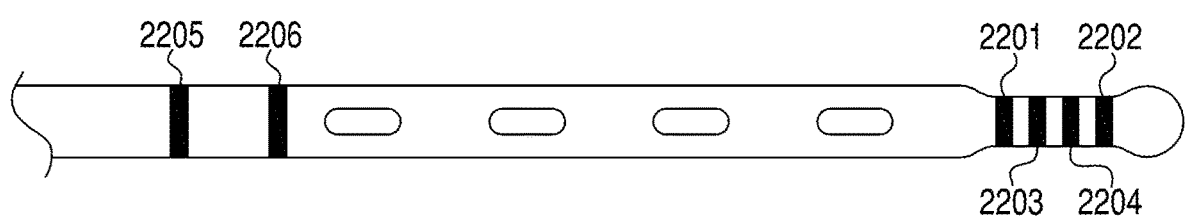
Figure 22D:
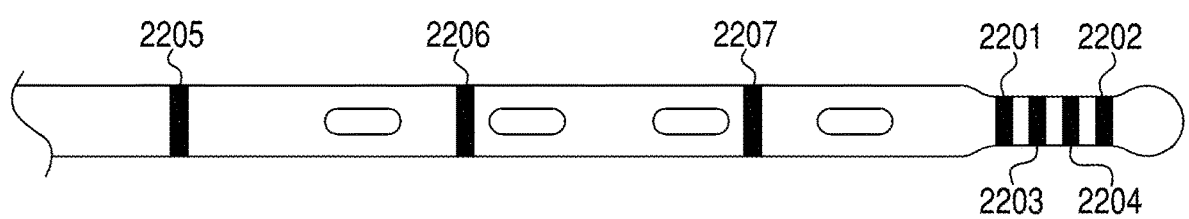
Figure 22E:
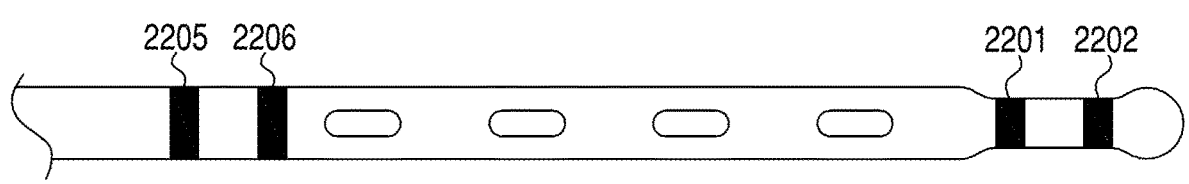

FIG. 22A shows an exemplary embodiment of a tetrapolar conductivity sensor at the distal end of the feeding tube 102. It is composed of source electrodes, 2201 and 2202, and two sensing electrodes, 2203 and 2204. Electrodes 2201 and 2202 may also be used in bipolar conductivity measurement configurations to simultaneously inject current and sense voltage as shown in FIG. 22E. This conductivity measurement can be helpful for estimation of GRV, since the estimation of GRV using measurements of epigastric impedance (see FIG. 10) depends on conductivity of the gastric contents and the other structures (e.g., skin, muscle tissue, adipose tissue) and their volumes in the epigastric region being interrogated by the GRV sensor's impedance measurement electrodes. The stomach contains relatively conductive material and when GRV increases, the measured impedance decreases. An increase in the conductivity of the gastric contents will also cause a drop in the measured impedance. By measuring the conductivity, this confounding impedance variable can be factored out from the estimation of GRV. By extension, the measurement of GRV via impedance depends on a difference in impedance of the gastric contents and these other structures. If the ionic strength of the tube feeding formula is too low, then the difference in impedance between the gastric contents and the other structures in the epigastric region of interest will be insufficient to provide a reliable signal for estimating GRV. In the research laboratory, this problem can be solved in a simple way by adding a large quantity (e.g., 9 g/L; 154 mEq/L) of sodium chloride (NaCl; table salt) to the standard tube feeding formula to ensure that the ionic strength of the tube feeding formula is sufficient to provide a good impedance signal for estimation of GRV. In the clinical setting, however, it would be ill-advised to add large quantities of sodium chloride to the tube feeding formulas that are administered to patients, since many patients cannot tolerate large loads of either sodium ion (Na+) or chloride ion (Cl−). Some commercial tube feeding formulas contain high concentrations of Na+ and potassium ions (K+), and therefore have sufficient ionic strength to permit reliable estimates of GRV, using the epigastric impedance methodology. One such formula is Osmolite 1.2, which contains 58 mEq/L of Na+ and 46 mEq/L of K+. Other commercial tube feeding formulas contain relatively low concentrations of Na+ and K+, and therefore may not have enough ionic strength to permit reliable estimates of GRV, using the epigastric impedance methodology. An example of this type of tube feeding formula is Nutrihep, which contains 7 mEq/L of Na+ and 33 mEq/L of K+. The ionic strength (and, hence, the conductivity) of the gastric contents is determined not only by the ionic composition of the tube feeding formula, but also by the secretion of ions (H+, K+, Cl−) by the gastric mucosa into the lumen of the stomach. Thus, in order to determine whether the contents of stomach at any given point in time have a composition that is suitable for determination of GRV, it may be desirable to continuously monitor the conductivity of the gastric contents. Moreover, since calibration of the epigastric impedance monitoring system (by injecting into the stomach a known volume of tube feeding formula) will be done only intermittently and the rate and composition of gastric secretion of ions can change on a minute to minute basis, it may be useful to adjust the GRV calibration settings continuously by taking into consideration measured changes (relative to the value measured at the time of calibration) of the conductivity of the gastric contents.

In an exemplary embodiment, the calculation of impedance is based on the following exemplary equation according to Jaakko Malmivuo & Robert Plonsey, "Bioelectromagnetism—Principles and Applications of Bioelectric and Biomagnetic Fields", Oxford University Press, New York, 1995, 25.3.3, hereafter "Malmivuo" which is incorporated in its entirety herein by reference.

$$Z = \frac{Z_t Z_s}{Z_t + Z_s}$$

In the above exemplary equation, there is an assumption that the tissue outside the stomach and the stomach are essentially parallel resistors. In an exemplary embodiment, there is an assumption that the impedance of the surrounding tissue ($Z_t$) is constant.

In this exemplary embodiment, the impedance of the stomach ($Z_s$) varies as a function of its conductivity ($\sigma$), length ($l$) and cross-sectional area ($A_s$), which is perpendicular to the flow of current. In this exemplary embodiment, there can be an assumption that the length is the distance between our electrodes, which is known. In this exemplary embodiment, an exemplary equation for the impedance of the stomach, $Z_s$, can be the following:

$$Z_s = \frac{l}{A_s \sigma}$$

Combining these equations results in the following exemplary equation for measuring impedance:

$$Z = \frac{Z_t \ell}{A_s \sigma Z_t + \ell}$$

In this exemplary equation, the measured impedance varies with the area, length, and conductivity of the stomach. In this exemplary embodiment, there is an assumption that the impedance of the tissue is constant and the length is known. By accounting for the changes in the measured impedance that are from the changes in conductivity, we can use this exemplary model to calculate changes in the stomach's area.

FIG. 22A shows an exemplary embodiment of a GRV sensor composed of two electrodes, 2208 and 2209, in a bipolar impedance measurement configuration. The electrodes of the conductivity sensor may also be ganged together form a single electrode for the GRV sensor. In this case, FIG. 22A shows a GRV sensor composed of three electrodes, 2201-2204, 2208, and 2209, in a tripolar impedance measurement configuration. FIG. 22B shows an exemplary embodiment of a GRV sensor composed of two electrodes in a bipolar impedance measurement configuration. The electrodes of the conductivity sensor be ganged together form a single electrode for the GRV sensor. FIG. 22C shows an exemplary embodiment of a GRV sensor composed of two source electrodes, 2202 and 2205, and two sense electrodes, 2206 and 2201, in a tetrapolar impedance measurement configuration. FIG. 22D shows an exemplary embodiment of a tetrapolar impedance measurement configuration. The four electrodes of the conductivity sensor, 2201-2204, are ganged together to form one source electrode for the GRV sensor. The other source electrode is 2205. The sense electrodes in FIG. 22D are 2206 and 2207. FIG. 22E shows an embodiment of a GRV sensor composed of four electrodes in a tetrapolar impedance measurement configuration. The conductivity sensor in this embodiment is composed of just two electrodes, 2201 and 2202, to simultaneously inject current and sense voltage forming a bipolar conductivity measurement configuration. For measuring GRV, the source electrodes are 2205 and 2202 and the sense electrodes are 2206 and 2201. These embodiments are only examples and are not intended to limit the scope of this invention. Many other embodiments of electrodes forming a GRV sensor and a conductivity sensor are possible with or without shared electrodes and in bipolar, tripolar, or tetrapolar modes.

Figure 23:
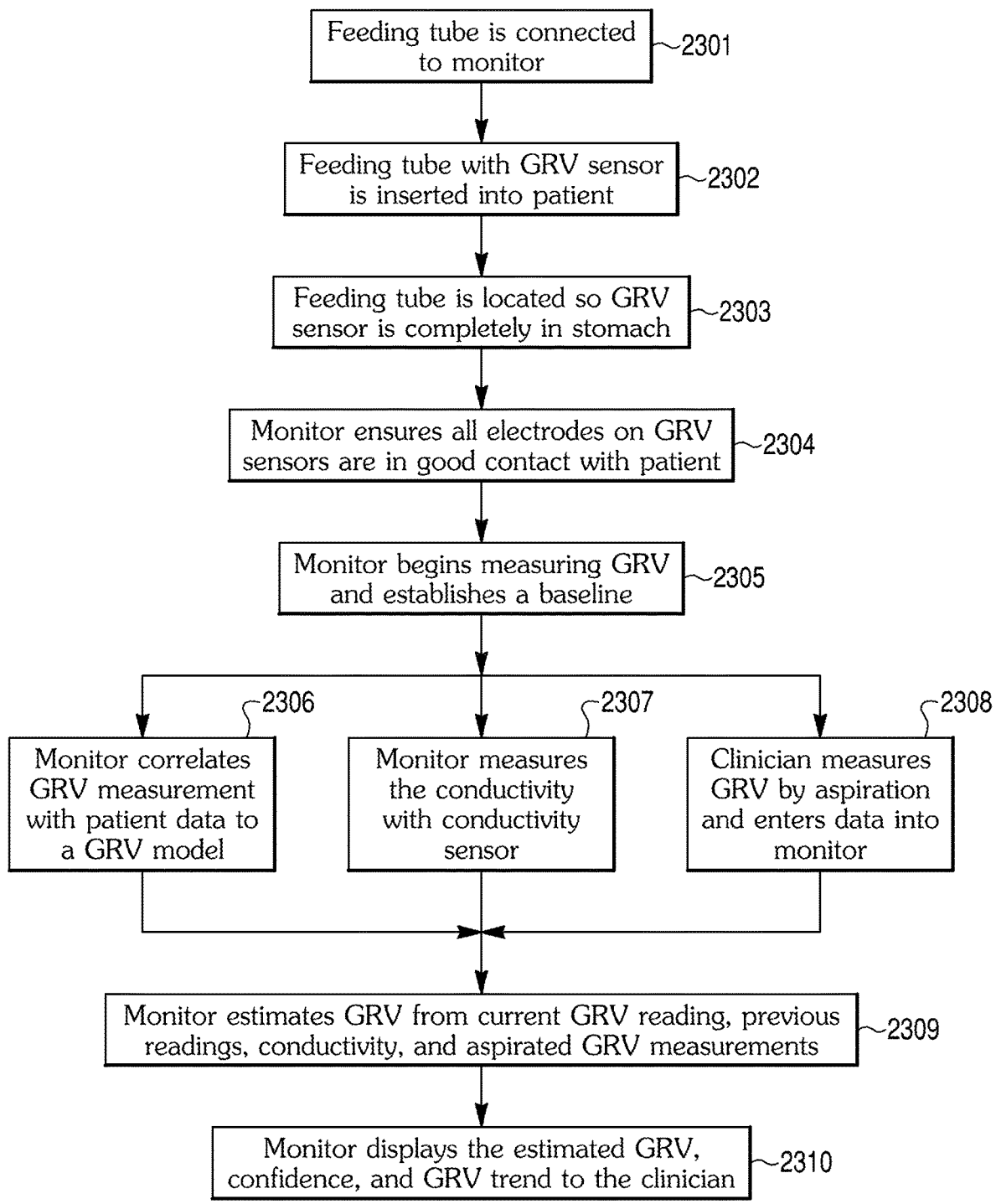
FIG. 23 is a flowchart of an exemplary method and apparatus for measuring GRV

An exemplary process for utilizing the apparatus described in FIG. 22 is described in FIG. 23. In the first step of this exemplary process 2301, the clinician connects the feeding tube 102 to the monitor 110. In step 2302, the clinician inserts the feeding tube. In step 2303, the clinician locates the feeding tube such that the GRV sensor is located in the patient's stomach. In step 2304, the monitor performs a test to ensure that the electrodes of the GRV and conductivity sensor are in good contact with the patient, either by touching tissue, being immersed in conductive fluid like gastric chyme, or a combination of both. In step 2305, the monitor begins taking GRV measurements to establish a baseline measurement. In step 2306, this baseline measurement can be compared to models to estimate the patient's GRV. The model may accept the patient's information such as sex, age, weight, height, etc. to help make the impedance measurement from the GRV sensor more accurate. In step 2307, the monitor takes a conductivity measurement with the conductivity sensor at the distal tip of the feeding tube. Since the distal tip of feeding tube should be immersed in gastric chyme, the conductivity measurement should reflect just the intrinsic electrical conductivity of the chyme. In step 2308, the clinician measures GRV by aspiration and enters this into the monitor. The clinician may have measured the GRV by aspiration prior to inserting this instrumented feeding tube. In this case, the clinician may enter the time and date that the aspirated GRV measurement was taken. Alternatively, the monitor may be able to get this data by data exchange with electronic medical records. In step 2309, the monitor estimates the GRV from model data, the conductivity readings, and previous GRV measurement (aspirated GRV measurements or previous reading made by the monitor). Finally, in step 2310, the monitor displays the live GRV measurement to clinician. In addition to the live GRV estimate, the monitor may also display the monitor's confidence in the live GRV measurement and a trend of the previous GRV readings.

In an exemplary embodiment, conductivity can be a useful indicator for estimating GRV. In this embodiment, gastric residual volume is determined by measuring the conductivity of gastric contents before and after an injection of a control bolus. In this embodiment, a conductivity sensor is located on the distal tip of the feeding tube. Such a conductivity sensor may be composed of two or more electrodes that can be connected via wires to the monitor. The monitor 110 can take continuous conductivity measurements of the gastric contents. In this embodiment, a combination of multiple sensors can be used, such as those sensors disclosed herein and other sensors, and such combinations should be considered within the scope of the various embodiments described herein. The monitor can then control a known amount of fluid to be introduced through the feeding tube and into the stomach, which in an exemplary embodiment can be 50 mL of distilled water. Utilizing water as a control can be advantageous, since acute care patients require hydration and water is a safe substance. The conductivity sensor can then continually measure the change in conductivity of the gastric contents after introducing this control bolus of distilled water.

VII. Tube Localization Through Impedance Measurements

An exemplary embodiment for determining feeding tube location is to measure the impedance between one or more impedance sensors on the feeding tube and a reference sensor. The impedance sensors on the feeding tube 102 may be electrodes. The reference sensor may be an electrode patch adhered to the skin of the patient about 4 fingerbreadths (about 4-5 cm) to left of the umbilicus. In this exemplary embodiment, there are two or more source patches attached to the skin of the patient between which an alternating current is driven. For example, one source patch may be placed on the right side of the patient's neck and the other can be placed 1 cm to the left of the reference sensor. These source patches may be electrodes adhered to the skin of the patient. The impedance sensors on the feeding tube, the reference sensor, and the source patches are connected to the monitor. As the feeding tube is inserted down the patient's esophagus, the distance between impedance sensors on the feeding tube and the reference sensor decreases which causes the measured impedance to also decrease. The impedance between each impedance sensor on the feeding tube and the reference sensor is measured in Ohms by the monitor. Each of these measured impedances may be referred to as a location channel.

The distances between all the impedance sensors on the feeding tube is known. Differences between the each of these location channels can be related to the known distances between the impedance sensors. For example, a calibration factor can be computed for each location within the body and between each pair of two different impedance sensors by dividing the measured difference between two location channels in Ohms by the distance in centimeter between the impedance sensors associated with the two location channels. The calibration factor may change because of the anatomical structures around it. When two impedance sensors are in an area with relatively low resistivity, they will have a low difference in their location channels. Similarly, when two impedance sensors are in an area with relatively high resistivity, they will have a higher difference in their location channels. As an example, there may be highly resistive gas in the patient's stomach. When two electrodes pass into this gas the calibration factor between these two electrodes will increase.

The impedance between the impedance sensors on the feeding tube and the reference sensor may change because of respiration, the patient's heart, beating, or other physiological processes. In this exemplary embodiment, the location channels are filtered and contain only frequencies below the heart and breathing rate of the patient. The amount that the respiratory and cardiac rhythms impact the location channels may also be used to indicate location. While the impedance sensors on the feeding tube are near the heart and lungs, the amplitude of the changes in the location channels which result from the heart and lungs will be high. Near the diaphragm or within the stomach, the changes in the location channels which result from the heart and lungs will be lower. As the clinician inserts the tubes from nose, into esophagus, and into the stomach they will see the amplitudes of cardiac and respiratory artifacts rise and fall. If they fail to see this characteristic pattern, it may indicate the feeding tube is not in the esophagus but rather in the lower respiratory tract.

The location of the impedance sensor in the patient's body may be monitored consistently by monitor 110. This location information may be used to detect if the feeding tube is moving throughout time. The feeding tube may move up into the esophagus or move too low in the stomach or past the pyloric sphincter. An alarm may sound to detect if the feeding tube has moved outside of a preset range. This would indicate to a clinician that the position of the feeding tube may need to be adjusted to return it to an appropriate location.

Figure 24:
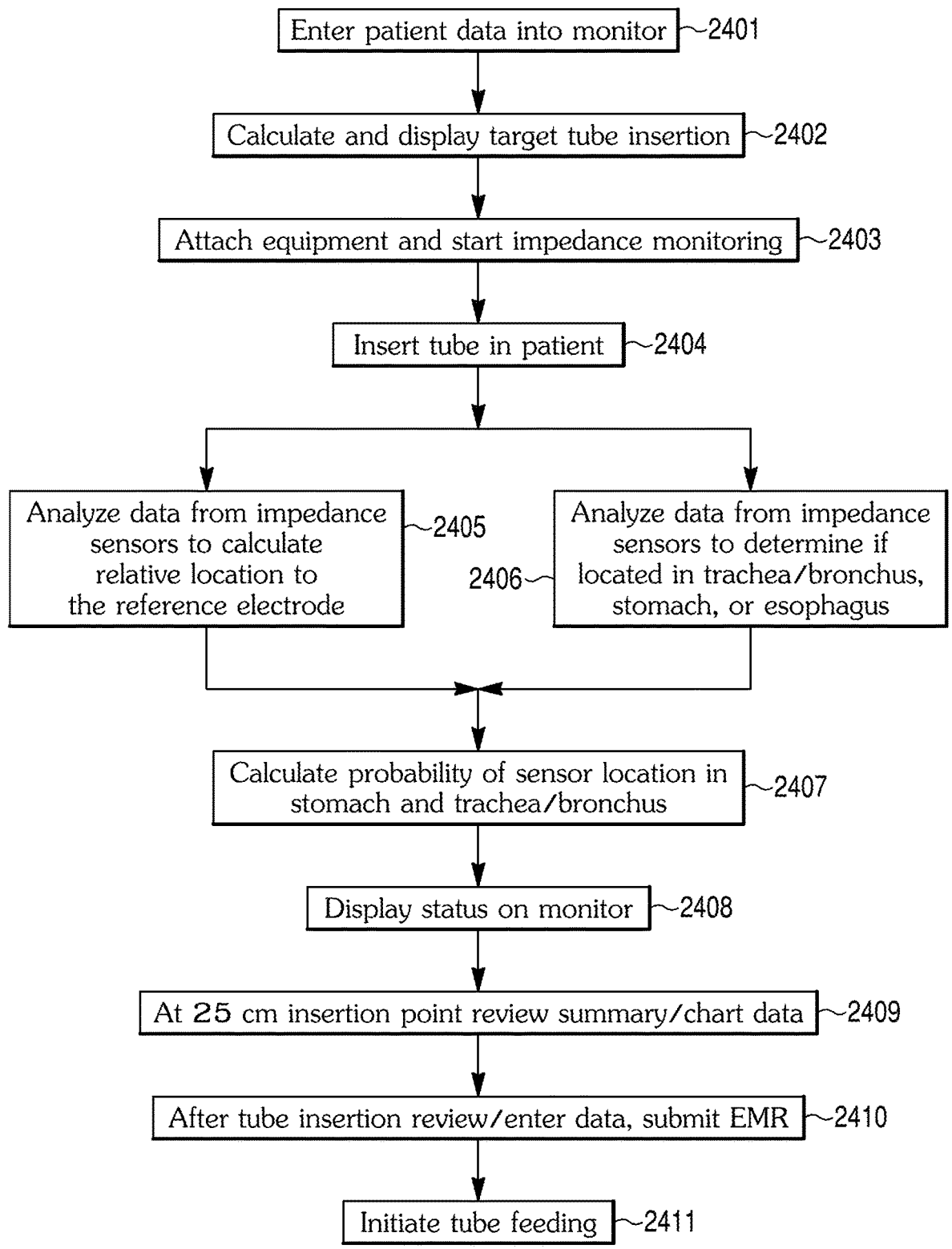
FIG. 24 is a flowchart of an exemplary method and apparatus for determining the location a feeding tube via impedance measurements

An exemplary process for utilizing the apparatus described is provided in FIG. 24. In step 2401, patient data, including but not limited to name, ID number, sex, height, and weight can be entered into the monitor manually or through an electronic data interchange. In step 2402, the target distance for tube insertion can be calculated. For example, the nomogram proposed by Cirgin Ellett may be utilized to calculate the target distance from the patient data entered. In step 2403, the source patches and reference sensors are attached to the patient's skin. The feeding tube 102 is inserted partially into the patient in step 2404. In step 2405, the monitor analyzes the location channel from each of the impedance sensors on the feeding tube and computes a calibration factor. This calibration factor is used to convert the location channels into units of distance, such as centimeters. In step 2406, the monitor uses the conversion factors and respiratory artifacts to determine its location relative the lungs, heart, LES, stomach, etc. In step 2407, the monitor calculates a probability that the feeding tube is in the lower respiratory track or the stomach from the location channel data, conversion factors, respiratory artifacts, and cardiac artifacts. In step 2408, the current status of the feeding tube is displayed to the clinician. Step 2409 is reached when the clinician has inserted the feeding tube a certain distance. This distance may be computed as from the patient data input in step 2401, it may be based on the already computed target distance from step 2402, or it may be a fixed distance. In one exemplary process, this distance is 25 cm. In step 2409, the monitor presents a report which contains summaries or charts of the tube insertion progress. The information in the report may include each a numerical read out of the location channels, the calibration factors, the respiratory artifacts, and the cardiac artifacts. Each of these variables may be plotted against time and displayed in a chart. Likewise, the monitor may compute an estimated location from all these variables. The calibration factors, the respiratory artifacts, and the cardiac artifacts may further be plotted on a chart with respect to the estimated distance. Step 2410 is reached once the targeted insertion is reached. Either automatically or at the prompt of the clinician, the monitor will submit an EMR. In step 2411, the feeding tube is in the stomach and at the targeted distance which signals to a feed pump to start delivering nutrition.

VIII. Tube Localization Through Local Conductivity Measurements

The conductivity measurement from the conductivity sensor (2201-2204) at the distal tip of the feeding tube 102 in FIGS. 22A-22E may also be used to determine feeding tube placement. The conductivity sensor can identify the tissues that it is in contact with because each tissue has different conductivity. The conductivity at two or more frequencies may be measured to further help determine the identity of the tissue. The lower respiratory tract is filled with air, lined with mucus, and propped open by connective tissue, namely tracheal cartilage. Air and connective tissue has low conductivity. Additionally, since the lower respiratory tract is propped open by connective tissue, the conductivity sensor may move away from the walls of the trachea or bronchi and only be touching air. This effect can be emphasized by placing the conductivity sensor in a depression on the feeding tube. This ensures that the conductivity sensor reads the low conductivity of air if it is ever in the lower respiratory tract. The esophagus is a virtual space lined with smooth muscle. While the feeding tube is in the esophagus, the walls will close in around the tube and make electrical contact with the conductivity sensor. If the conductivity measurement is within the range of smooth muscle tissue, this indicates that the feeding tube is likely in the esophagus. While the feeding tube in is in the stomach, the conductivity sensor will measure the high conductivity of gastric chyme. This high conductivity indicates that the conductivity sensor is placed in the stomach. The pattern that the conductivity changes through time may also be indicative of the tissue touching the conductivity meter. If the feeding tube was in the lower respiratory tract, the feeding tube may go in and out of electrical contact with the walls of the tract. This may produce a characteristic pattern of conductivity indicative of being in the lungs. Likewise, in the esophagus, the muscles may expand and contract. This will vary the conductivity of the muscles and change the pressure on the conductivity sensor. This may result in a conductivity pattern in time that is indicative of being in the esophagus.

Figure 25:
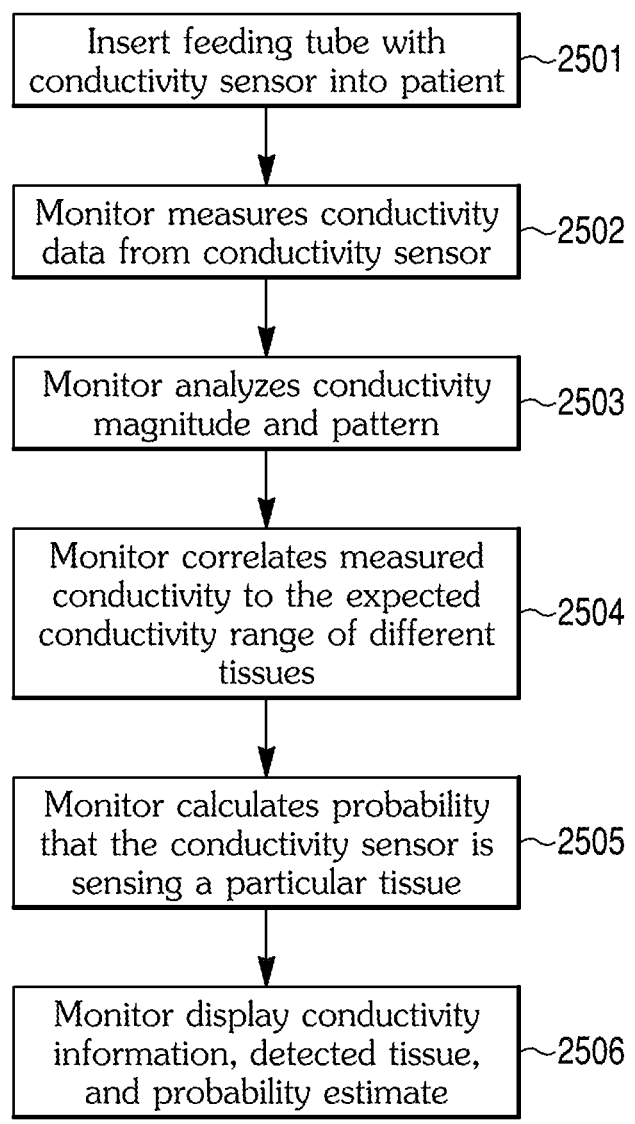
FIG. 25 is a flowchart of an exemplary method and apparatus for determining the location a feeding tube via local conductivity measurements

An exemplary process for using the conductivity sensor to assist with tube placement is show in FIG. 25. In step 2501, the clinician inserts the feeding tube with a conductivity sensor into the patient. In step 2502, the monitor 110 measures the conductivity at one or more frequencies. In step 2503, the monitor analyzes the conductivity and pattern of conductivity changes. In step 2504, the monitor correlates these conductivity values and patterns to the expected conductivity and conductivity patterns of different tissues a feeding tube may come into contact during regular or erroneous use. In step 2505, the monitor calculates that probability that the conductivity sensor is touching a particular tissue. Finally, in step 2506, the monitor displays the conductivity information and the detected tissue to the clinician. If the monitor detects that the conductivity sensor is in the lower respiratory tract with a probability above a certain threshold, it will alert the clinician to remove the feeding tube and try to insert it again.

FIG. 26 shows an embodiment of the GRV measuring device in a human stomach. GRV measuring device 2608 in this embodiment is a catheter, or tube containing at least one lumen. The GRV measuring device also includes sensor or sensors 2610, in this embodiment, at or near the distal tip of the GRV measuring device. The lumen may be used for feeding the patient, and/or introducing a GRV indicator into stomach 2602. Stomach contents 2604 include gastric secretions, nutrients which were previously present in the stomach, nutrients that have been added to the stomach via the GRV measuring device or otherwise, as well as any GRV indicators used to determine the GRV of the stomach.

GRV indicators may include a substance at a higher or lower temperature than the stomach contents, a substance at a higher or lower pH than the stomach contents, a substance at a higher or lower O2 concentration than the stomach contents, a substance at a higher or lower CO2 concentration than the stomach contents, a substance at a higher or lower ion (such as Magnesium) concentration than the stomach contents, a substance at a higher or lower glucose concentration than the stomach contents, a substance at a higher or lower viscosity than the stomach contents, etc. Additional GRV and/or stomach entry indicators include electrical properties (conductance, resistance, current generation based on the acid level, impedance, etc.) that will increase or decrease depending on the ratio of stomach acid to tube feed in the stomach. Other GRV indicators are also possible and some are described in other embodiments herein.

GRV indicators may be introduced through the lumen of GRV measuring device 2608 into stomach contents 2604. Sensor or sensors 2610 then can measure the change in properties of the stomach contents to determine the Gastric Residual Volume, or GRV, of the stomach.

For example, if a substance is introduced into the stomach which is at a higher or lower temperature than the stomach contents, the sensor(s) can measure the magnitude of change, and/or the rate of change of temperature of the stomach contents to determine the GRV. Both the rate of initial change, and the rate of change back to the pre-introduction state can be measured, as well as the magnitude of change. In general, the change from the maximum change, back to the pre-introduction level, is a slower change and easier to measure, but either change can be measured. After the GRV indicator is introduced, and the maximum level of the GRV indicator has been measured, the rate of change of the indicator, or slope of the temperature vs. time curve, can be measured. A relatively steep slope indicates a higher GRV, where a relatively shallow slope indicates a lower GRV. The same can be done with concentration and other GRV indicator types. For example, if the GRV indicator is glucose, the sensor(s) would measure the concentration of glucose within the stomach contents and the change in concentration over time.

Alternatively, a bolus of a substance at a fixed temperature (or concentration, etc., depending on the GRV indicator) can be introduced into the stomach and the temperature (or concentration, etc.) of the stomach contents can be measured as soon as the contents have had a chance to mix. The relatively immediate magnitude of change in temperature or concentration may also be an indicator of the GRV of the stomach. The lower the GRV, the greater the impact the introduction of the GRV indicator will have on the stomach contents. The higher the GRV, the lower the impact will be, resulting in a lower magnitude of measured change of the GRV indicator.

Another embodiment of the GRV measuring device includes a temperature changing mechanism as part of the device. In this embodiment, the temperature of the stomach contents may be altered by either a heating or cooling element. For example, GRV measuring device 2608 may include a heating element (not shown) which heats the contents of the stomach. The change of temperature is measured over time and the rate and/or magnitude of the temperature change as the stomach contents heat and/or cool can be used to determine the GRV of the stomach.

Another variation of this embodiment of the GRV measuring device measured pH instead of temperature. A substance of a certain pH (higher or lower than that of the stomach contents) can be introduced into the stomach, and the change in pH measured over time to determine the GRV of the stomach.

A controller (not shown) may be used as part of the GRV measuring device to record and/or interpret the various levels of GRV indicator(s) measured by sensors within the stomach. The controller may also use the GRV info to control feeding volume/rate/frequency/contents.

FIG. 27 shows a stomach into which a substance containing a concentration of a GRV indicator is introduced and the concentration measured over time within the stomach contents. In this embodiment, the sensor(s) measure concentration instead of temperature. For example, GRV indicator 2702 in this embodiment may be glucose, or magnesium, or any other suitable substance, the concentration of which can be measured.

Figure 28:
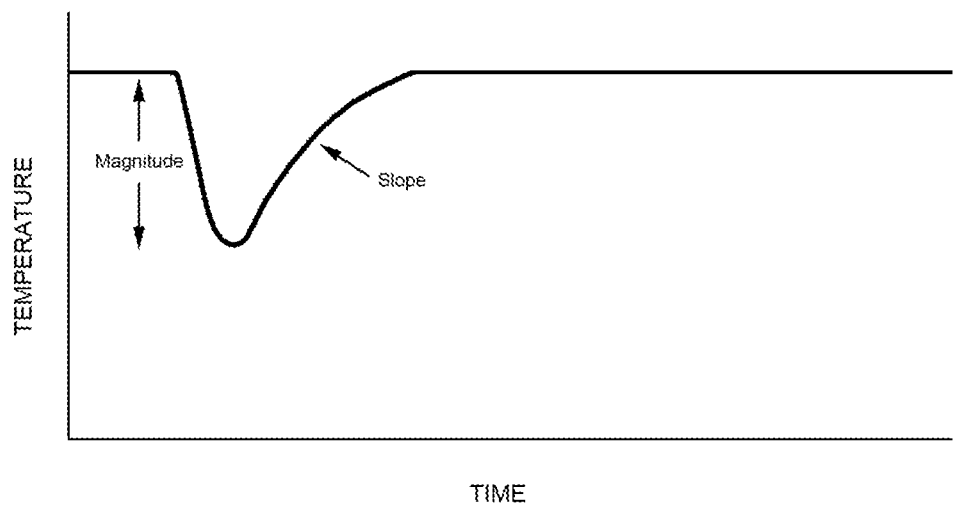
FIG. 28 shows a graph of the temperature of the stomach contents over time as sensed by sensor(s) after a bolus of cold substance is introduced into the stomach.

FIG. 28 shows a graph of the temperature of the stomach contents over time as sensed by the sensor(s) and recorded and/or interpreted by the controller after a bolus of cold liquid is introduced into the stomach. The magnitude of the temperature drop and the slope of the gradual temperature rise back to normal can be used either together, or separately, to determine the GRV of the stomach.

Figure 29:
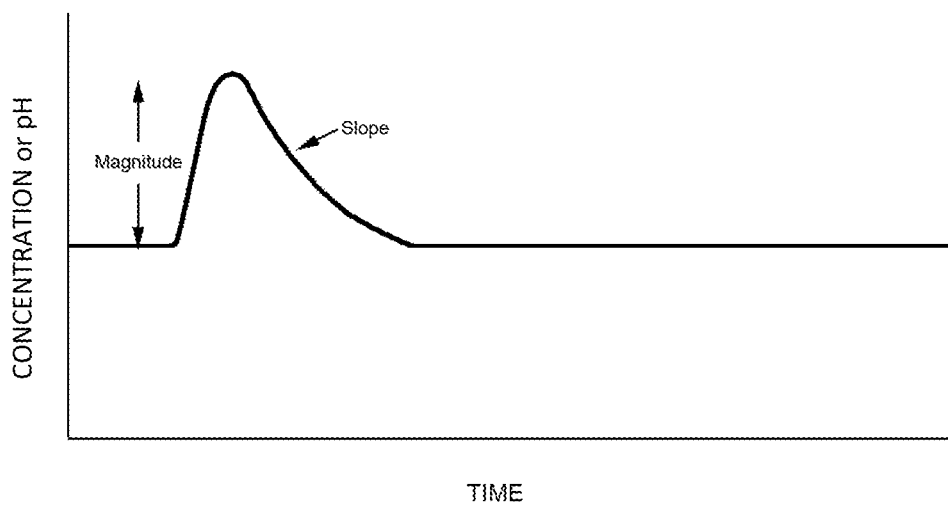
FIG. 29 shows a graph of the concentration or pH of a GRV indicator over time after introduction into the stomach.

FIG. 29 shows a similar graph for the introduction of a GRV indicator for which the concentration or pH is measured. After introduction of the GRV indicator into the stomach, the concentration or pH rises, and then gradually returns to normal over time. Again, the magnitude of the change and the slope of the return to normal of the concentration or pH of the GRV indicator within the stomach can be used together, or separately, to determine the GRV of the stomach.

Figure 30:
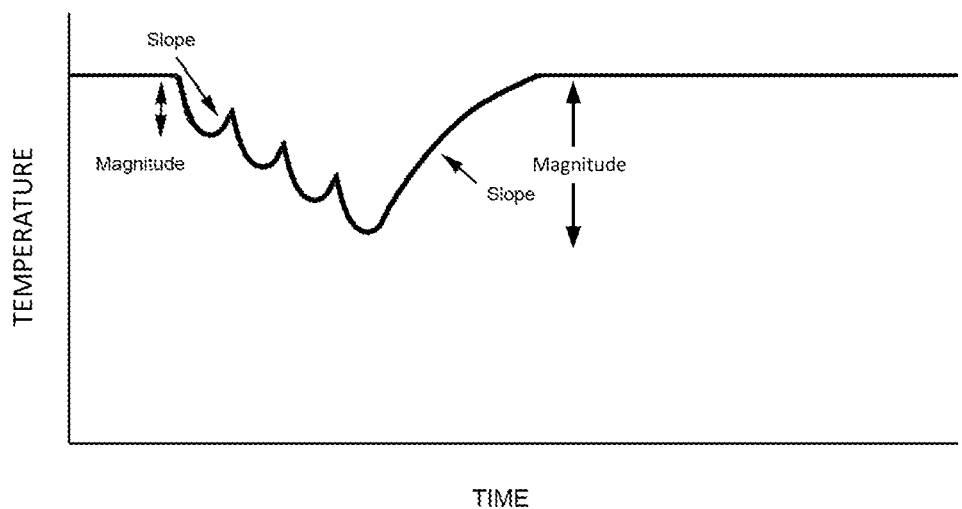
FIG. 30 shows a graph of the temperature of the stomach contents over time as sensed by sensor(s) after multiple boluses of cold substance are introduced into the stomach.

FIG. 30 shows a graph of the temperature of the stomach contents over time as sensed by the sensor(s) and recorded and/or interpreted by the controller after multiple boluses of cold liquid are introduced into the stomach. Note that in this example, the magnitude and/or slope of the graph after each bolus may be utilized by the controller, in addition to the overall magnitude and slope of the boluses combined. Multiple boluses may be used with other GRV indicators as well.

Figure 31:
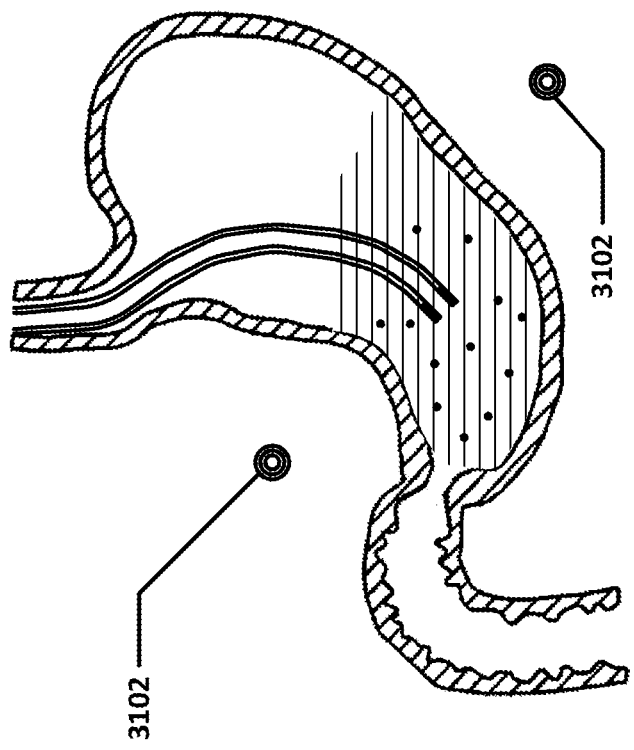
FIG. 31 shows an embodiment of the GRV measuring device where sensors are outside of the stomach.

FIG. 31 shows an embodiment of the GRV measuring device where sensors 3102 are outside of the stomach, and preferably outside the patient's body. This embodiment is limited to GRV indicators which can travel through tissue such as temperature, radiation, sound waves, magnetic substances, etc.

Figure 32:
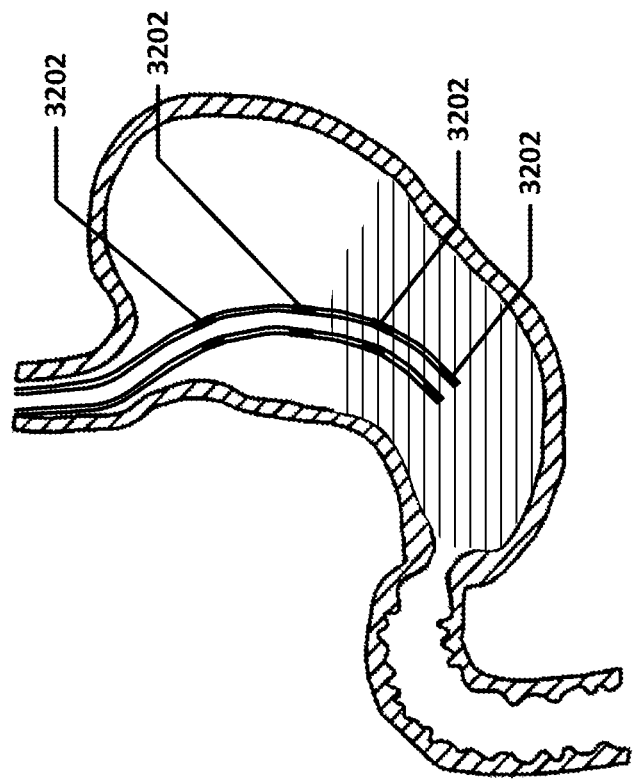
FIG. 32 shows an embodiment of the GRV measuring device where sensors are located along the length of the catheter or tube.

FIG. 32 shows an embodiment of the GRV measuring device where sensors 3202 are located along the length of the catheter or tube. In this embodiment, the GRV indicator can be measured at different locations within the stomach, providing more information regarding the GRV. For example, assuming the patient is upright and the stomach contents are at the bottom of the stomach, the GRV indicator readings at the more proximal end of the GRV measuring device would be much lower, or even null, where the measurements at the distal end of the device would change over time as the GRV indicator is introduced and diluted by the stomach contents. Depending on the different GRV indicator measurements at different locations along the GRV measuring device, more information can be obtained about the volume of the contents in the stomach. For example the device may be able to determine that the stomach is approximately half full etc.

Figure 34:
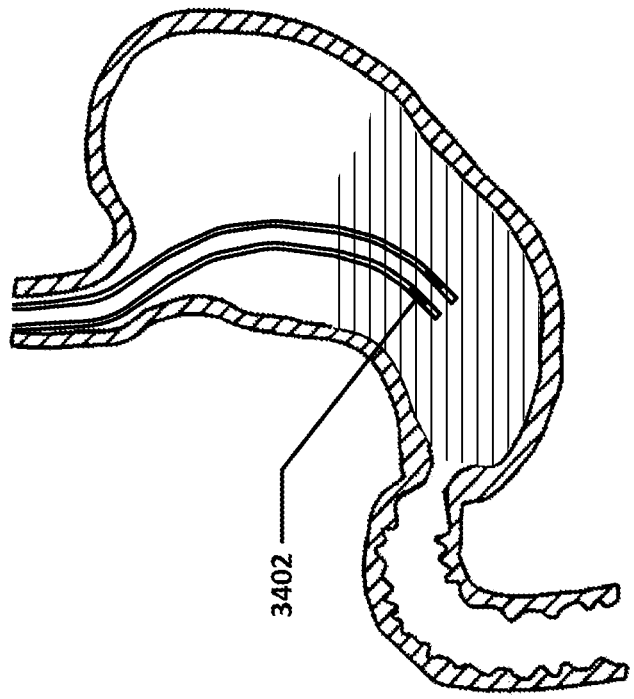
FIGS. 33 and 34 show embodiments of the GRV measuring device where sensor(s) are at different location.
Figure 33:
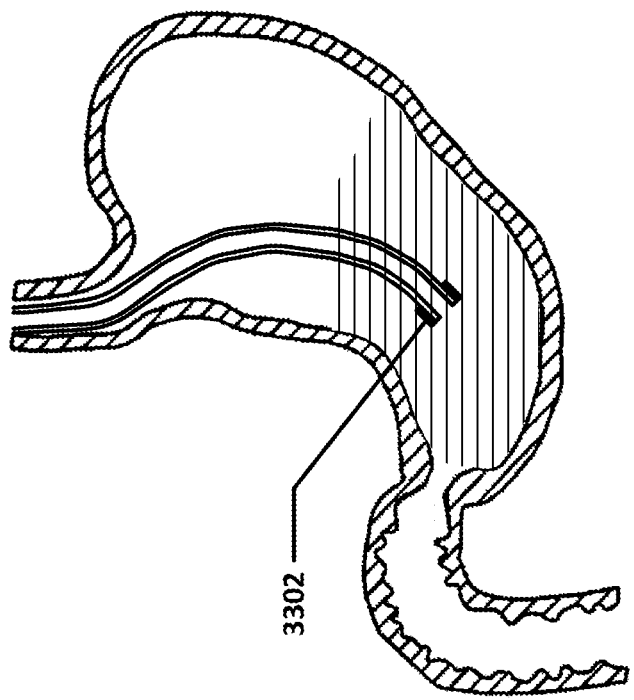

FIGS. 33 and 34 show embodiments of the GRV measuring device where the sensor(s) are at different location. FIG. 33 shows sensor(s) 3302 on the outside of tube/catheter. Note that in any of the embodiments herein the sensor(s) may run radially around the tube/catheter or be on one or more sides of the catheter/tube. This, and other embodiments, also allows for a separate feeding tube to be inserted through the GRV measuring device (not shown). This may be desirable where a standard feeding tube is being used. Also, it is possible to insert the GRV measuring device into the patient over a feeding tube that is already in place. This would be advantageous when it is not known at the time of placement of the feeding tube that the GRV measuring device will be used.

FIG. 34 shows sensor(s) 3402 embedded in the wall of the GRV measuring device. This embodiment offers the advantage of a smooth transition on both the outside and the inside of the GRV measuring device. Note that the sensor(s) in any of the embodiments may be at any location along the length of the GRV measuring device.

Figure 35:
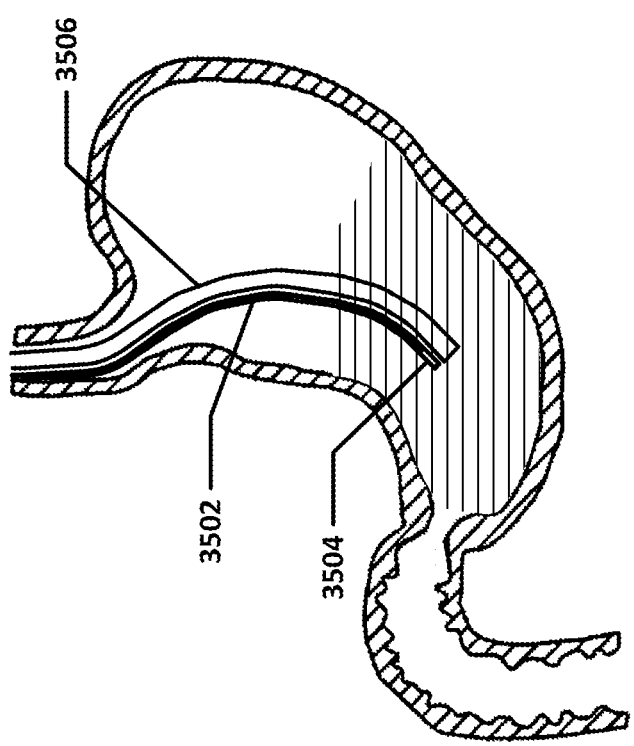
FIG. 35 shows an embodiment of the GRV measuring device which is separate from a feeding tube.

FIG. 35 shows an embodiment of the GRV measuring device which is separate from the feeding tube. In this embodiment, feeding tube 3506 may be inserted into the patient separately from GRV measuring device 3502. GRV measuring device in this embodiment may or may not have a lumen. Since the feeding of the patient occurs through a separate tube, the size of the GRV measuring device can be much smaller and be inserted alongside of the feeding tube. In fact, GRV measuring device in this embodiment may be similar dimensions to a guide wire (down to 0.5 mm or less, or 1.0 mm or less, or 2.0 mm or less) with sensor(s) 3504 at its distal end or along its length. In this embodiment the GRV indicator may be introduced through the separate feeding tube.

Figure 36:
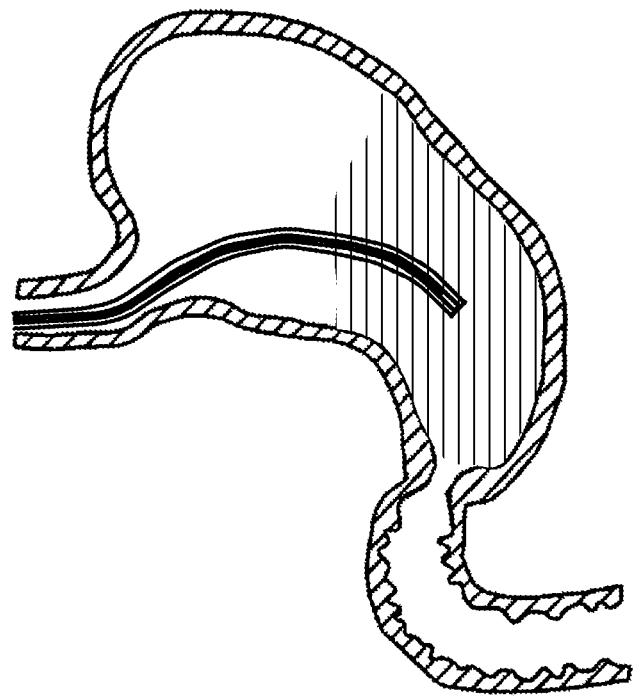
FIG. 36 shows a GRV measuring device where the GRV measuring device is inserted through a feeding tube.

FIG. 36 shows a GRV measuring device similar to that of FIG. 35, however in this figure, the GRV measuring device is inserted through the feeding tube. This configuration has the advantage of easily being inserted after the feeding tube is already in place. In this and any of the embodiments the GRV measuring device may be introduced only periodically before or after the GRV indicator is introduced into the stomach. In this way, the extra bulk of the GRV measuring device does not significantly interfere with the feeding process through the feeding tube. Alternatively, the GRV measuring device may be small enough to not adversely impact the flow of nutrients or other substances through the feeding tube.

Figure 38:
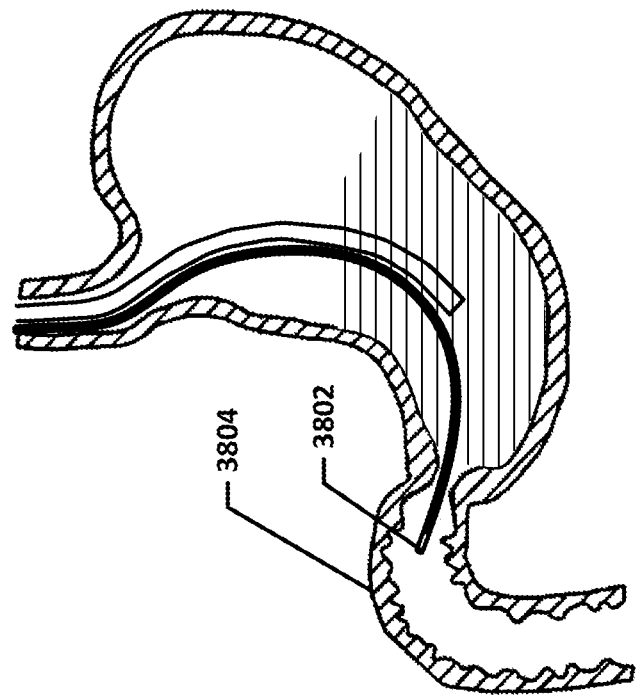
FIGS. 37 and 38 illustrate how the sensor(s) of the GRV measuring device may be located at various places relative to the feeding tube.
Figure 37:
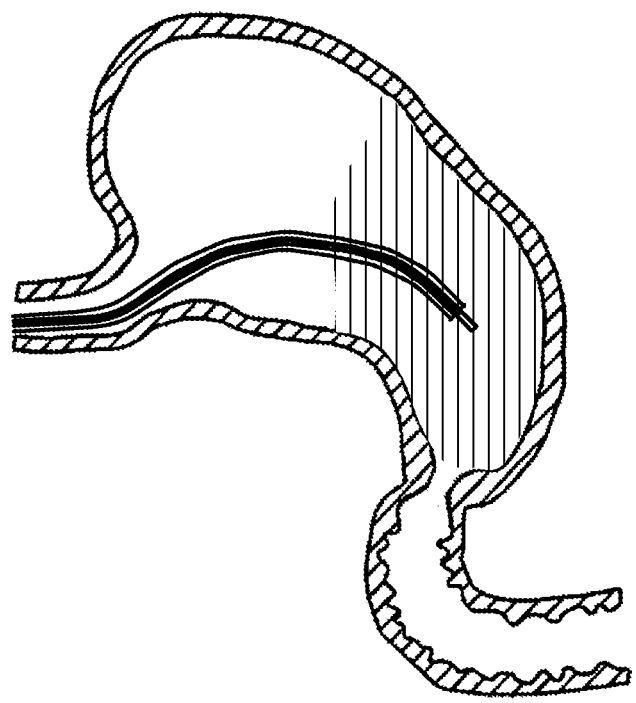

FIGS. 37 and 38 illustrate how the sensor(s) of the GRV measuring device may be placed at various places relative to the feeding tube. This may help obtain cleaner measurements after introduction of the GRV indicator. For example, if a heated substance is introduced through the feeding tube, it may be advantageous to have the sensors of the GRV measuring device some distance away from the exit of the feeding tube, both to protect the sensors from extreme heat, but also to get a cleaner temperature reading. More mixing of stomach contents will have occurred the further from the source of the GRV indicator introduction the sensor(s) are.

Alternatively the sensors may be placed within the feeding tube when the GRV indicator is introduced through the feeding tube to obtain a baseline reading of the temperature/concentration/pH etc. of the GRV indicator. The sensors may then be moved into the stomach contents to obtain the changing readings which will be used to determine GRV. Alternatively, the GRV measuring device may have sensors along its length to achieve the same thing. There may be other advantages to moving the GRV measuring device during the measurement process. Measuring the GRV indicator at different places within the stomach and/or stomach contents will provide more information about the stomach contents.

FIG. 38 shows sensor(s) 3802 of the GRV measuring device in the pylorus 3804. In this embodiment, the stomach content volume is estimated through direct measurement of the input volume (enteral feeding material) and output volume (pylorus transit). The amount of material entering and passing through the pylorus may be measured with a volumetric flow meter, or Doppler ultrasound, or optics, or any other suitable technology. In one embodiment, after magnetic materials are introduced into the stomach, the movement of the materials induces a current as it passes the pylorus transit which can be measured either within the pylorus, or outside of the patient.

Note that in any of the embodiments herein, the GRV measuring device may be outside of, inside of, incorporated into or completely separate from the feeding tube.

Figure 40:
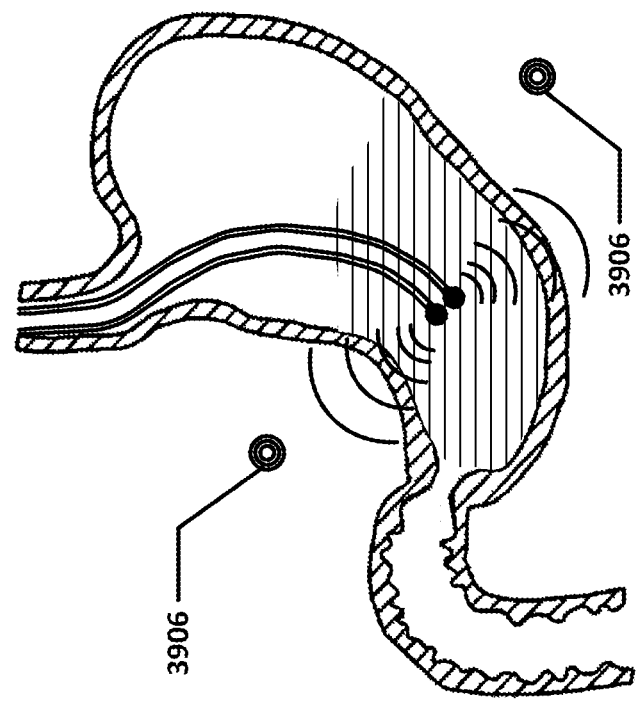
FIGS. 39-41 show embodiments of the invention in which there is at least one transmitter and/or receiver to track location of the device within the stomach and/or stomach contents.
Figure 39:
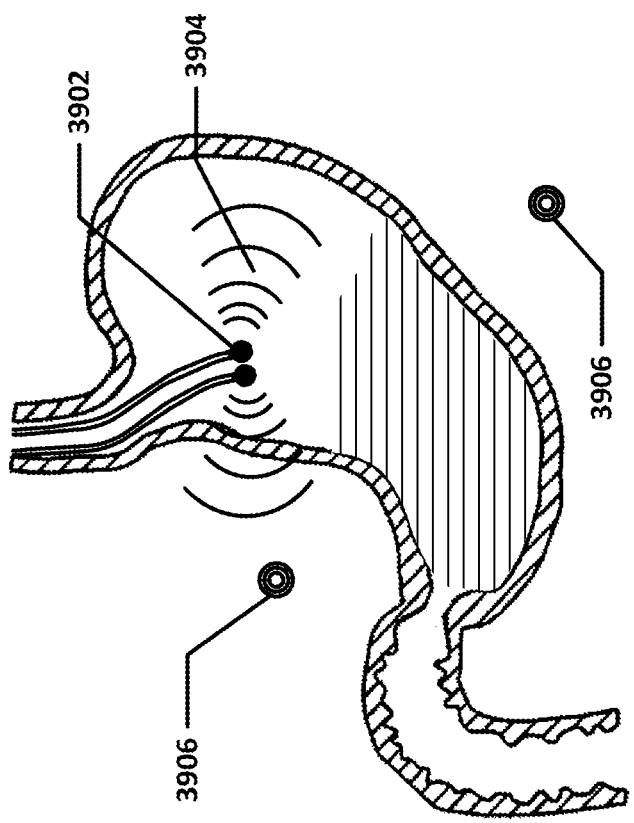
Figure 41:
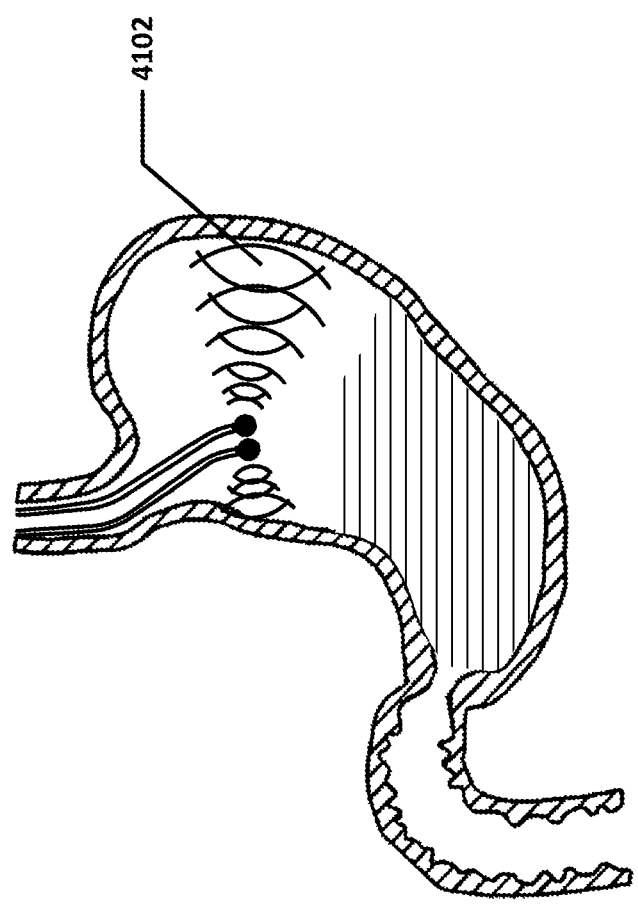

Other embodiments of the invention are shown in FIGS. 39-41. In these embodiments, the GRV measurement device is also used to locate the device, or a feeding tube, within the stomach to ensure proper feeding and GRV measurements. In these embodiments transmitters 3902 give off signal 3904 which is detected by location receivers 3906. The transmitters may be separate from the sensor(s) shown in other embodiments, however both may be present on the GRV measuring device (note that the sensor(s) are not shown in FIGS. 39-41). The location receivers may exist outside the body as shown in FIGS. 39 and 40, or they may be part of the GRV measuring device, as shown in FIG. 41. The transmitted signal may be a sound signal, an ultrasound signal, a pressure signal, or any other suitable signal. Alternatively, or in addition, pH, temperature, or any of the GRV indicator signals may be used. The location receivers receive the signal either through the tissue, as shown in FIGS. 39 and 40, or after reflected signal 4102 has bounced off of the walls of the stomach and possibly the stomach contents, as shown in FIG. 41. The embodiment of the GRV measuring device in FIG. 41 includes both the transmitters and the location receivers on the device within the stomach.

FIGS. 39 and 40 show the transmitter in the empty part of the stomach and in the stomach contents, respectively. The signal received when the transmitter is in these two different locations will be very different, and will aid in locating the tip of the feeding tube. The transmitters may be at the tip of the feeding tube, and/or may be elsewhere relative to the tip of the feeding tube.

Figure 42:
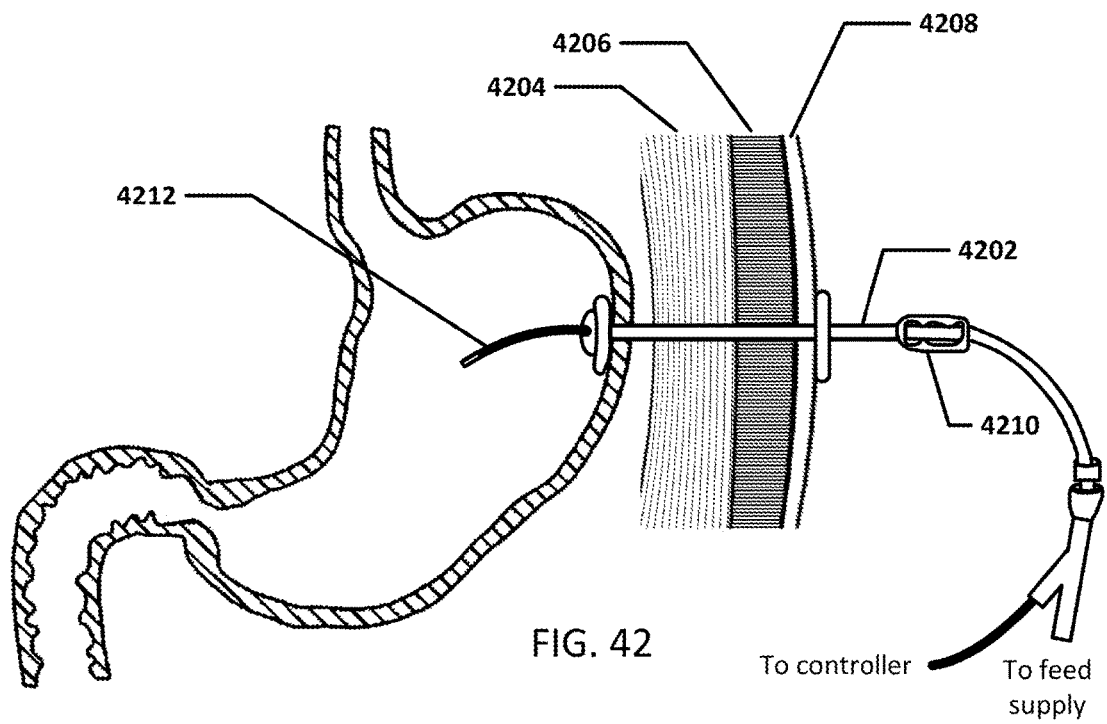
FIGS. 42 and 43 show embodiments of the GRV measuring device for use percutaneously.
Figure 43:
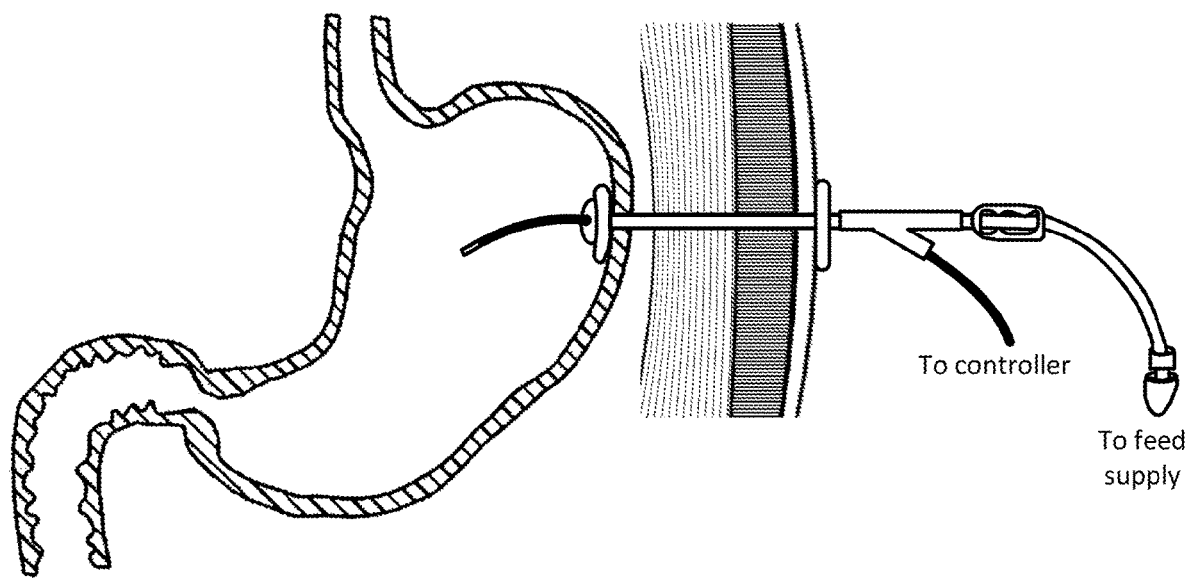

FIGS. 42 and 43 show embodiments of the GRV measuring device being used percutaneously. For example, the GRV measuring device can be used as, or in conjunction with, a Percutaneous Endoscopic Gastrostomy, or PEG, tube. In this situation the feeding tube goes through the abdomen of the patient, directly into the stomach, to feed the patient. Shown here is PEG tube 4202 going through skin 4208, fat 4206 and muscle 4204 and through the stomach wall so that the tip of the PEG tube is in the stomach. The GRV measuring device may be incorporated into the PEG tube, or may be separate as shown here. GRV measuring device 4212 is shown here being used through the inside of a PEG tube. In this and other embodiments the GRV measuring device is connected to a controller to record and/or interpret the measurements sensed by the sensors.

In this and other embodiments, GRV measuring device may be in the stomach throughout feeding, or it may be introduced periodically when measurements are desired. Restrictor 4210 may be used to control the flow of nutrients into the stomach. The restrictor may be controlled by the controller in a feedback loop so that nutrients are only introduced when the GRV is at or below a certain level. Nutrients may also be automatically limited when the GRV is at or above a certain level. These levels may be preset, or may be set by the controller and can be adjusted as necessary. This type of feedback control also allows for bolus feeding vs. continuous feeding which is more physiologically representative.

FIG. 43 is similar to FIG. 42 except that the entrance point for the GRV measuring device is between the patient and the resistor. This allows the resistor to be more easily used when the GRV measuring device is in place.

Note that the embodiments in FIGS. 42 and 43 can be used with a standard PEG tube. Alternatively, the GRV measuring device may be incorporated into a PEG tube.

Figure 44:
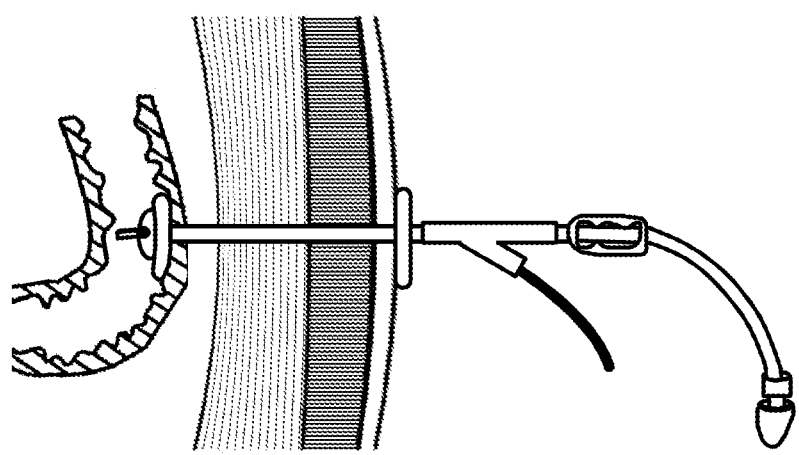
FIG. 44 shows an embodiment of the GRV measuring device for use with a jejunostomy tube.

FIG. 44 shows an embodiment of the GRV measuring device for use with a jejunostomy tube. In this embodiment the feeding tube enters the intestines rather than the stomach. Similar to other embodiments herein, the GRV measuring device may be used with a standard jejunostomy tube, or may be incorporated into a jejunostomy tube.

Figure 45:
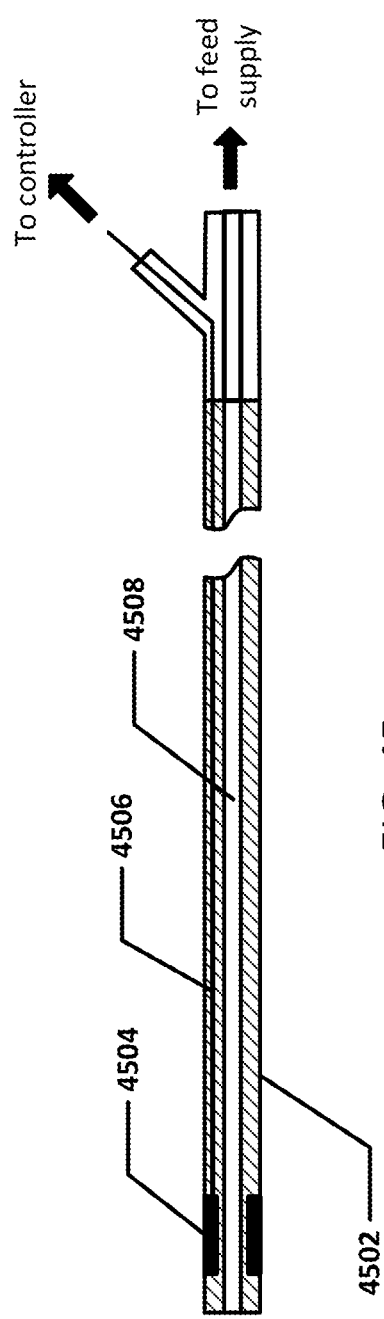
FIGS. 45-49 show embodiments of the GRV measuring device.

FIGS. 45-49 show detailed embodiments of the GRV measuring device. FIG. 45 shows an embodiment of the GRV measuring device which is incorporated into a feeding tube. Device shaft 4502 includes sensor or sensors 4504, measurement communication line 4506, which may be a metal wire, as well as feeding lumen 4508. Sensor(s) 4504 measure the temperature, pH, concentration etc. of the GRV indicator in the stomach after the indicator is introduced through the device or created by the device. For example, a fluid below body temperature may be introduced into the stomach through lumen 4508. The magnitude of the change of temperature within the stomach is measured by sensor(s) 4504, as well as the rate of return to normal temperature. This information is transferred along communication line 4506, along shaft 4502 back to the controller. The controller may control the feed supply either with user input, or automatically, depending on the gastric volume analysis of the controller.

Note that sensor(s) 4504 may be placed anywhere along the length of the device. Also note that sensor(s) may be placed on either the inside of the device (within lumen 4508) or on the outside, or both. Having separate sensors on both the inside and outside of the device may allow measurements of the untainted GRV indicator as it is entering the stomach (inside sensors) as well as measurements of the change in the GRV indicator over time (outside sensors). These sensors may be the same sensor, where it measures both inside the device, and outside the device. Also note that there may be a barrier or insulator between the sensor and either the inside of the device, or the outside of the device. This would allow the sensor to measure the GRV indicator on either the inside of the device or the outside of the device without being tainted.

Alternatively the GRV measuring device may cause a cooling of the stomach contents with a cooling element (not shown) on the device, and measure the resulting magnitude and rate of temperature change to determine gastric volume.

In another example, the pH of the stomach contents may be measured to determine gastric volume. A substance of a known pH (which may be only the feeding substance itself) is introduced into the stomach, and the sensor(s) measure the change in pH and the rate of return to normal pH, send the information back to the controller, and the controller can then determine gastric volume.

In another embodiment, the GRV measuring device may use more than one GRV indicator. For example, both temperature and pH may be used. In this example, measurement of one GRV indicator may be used to confirm the measurement of the other GRV indicator for a more accurate result. In addition, the measurements may be taken at different locations to assure stomach content mixing and/or to improve accuracy. Other GRV indicators may be combined in a similar manner.

Figure 46:

FIG. 46 shows another embodiment of the GRV measuring device. This embodiment is designed to be used with a feeding tube, either alongside it or through the lumen of a feeding tube. This embodiment may be of a relatively small diameter (down to 0.5 mm or less, or 1.0 mm or less, or 2.0 mm or less) so that it does not substantially impede the flow of nutrients to the patient through the feeding tube, or is not difficult to insert into the patient alongside a feeding tube. Shaft 4602 is preferably relatively stiff, similar to a guidewire, and incorporates the signal communication from sensor(s) 4604. Shaft 4602 may be made out of metal such as stainless steel or other appropriate material. In this embodiment, the GRV indicator may be introduced through the separate feeding tube. Note that this and other embodiments may be placed into the stomach before or after the feeding tube is placed in the stomach.

Figure 47:
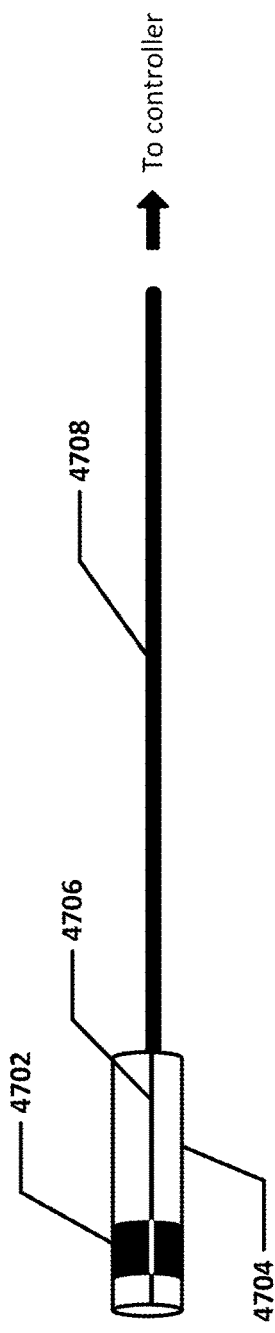
Figure 48:
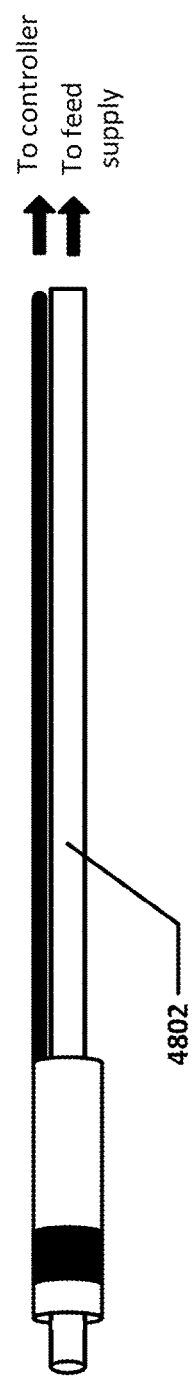
Figure 49:

FIGS. 47-49 show another embodiment of the GRV measuring device which can be used in conjunction with a feeding tube after the feeding tube is already inserted. This embodiment is designed to go on the outside of a feeding tube and includes relatively stiff shaft 4708, sheath 4704, sensor(s) 4702 and slit 4706. Shaft 4708 may be made out of similar materials to shaft 4602 in FIG. 46. Sheath 4704 is preferably thin enough so that it can easily be slid over a feeding tube, yet rigid enough so that it does not collapse. Various polymers and other materials may be used. To introduce this embodiment after a feeding tube is already in place, sheath 4704 is placed over the outside of the proximal end of the feeding tube using slit 4706. The GRV measuring device is then slid down the outside of the feeding tube into the stomach of the patient using the relatively rigid shaft 4708.

FIG. 48 shows this embodiment of the GRV measuring device after it is placed over feeding tube 4802.

FIG. 49 is a cross sectional view of this embodiment of the GRV measuring device.

Figure 50:
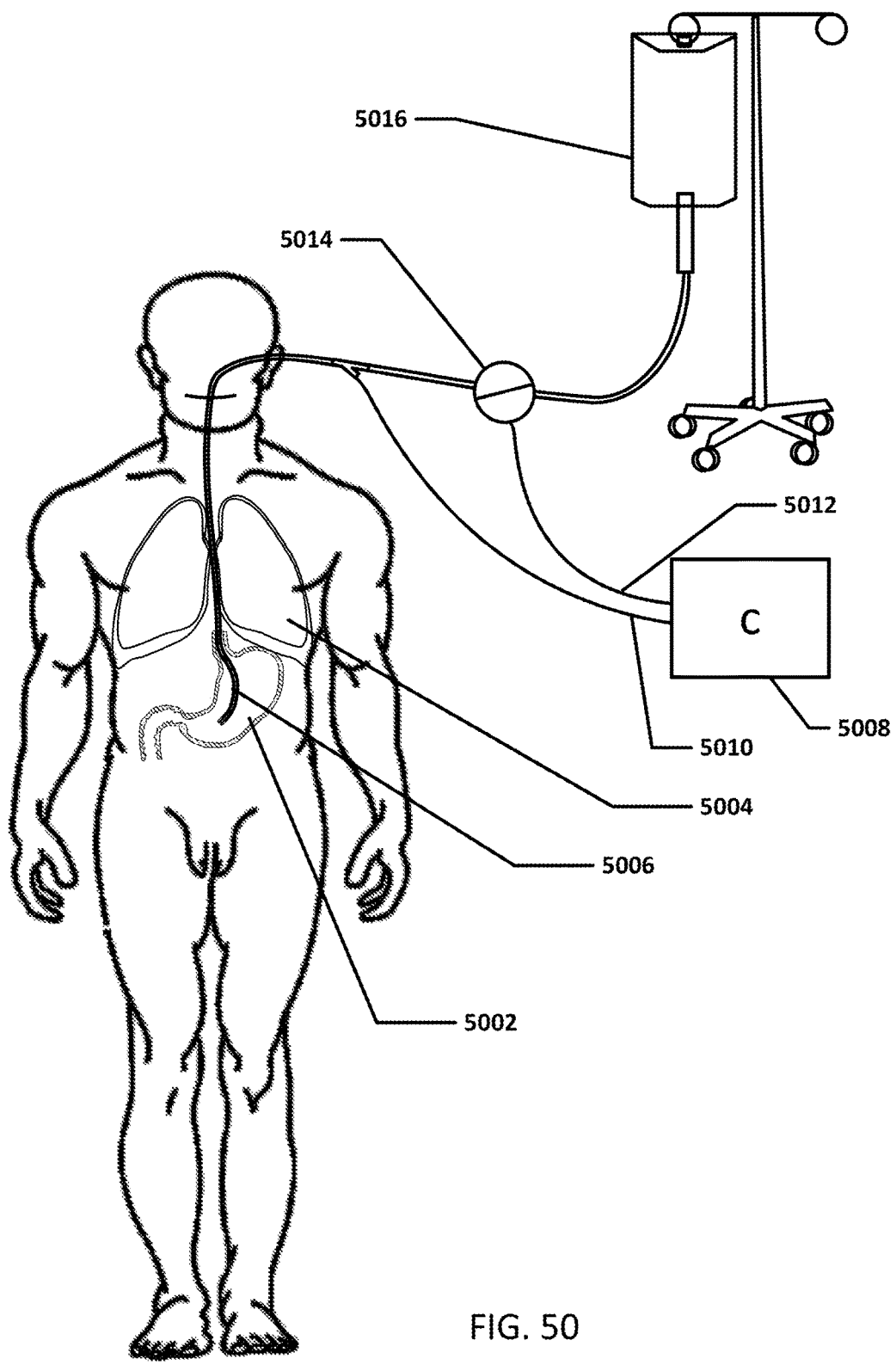
FIG. 50 shows an embodiment of the device where GRV and entry in the stomach is based on a continuously or intermittently monitored physical characteristic.

FIG. 50 shows an embodiment of the device where GRV and entry in the stomach is based on a continuously or intermittently monitored physical characteristic. In this embodiment, the GRV indicator may be inherent in the feed or meal itself, with no additives required. In this embodiment, the GRV indicator may be a physical characteristic such as pH or electrical resistance, impedance or conductance. In this embodiment, the physical characteristic may be monitored over time and the changes that occur as the meal empties from the stomach may be recorded. As the meal leaves the stomach and the relative concentration of gastric fluid increases the physical characteristic is altered in a measureable way. In one embodiment, the physical characteristic is pH wherein the pH decreases as the meal leaves the stomach and the gastric secretions represent more of what is left in the stomach. Once the pH reaches a sufficiently low level the device may alert the user that the meal has left the stomach and the patient is ready for another bolus. In another embodiment the physical characteristic is resistance or impedance. The meal delivered to the patient may be formulated to have high resistance or impedance so that subsequent decreases will indicate increasing concentration of gastric secretions. The opposite is true of conductance, which may increase as the meal leaves the stomach.

In yet another embodiment, the sensor may consist of a circuit that is powered by acid. For example, two leads may be introduced into the stomach consisting of different metals (in the preferred embodiment these are copper and magnesium) In the presence of acid, these metals act like the terminals of a battery and create a current. This current can be continuously or intermittently recorded and report the emptying of the stomach based on the increased concentration of acid. The same electrodes may also be used to sense the electrical parameters (impedance, conductance, resistance. Etc.) of the stomach to provide further information to help increase the sensitivity and specificity of the measurement. Each of these measurements of the physical characteristics of the stomach may be used, alone or in combination, to report that the sensor (and therefore the tube or catheter tip) is in the stomach and not in the lung. Ideally two or more parameters are measured (pH, current due to acid, impedance/conductance, etc.) to improve the accuracy of the measurement. This is important as the incidence of tube placement in the lung is as high as 20% and starting tube feeds with the tip in the lung can be fatal. In this embodiment, the sensors may be incorporated into the catheter/tube itself or may be a separate component that is threaded down the inside of an existing feeding catheter/tube to provide a spot reading as to the location of the tip of the tube. In the ideal embodiment, the sensor(s) is/are integrated into the catheter/tube to first provide an indication that the catheter/tube is in the stomach (and not the lung) and then provide a signal to indicate the GRV to help optimize feeding. In the ideal embodiment, as well, the feeding may be accomplished via a closed loop system that will automatically detect the GRV and deliver tube feed when appropriate based on the programmed nutritional goals for each patient. In this embodiment, target volumes of tube feed may be set per period of time and maximum volumes may be programmed.

FIG. 50 shows a patient with GRV measuring device 5006 placed in stomach 5002. Note the proximity of lungs 5004 and why it is important to be able to confirm placement of the GRV measuring device in the stomach, rather than the lungs. The GRV is measured as discussed herein. Controller 5008 may intermittently or continuously track the GRV via connector 5010 and using this information, control the feeding of the patient via valve or restrictor 5014 using connector 5012. Note that the connectors may be wired, as shown here, or wireless. Feed supply 5016 is connected to the feeding tube and the volume, rate, frequency, and content of the feed is controlled by controller 5008. GRV indicators may be inherent in the feed, added to the feed, or added independently of the feed. The controller may collect measurements of the GRV indicator inside the feeding tube, just before the feed is released into the stomach, as well as within the stomach contents over time. This provides the controller with a reading of the GRV indicator just before mixing begins, to provide an accurate GRV.

Figure 51:
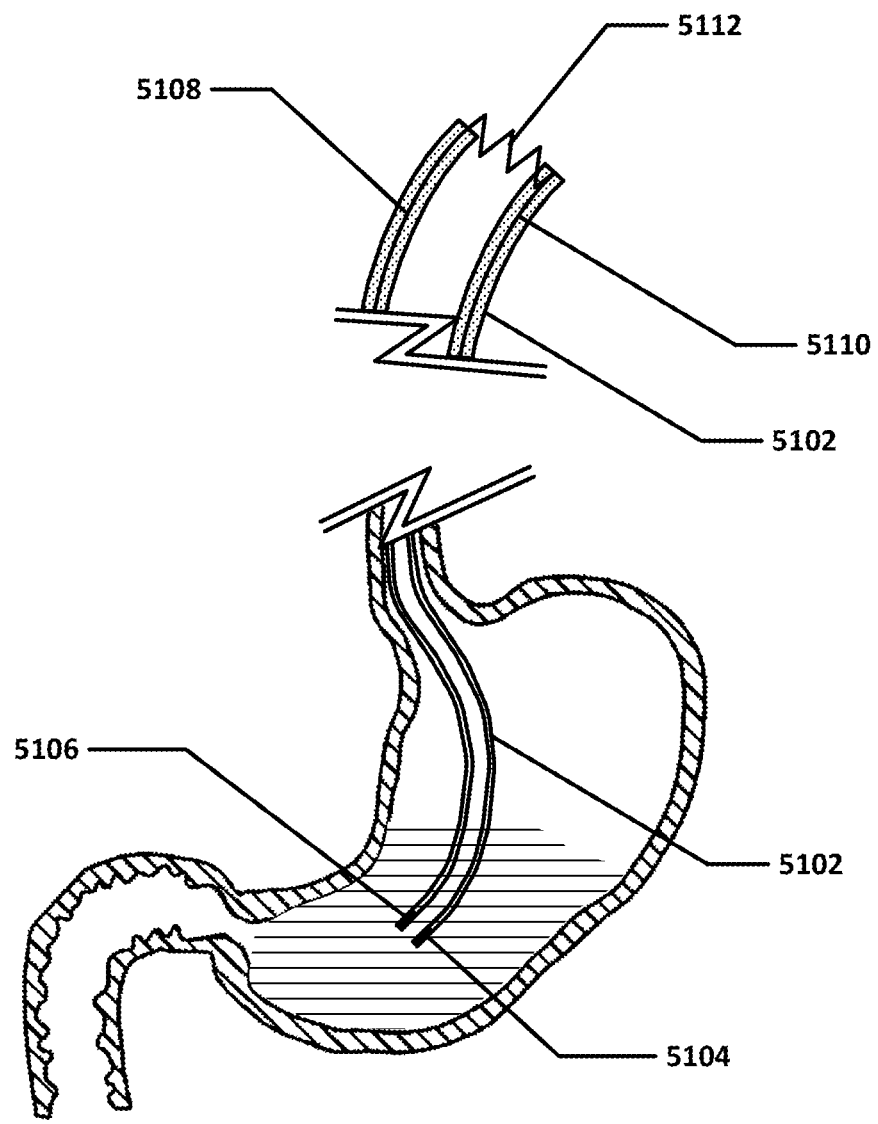
FIG. 51 shows an embodiment of the device.

FIG. 51 shows an embodiment of the GRV measuring device which uses the gastric acid in the stomach to create a sort of battery which creates a measurable current which is measured and analyzed by a controller. The measured current is indicative of the GRV in the stomach. GRV measuring device shaft 5102 contains wires 5108 and 5110 which connect to two different electrodes, 5106 and 5104. The electrodes in this embodiment are made from dissimilar metals, such as Aluminum and Copper, but other dissimilar metals may be used. The current between the two electrodes is sensed by current sense resister 5112. In this embodiment, current is generated by the fluid in the stomach, and measured and analyzed by the controller to determine GRV.

In an alternative embodiment, the impedance of the stomach fluid is measured instead of current. The impedance is indicative of the ratio of gastric acid to feed, providing an estimate of GRV. This embodiment would look similar to the embodiment shown in FIG. 51 except that the electrodes would preferably be of the same metal rather than dissimilar metals. The controller would generate a voltage and measure the resulting current to determine the impedance of the fluid in the stomach. In this embodiment, voltage is generated by the controller, and current is passed through the fluid in the stomach and the resistance is measured and analyzed by the controller to determine GRV.

Using the different electrical properties of the gastric acid in the stomach and the feed, GRV can be estimated by conductivity, current, impedance, capacitance, electrical resistance etc. AC and/or DC signals can be used to make these measurements. Several possible embodiments are envisioned. For example:

In one embodiment, an additive liquid element (such as water, saline or similar) is introduced by the source that is significantly lower or significantly greater in temperature then the nominal content temperature. Measurement of the temperature may be recorded by sensors in one or more locations in the content mixture. In one embodiment, the rate of change in temperature over a period of time indicates the gastric volume. In one embodiment, the resulting temperature from the mixture after a set period of time indicates the gastric volume. In one embodiment, a physical thermal element introduces a sudden temperature change. This element quickly could heat or chill the gastric contents in contact with the element.

In one embodiment, an additive element is introduced that changes the viscosity of the contents. The resulting change in viscosity indicates the gastric volume. In one embodiment, the additive component glucose is introduced. The resulting change in concentration of glucose indicates the gastric volume. In one embodiment, coloring elements such as methylene blue is introduced and the resulting concentration is used to indicate gastric volume. In one embodiment, an additive component is introduced that changes the pH value of the gastric contents. The rate of change or resulting pH value indicates gastric volume. In one embodiment, an additive element is introduced that changes the conductivity of the contents. In one embodiment, an additive element is introduced that changes the refractive index, opacity, absorptivity, luminosity or color of the contents. In one embodiment, an additive element is introduced that changes the specific gravity of the contents.

In one embodiment, an additive component is introduced that causes the contents to change and is measure through a method of titration. In one embodiment, the additive component causes contents to solidify. In one embodiment, the additive component causes contents to change conductivity. In one embodiment, the additive component causes contents to change optical opacity or color.

In one embodiment, pressure is introduced by introducing additional material into the gastric space. This material may be air, saline, water, or other. In one embodiment, pressure may be introduced by inflation of a balloon. In one embodiment, pressure response is measured internally. In one embodiment, pressure is measured externally with pressure gauges around the abdomen. This pressure difference before and after introduction will indicate volume.

In one embodiment, an acoustic source is used to produce standing waves in the gastric space. The resulting pattern of pressure indicates the dimensions of the media, in this case the gastric contents. In one embodiment, the acoustic source is external and an acoustic or pressure sensors are used internally. In one embodiment, both the source and sensors are internal. In one embodiment, the source is internal and the pressure or acoustic signature can be measured externally. In one embodiment, both the source and the sensor are external. The acoustic source may be a point source or an array of transducers that produce a range of frequencies and amplitudes. The acoustic or pressure sensor may be a single point of measurement or an array of sensors.

In one embodiment, the flow rate of material is measured directly in the pylorus transit. The stomach content volume is estimated through direct measurement of the input (enteral feeding material) and output (pylorus transit). In one embodiment, the amount of material entering and passing through the pylorus is measured with a volumetric flow meter. In one embodiment, Doppler ultrasound is used to measure fluid movement rate. In one embodiment, after magnetic materials are introduced into the stomach, the movement of the materials induces a current as it passes the pylorus transit. In one embodiment, optics are used to measure flow rate.

In one embodiment, an autonomous device travels within the gastric space to ensure all of the gastric contents are aspirated.

Example of Data Processing System

Figure 52:
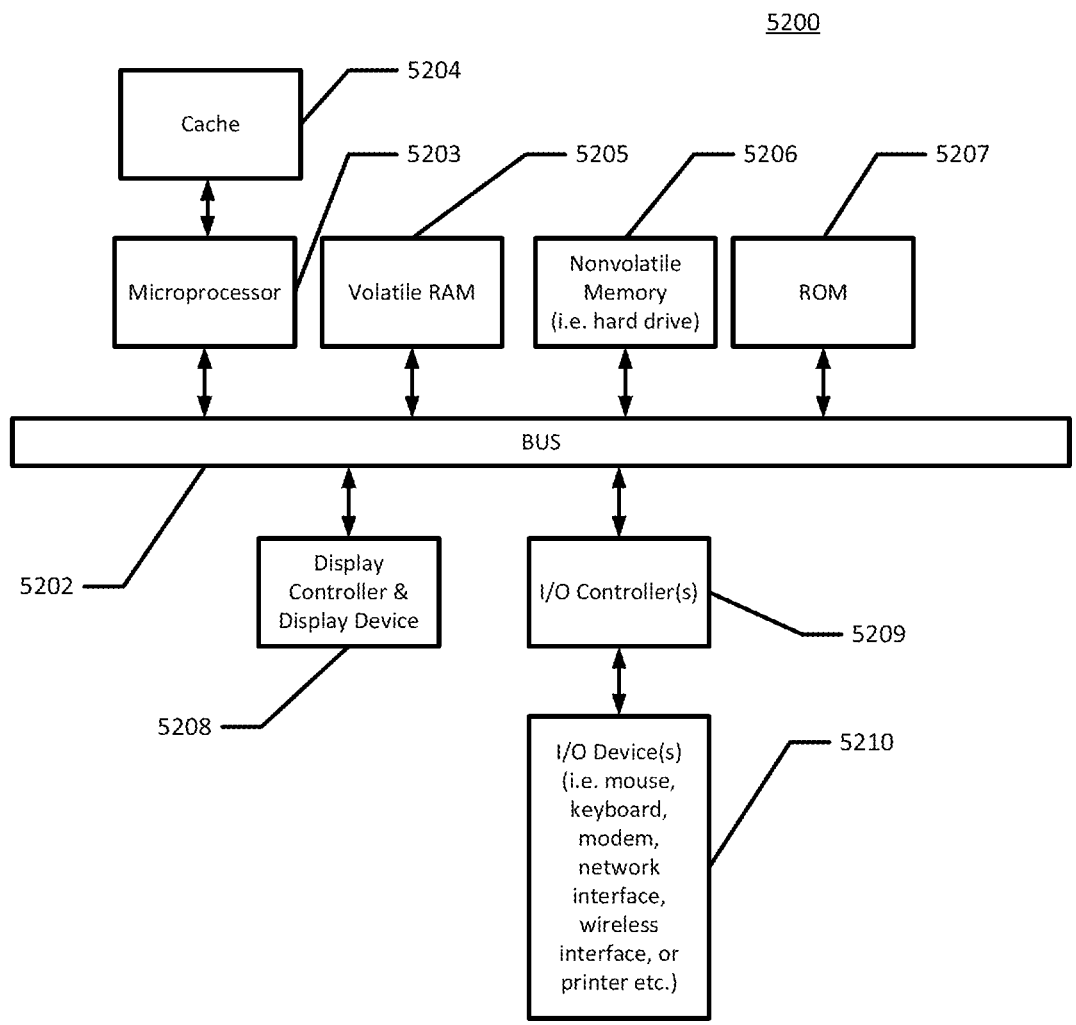
FIG. 52 is a block diagram of a data processing system, which may be used with any embodiments of the invention.

FIG. 52 is a block diagram of a data processing system, which may be used with any embodiment of the invention. For example, the system 5200 may be used as part of a controller/monitor disclosed herein. Note that while FIG. 52 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 52, the computer system 5200, which is a form of a data processing system, includes a bus or interconnect 5202 which is coupled to one or more microprocessors 5203 and a ROM 5207, a volatile RAM 5205, and a non-volatile memory 5206. The microprocessor 5203 is coupled to cache memory 5204. The bus 5202 interconnects these various components together and also interconnects these components 5203, 5207, 5205, and 5206 to a display controller and display device 5208, as well as to input/output (I/O) devices 5210, which may be mice, keyboards, modems, network interfaces, printers, and other devices which are well-known in the art.

Typically, the input/output devices 5210 are coupled to the system through input/output controllers 5209. The volatile RAM 5205 is typically implemented as dynamic RAM (DRAM) which requires power continuously in order to refresh or maintain the data in the memory. The non-volatile memory 5206 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 52 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 5202 may include one or more buses connected to each other through various bridges, controllers, and/or adapters, as is well-known in the art. In one embodiment, the I/O controller 5209 includes a USB (Universal Serial Bus) adapter for controlling USB peripherals. Alternatively, I/O controller 5209 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

FIGS. 53 and 54 show embodiments of the GRV measuring device which ensure accurate gastric tube placement and measure and report gastric residual volume by measuring the electrical conductivity of the respiratory and gastric systems. Placement in the respiratory system indicates improper placement and signals the user to replace the device.

Various tissues and fluids have different conductivities, which is largely based on the concentration of ions. Acidic solutions, such as gastric acid, have a large concentration of ions, and thus are very conductive. Common nutrition that is delivered through gastric tubes, such as milk or Ensure, are only slightly acidic, and thus are only slightly conductive.

Conductivity may be measured by passing an alternating current (AC) through the material and measuring voltage. Using Ohm's Law, the conductivity may then be calculated. The frequency of the AC current may be varied depending on the conductivity of the solution. Higher frequencies may be used for high conductivity measurements in order to minimize polarization effects (ions migrate towards the poles and block the measurement). Lower frequencies may be used for low conductivity measurements in order to minimize the effects of cable capacitance (power loss in the cable).

Electrical Conductivity Meters, such as HM Digital AP-2 AquaPro Water Quality Electrical Conductivity Tester or HM Digital EC-3 Electrical Conductivity Tester, may be used to measure conductivity.

FIG. 53 shows an embodiment of a GRV measuring device which measures conductance. Catheter 5302 also serves as a feeding tube, with openings 5308 through which the feed and/or GRV indicator may flow. Only the distal end of the catheter/feeding tube is shown here. Distal electrodes 5304 measure conductance. Proximal electrodes 5312 also measure conductance. One set, two sets, or more sets of conductance electrodes may be present along the catheter. Electrical connections, such as wires, pass from the electrodes, through the length of the catheter, to the proximal end (not shown) and ultimately to a conductivity meter. pH sensor or sensors, 5310 may also be present on the catheter, to aid in the placement of the catheter and the measurement of GRV.

FIG. 54 shows an embodiment of a GRV measuring device which measures conductance. Catheter/wire/elongated member 5402 is designed to be used through, or alongside, a feeding tube. Only the distal end of the member is shown here. Distal electrodes 5404 measure conductance. Proximal electrodes 5412 also measure conductance. One set, two sets, or more sets of conductance electrodes may be present along the member. Electrical connections, such as wires, pass from the electrodes, through the length of the member, to the proximal end (not shown) and ultimately to a conductivity meter. pH sensor or sensors, 5410 may also be present on the member, to aid in the placement of the member and/or feeding tube and the measurement of GRV.

The pH sensors, or electrodes, may consist of an internal reference and an external facing electrode. The conductance electrodes preferably exist in pairs, since one is the outgoing signal and the other is the incoming signal. Several pairs may exist on a GRV measuring device. Two "pairs" of electrodes may consist of only 3 electrodes, where one electrode serves each "pair". For example, electrodes 1 and 2 could be used for the first pair, and 2 and 3 can be used for the second pair. Examples of types of pH electrodes which may be used include antimony, glass, and/or ISFET (ion-sensitive field-effect transistor) pH electrodes.

The length of the GRV measuring device may be from about 25 inches to about 40 inches. The outer diameter of the GRV measuring device may range from about 0.02 inches to about 0.20 inches The GRV measuring device may be made out of any suitable material, including polymers, silicone etc. The GRV measuring device may contain one, two or more lumens, which may be concentric or side by side, to accommodate the various lumens and electronics required. In some embodiments of the GRV measuring device the electrode pairs are located 6 inches from each other, however the electrodes may be closer, or farther, from each other.

Below is a table which shows the results of measuring the conductance of water, simulated gastric acid and Ensure Plus, a common feed. It can be seen that the conductivity of gastric acid is well above the conductivity of water and Ensure Plus.

|  | Water | Sim. Gastric Acid | Ensure Plus |
| --- | --- | --- | --- |
| Conductivity | 55 µs | 8000 µs | 589 µs |

FIG. 55 shows that conductivity increases as the percentage of gastric acid increases in various media.

Similar results have been found in the digestive system and respiratory system of a pig. See table below. This shows that conductivity can be used to determine placement of the GRV measuring device and/or a feeding tube.

| Insertion Length | Conductivity (uS) |
| --- | --- |
| Stomach | |
| 27 in | 4699 |
| 23 in | 2994 |
| 19 in | 2975 |
| 16.5 in | 2845 |
| Lungs | |
| 27 in | 3385 |
| 19 in | 3798 |
| 16.5 in | 2867 |

Figure 56:
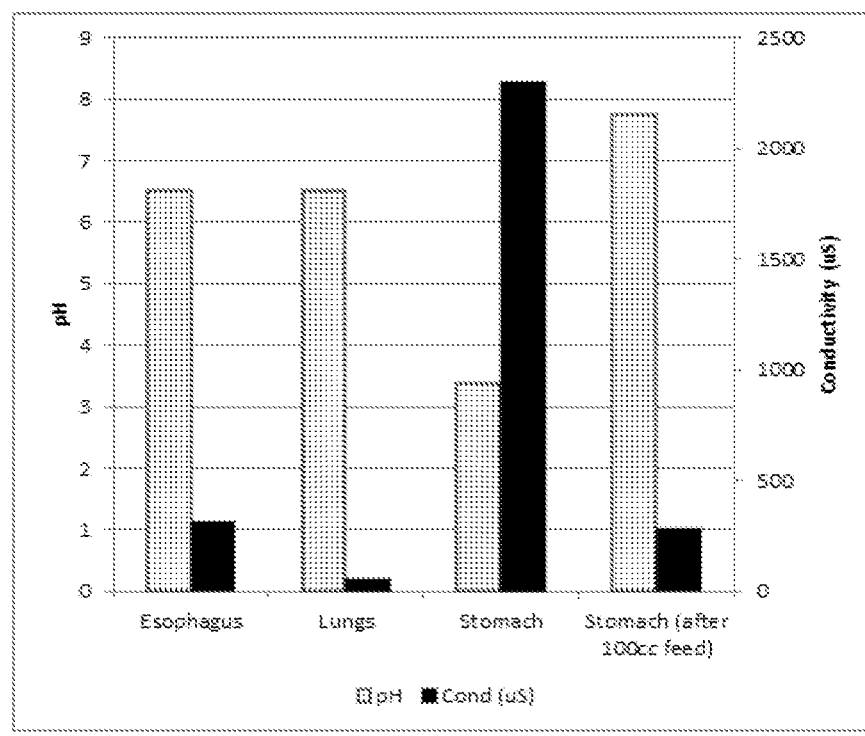
FIG. 56 shows pH and conductivity in various anatomical locations in a pig.

FIG. 56 shows pH and conductivity in various anatomical locations in a pig. This graph shows that using the combination of conductivity and pH increases the ability to identify the location of the sensors. For example, the pH of the esophagus and the pH of the lungs are similar here. However the pH of the esophagus or the lungs is very different than the pH of the stomach. The conductivity of the esophagus is different than that of the lungs. By using both the pH and the conductivity measurements in any given location, and/or the change of the pH and the conductivity measurements in any given location, the location of the sensors on the GRV measuring device can be determined. This allows the user to identify when the GRV measuring device is in the lungs by accident, in the esophagus, or in the stomach.

Figure 57:
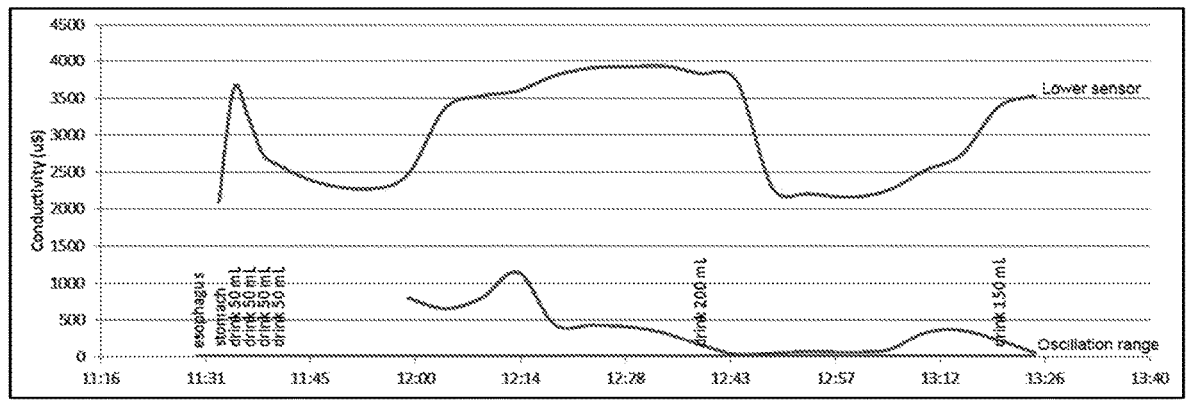
FIGS. 57 and 58 show conductivity and oscillations of conductivity in various locations in the anatomy before and after feeding.
Figure 58:
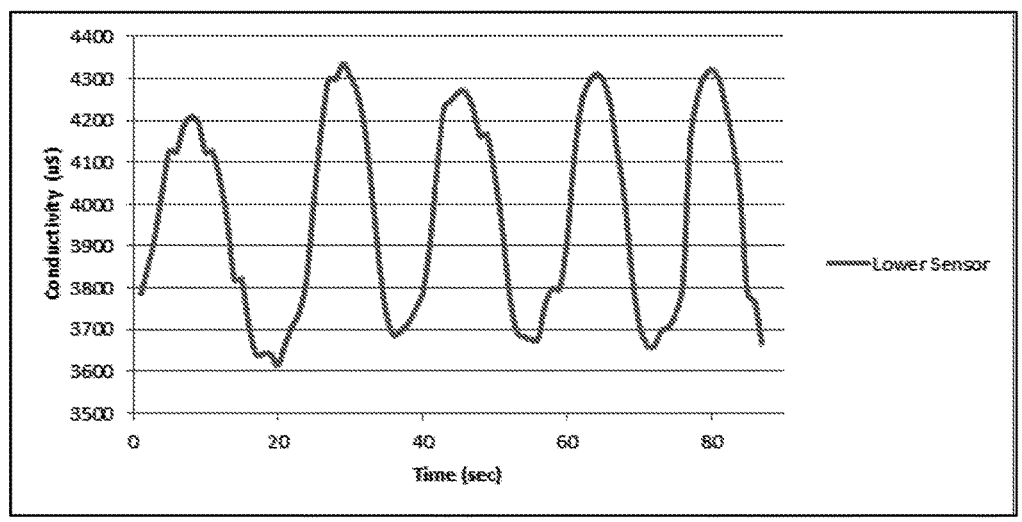

FIGS. 57 and 58 show conductivity and oscillations of conductivity in various locations in the anatomy of a human before and after feeding.

The human subject was initially in a fasting state. The GRV measuring device was inserted into the esophagus, and then into the stomach. The subject was fed almond milk three times over two hours, and conductivity measurements were taken throughout the experiment. The results are shown in FIG. 57

The conductivity in air is 0 µs, and as the GRM measuring device was inserted into the esophagus, the conductivity increased significantly. Once the device entered the stomach, the conductivity increased further. FIG. 57 shows that the conductivity drops after every feeding, and then rises again as the liquid is digested.

FIG. 58 shows a portion of the graph shown in FIG. 57 which has been magnified. The data was recorded at a sample rate of 1 Hz (1 reading per second). The increased resolution in this graph reveals twenty second oscillations that may be related to the peristaltic motion of the esophagus, stomach, and intestines. The amplitude of the oscillations is plotted at the bottom of the graph in FIG. 57. When the stomach is filled, the magnitude of the oscillations is diminished. Once the meal is diluted with gastric acid and the conductivity increases, the magnitude of the oscillations increases. Then as the meal is digested, the magnitude of the oscillations again decreases. FIG. 57 shows this trend, since the oscillation range increases before feedings, and then decreases after feeding. The location of the GRV measuring device and GRV may be measured by measuring conductivity, and/or the magnitude of conductivity oscillations.

Figure 59:
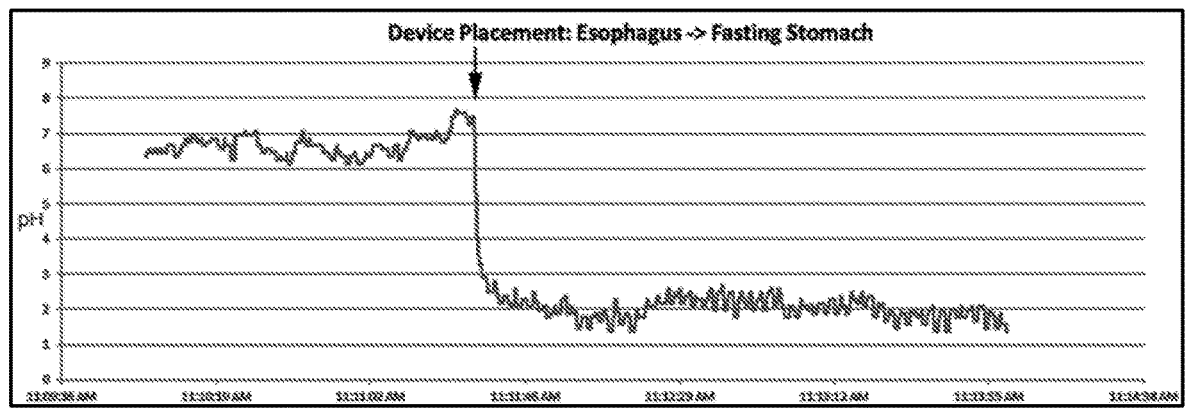
FIGS. 59 and 60 show pH and oscillations of pH in various locations in the anatomy.
Figure 60:
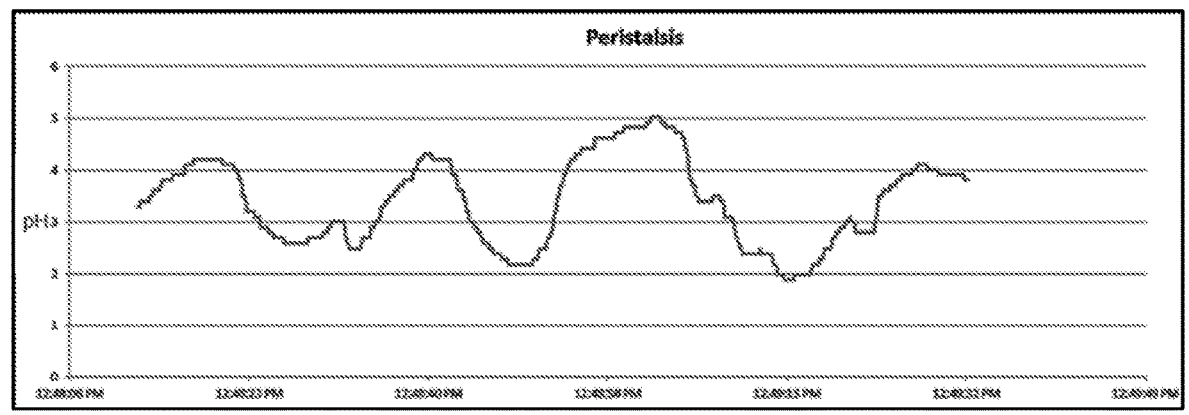

FIGS. 59 and 60 show pH and oscillations of pH while the GRV measuring device is being moved from the esophagus to the stomach of a fasting human.

The GRV measuring device was inserted from the esophagus into the stomach. The measured pH decreases when the stomach is entered.

FIG. 60 shows a portion of the graph shown in FIG. 59 which has been magnified. The pH measurements are shown to oscillate similar to those of the conductivity measurements.

Figure 61:
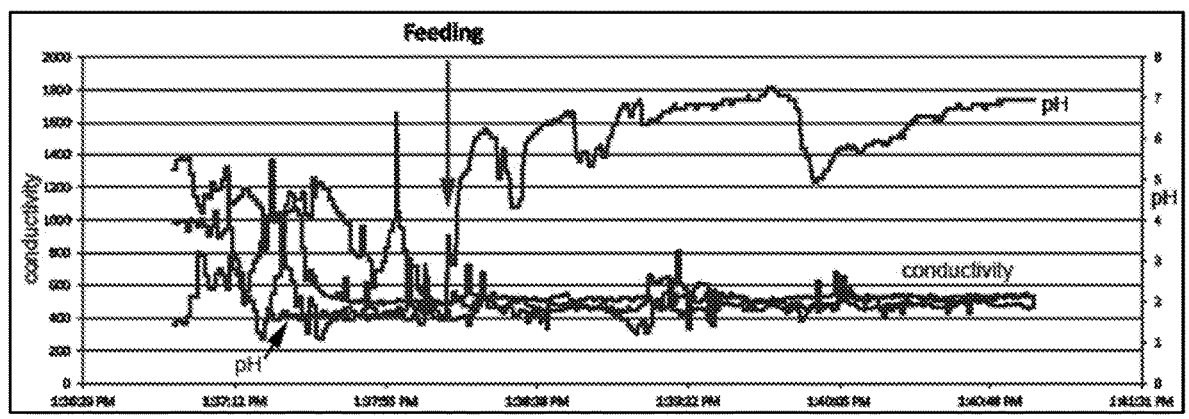
FIG. 61 shows conductivity and pH before and after feeding.

FIG. 61 shows both conductivity and pH measurements from the GRV measuring device during feeding. At feeding, the pH rises. The conductivity simultaneously drops and variability among sensors decreases. Although not visible in this graph, as digestion occurs and the stomach empties, pH decreases and conductivity rises. Variability in measurements is lower when the stomach is full due to the homogenous contents of the stomach. As food is digested, variability increases as peristaltic motions increase, and as the sensors move between areas of liquid and pockets of air.

By measuring both pH and conductivity, an algorithm that accounts for the mean and variability of pH and conductivity can be used to detect the various stages of digestion.

For example, food percentage during feeding can be calculated by applying empirically measured functions of ph and conductivity vs food % (food/(food+gastric fluid)). With a known volume of a known type of food delivered at any given time, the contents before and after feeding can be calculated:

VolBefore*FoodPercentBefore+FeedVol=VolAfter*FoodPercentAfter

Immediately before and after feeding, the following must be true:

VolAfter=VolBefore+FeedVol

Therefore, the initial equation can be written:

VolBefore*FoodPercentBefore+FeedVol=(VolBefore+FeedVol)*FoodPercentAfter

And this equation can be written as an equation in which we have all the information needed to calculate the volume prior to feeding:

VolBefore=FeedVol*((FoodPercentAfter−1)/(FoodPercentBefore−FoodPercentAfter))

Now that we know the total volume before and after feeding, and the food percentage before and after feeding, we can also calculate the food volume before and after feeding:

FoodVolBefore=VolBefore*FoodPercentBefore

FoodVolAfter=VolAfter*FoodPercentAfter

In an exemplary embodiment, the measurement technique of using conductivity, as well as conductivity combined with pH, can be combined with embodiments measuring the impedance of local tissue and fluids. In this exemplary embodiment, GRV is calculated using the impedance approach. GRV is also calculated using the conductivity approach, described and illustrated in FIG. 53-61. The resulting calculations from the impedance approach and the conductivity approach are then compared to each other via an algorithm. An exemplary algorithm will calculate the differences in the point calculations as well as the differences in calculations over time to determine an output signifying if the calculations are within a determined tolerance of being in agreement or an indication they are not in agreement or not enough information to determine if they are in agreement. The calculations may also be combined and/or smoothed by an algorithm using exemplary techniques that can be utilized in this embodiment, including but not limited to moving average, least squares, exponential smoothing, and LOESS/LOWESS regression. If the calculations are in agreement, this may be indicated in the controller, potentially signifying a higher confidence in the GRV and/or gastric emptying calculation.

In an exemplary apparatus, a common set of electrodes may be used to measure both impedance and conductivity. FIG. 22E shows an embodiment of a GRV sensor composed of four electrodes in a tetrapolar impedance measurement configuration. For measuring GRV, the source electrodes are 2205 and 2202 and the sense electrodes are 2206 and 2201. The conductivity sensor in this embodiment can be composed of just two electrodes, 2201 and 2202, to simultaneously inject, or introduce, current and sense voltage forming a bipolar conductivity measurement configuration. In an exemplary embodiment, the conductivity sensor can be composed of four electrodes. Electrodes 2201 and 2202 measure conductivity at the distal tip while electrodes 2205 and 2206 measure conductivity at the more proximal location on the tube. This configuration is similar to FIG. 53, where electrodes 5304 are equivalent to electrodes 2201 and 2202, and electrodes 5312 are equivalent to electrodes 2205 and 2206. Each electrode combination may simultaneously inject current and sense voltage forming a bipolar conductivity measurement configuration.

In an exemplary embodiment, the electrodes in FIG. 22e and FIG. 53 can be applied to a tube via conductive ink. Many different types of conductive ink can enable effectively collecting this data. In an exemplary embodiment, the conductive ink used is AGCL-675 Silver/Silver Chloride Ink provided by a company called Conductive Compounds. In these embodiments, the conductive ink is printed or otherwise applied directly to the surface of the feeding tube.

In an exemplary embodiment, pH is also calculated and used by an exemplary algorithm along with the impedance based calculation and conductivity based calculation of GRV. The algorithm would combine the pH measurement with the impedance and conductivity GRV measurements to determine a combined measurement or indication of GRV.

Some embodiments of the GRV measuring device may include feeding tube kink detection mechanisms, to detect if/when the feeding tube kinks, or doubles back on itself during placement, and also to detect if/when the tube become kinked after placement.

Figure 62:
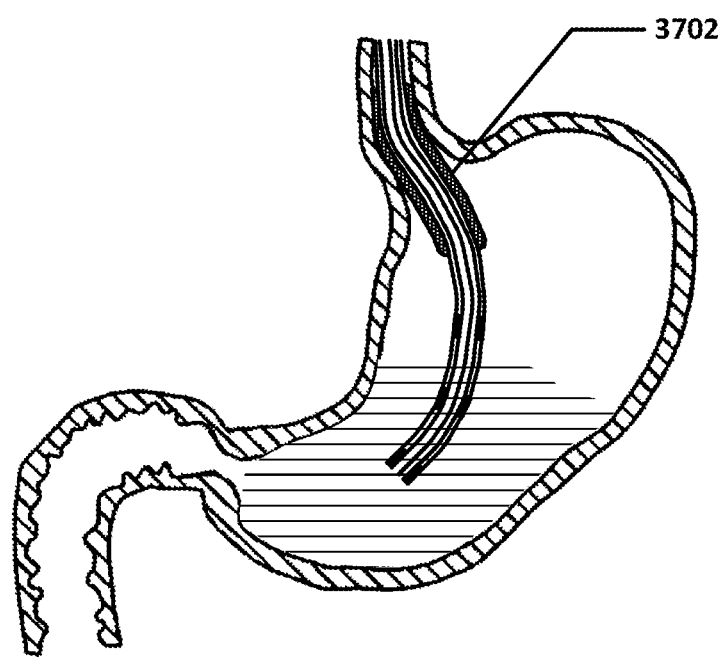
FIG. 62 shows an embodiment of the GRV measuring device with retention balloon.

Some embodiments of the GRV measuring device may include a retention mechanism, such as a retention balloon to keep the feeding tube in place after it is placed. The retention mechanism may be moveable with respect to the feeding openings of the feeding tube e to adjust to different size stomachs etc. The retention mechanism, such as a balloon, may be long, and/or only on one side of feeding tube so that some segment of the balloon is in the esophagus. In cases where the sealing mechanism is a balloon, the balloon may be compliant or non-compliant. The balloon may be a low pressure balloon. FIG. 62 shows an embodiment of the GRV measuring device with retention balloon 6202.

Some embodiments of the GRV measuring device may include the ability to test whether the feeding tube is bent or kinked. In one embodiment, the controller may introduce pressurized fluid (gas or liquid) into a lumen of the feeding tube and measure the pressure required for the fluid to flow through the lumen. A baseline pressure may be detected on a non-bent feeding tube to determine the unkinked pressure range. If/when the tube is bent or kinked, the pressure required will increase. The controller can measure and track this pressure over time and can determine the status of the feeding tube based on the absolute pressure, the relative pressure, the change of pressure or the slope of change of pressure over time.

Bending or kinking of the feeding tube may also be measured electronically, for example by measuring the proximity of the electrodes to each other. If the electrodes are closer to each other than their spacing along the feeding tube, then a kink or tight bend is likely present in the tube. This can be done by measuring impedance and/or conductance between electrodes. The pairing of electrodes can be changed by the controller to determine GRV vs electrode proximity. Alternatively, the same electrode pairing may be used.

Figure 63:
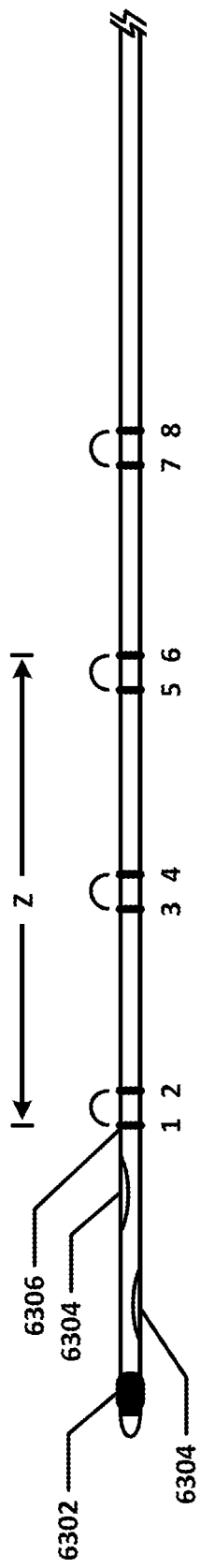
FIG. 63 shows a GRV measuring device with a pH sensor.
Figure 64:
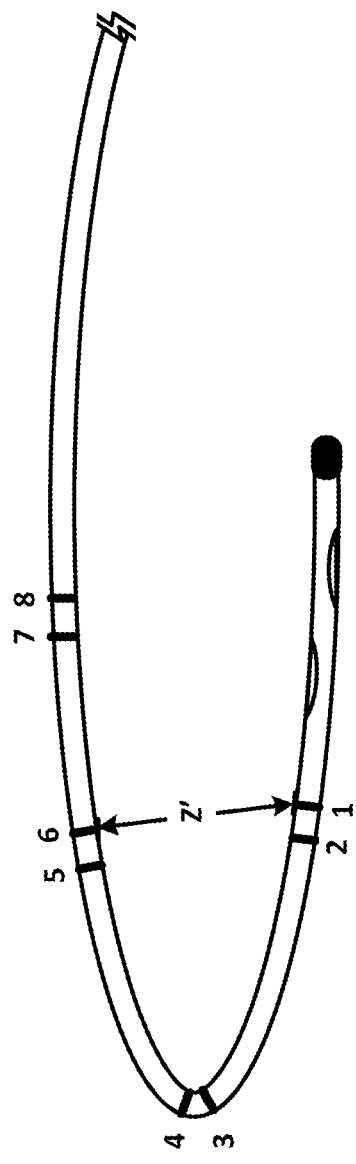
FIG. 64 shows a GRV measuring device with a pH sensor.

For example, see FIGS. 63 and 64. FIG. 63 shows a GRV measuring device with pH sensor 6302, openings (for feed) 6304, electrodes 6306 which include electrodes 1, 2, 3, 4, 5, 6, 7, and 8. Electrode pairs 1 and 2, 3 and 4, 5 and 6, and 7 and 8 are used as pairs during feeding and placement of the feeding tube to determine conductance/impedance at the electrode pair. However, different electrode pairs may also be used. For example, electrodes 1 and 6 may be used as a pair. The distance between electrode 1 and 6 can be determined via conductance/impedance. When the device is relatively straight, the distance between electrodes 1 and 6 is Z. If the distance becomes shorter, as in Z' shown in FIG. 64, the controller can either sound an alarm/alert, or automatically attempt an unkinking procedure to attempt to unkink the tube. Note that the detection of a kink may involve any electrode pair and the pair's relative distances from each other. For example, the conductance/impedance between original electrode pairs may not change in the presence of a kink, but the conductance/impedance between electrode pairs which are further apart may change. The combination may indicate a bend/kink situation.

ECG signal may also be detected by the electrodes on the GRV measuring device to determine the location of the tip, or other area, of the feeding tube relative to the heart—this may be used to help with placement of the feeding tube and also to detect kinks.

The electrodes may also be used to detect the electrical state of stomach muscle. A myoelectric signal, for example, may be detected to determine tube placement and tube kinks.

Anatomical pressure may also be measured using the GRV measuring device. Anatomical pressure may be measured through a feeding tube lumen, and/or via balloons or pressure sensors on or in the feeding tube to determine placement within the anatomy.

The GRV measuring device may be straightened, or stiffened, during or after placement, by blocking the feeding hole(s) with a balloon, balloons, valve(s) or other mechanism. The inner lumen of the feeding tube may then be pressurized to make it more rigid. Alternatively, a balloon may run inside the feeding lumen, or within another lumen, or on the outside of the feeding tube to stiffen/straighten the tube.

A variable durometer feeding tube may also be used to prevent kinks and help with placement. For example, the feeding tube of the GRV measuring device may be softer toward the stomach end.

A guide sheath may be used over the feeding tube portion of the GRV measuring device to control the durometer of the feeding tube during and after placement or to unkind the tube. The guide sheath may be slidable over the feeding tube to change the relative rigidity of different portions along the tube's length.

A guide stylet may be used inside a lumen of the feeding tube portion of the GRV measuring device to control the durometer of the feeding tube during and after placement or to unkind the tube. The guide stylet may be slidable within a feeding tube lumen to change the relative rigidity of different portions along the tube's length.

The GRV measuring device may include a sheath or lumen which houses a camera or an esophageal scope to view tube placement.

It is desirable also to prevent biofilm and/or bacteria buildup on and in at least the feeding tube portion of the GRV measuring device. This can be achieved by using anti-bacterial coatings and/or impregnating the device materials with anti-bacterial materials. For example, the feeding tube portion may be made from a material impregnated with Silver, or may be coated with Silver or any other antibacterial material. The coating/material may be only present on the inside of the feeding lumen.

In an exemplary embodiment, the electrodes and wires in FIG. 13, FIG. 22*e* and FIG. 53 can be applied to a tube via conductive ink containing silver, such as AGCL-675 Silver/Silver Chloride Ink provided by a company called Conductive Compounds. In this embodiment, the conductive ink impregnated with Silver may sufficiently provide an antibacterial effect.

UV, or other wavelength, light may be used inside the lumen of the feeding tube to disinfect the lumen. For example, a light fiber may be inserted within the feeding tube lumen and UV light shined inside the lumen between feedings. This may be done manually, or automatically. The light fiber may be inserted and removed between feedings or remain in place during feedings.

Figure 65:
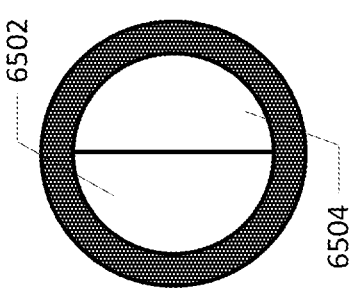
FIG. 65 shows a cross section of a feeding tube of the GRV measuring device.

The feeding tube lumen may be flushed between feedings with saline, an antibacterial flush or other suitable flush. The flushing fluid may enter the stomach or may be circulated (introduced into the lumen and removed from the lumen) so that none, or very little, enters the stomach. The introduction and removal of the flushing fluid may both be done through a single lumen or through more than one lumen. For example, the flushing fluid may be introduced and then sectioned out, or forced out with another fluid (liquid or gas). Alternatively the flushing fluid may be introduced through one lumen, and retrieved through another lumen. For example, the feed openings may be sealed or blocked from the flushing fluid with a balloon, sealing mechanism, valve etc. FIG. 65 shows a cross section of a feeding tube of the GRV measuring device with flush introduction lumen 6502 and flush retrieval lumen 6504. During feeding both lumens may be used to supply feed. Between feedings, the feed openings may be blocked and flushing fluid may be introduced through lumen 6502. Lumen 6502 is in fluid communication with lumen 6504 above the blocking of the feed openings so that the flushing fluid can then be retrieved via lumen 6504. This flushing process may be done manually or automatically by the controller between feedings.

Simple manufacturing and cost reduction of the GRV measurement device is also desirable. The electrical connections for the electrodes may be via wires, or electronically conductive ink which is printed onto the tube shaft. The connections may be on the outside of the shaft, embedded in the wall of the shaft, or in a lumen of the shaft. In one embodiment, electrical wires are between concentric tubes of the feeding tube shaft. In this configuration, they may be fixed in place, or allowed to float freely in the space between the tubes.

Figure 66:
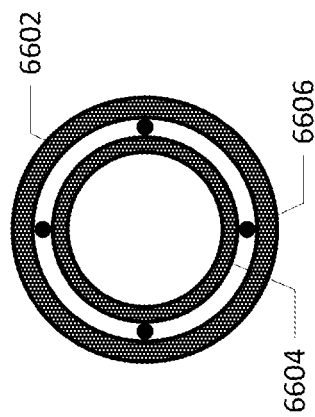
FIG. 66 shows an embodiment of the GRV measurement device.

FIG. 66 shows an embodiment of the GRV measurement device with outer tube 6602, inner tube 6604 and electrical wires 6606. The electrical wires are between the inner and outer tube, and connect to the controller on one end, and electrodes and/or pH sensors on the other end.

Figure 67:
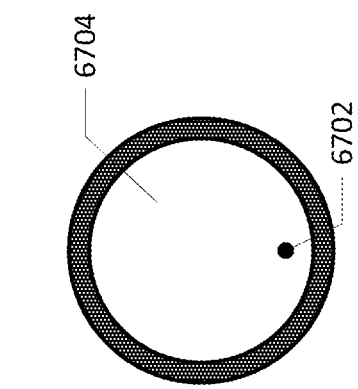
FIG. 67 shows an embodiment of the GRV measurement device.

FIG. 67 shows an embodiment of the GRV measurement device with wire (or wires) 6702 within the feeding lumen 6704. In this embodiment the wires or other electrical connection is inside the feeding lumen and may also be used for sterilization of the feeding lumen.

Figure 68:
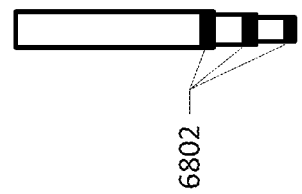
FIG. 68 shows an embodiment of the GRV measurement device.

FIG. 68 shows an embodiment of the GRV measurement device with telescoping tubing, each with one or more electrodes/sensors. In this embodiment, the electrical connection, i.e. wire, may pass between tubings similar to the embodiment shown in FIG. 66. Electrodes 6802 may be placed at or near the distal tip of each tube making them easier to manufacture.

Electrical connections may also be made with wires, or braids embedded or coextruded in the feeding tube tubing. Conductive polymer may be used for electrodes for easier, less costly manufacturing.

The pH measuring device may be a separate device, such as a guide wire or stylus with a pH sensor at the tip, which is used only tube placement and then optionally removed for feeding so that wiring for the pH sensor does not need to be incorporated into the feeding tube.

PH measurements may be obtained by using 2 electrode rings of dissimilar metals by measuring electron flow between the 2 electrodes.

Balloons or other spacers may be incorporated into the GRV measurement device at, or near, the electrodes to prevent the electrodes from contacting the stomach wall.

Neuromodulation may be used to induce contractions where the mobility of the stomach is slow (gastroparesis). The electrodes, or other electrodes may be used for this, by energizing them in sequence to stimulate the stomach/intestine/esophagus wall. The optimal frequency, or near frequency, would be that of natural peristaltic waves.

All embodiments disclosed herein may incorporate features from other embodiments disclosed herein. An automatic feedback loop may be used to automatically provide the right amount of feed to a patient, based on GRV measurements. The GRV measurement system may include an audible, or other type of, alarm when the volume of food within the stomach is unacceptable. The feeding tube may incorporate a pump, flow system, pressure system or other system to help clear the feeding tube of clogs if they occur. A clog detector may be incorporated into the system.

What is claimed is:

1. An apparatus for use with enteral feeding, comprising:
    an elongated body having a length configured for insertion into a stomach, wherein the elongated body defines at least one lumen through the length;
    at least one pair of electrodes located along the length of the elongated body and positionable for placement within the stomach;
    a controller in electrical communication with the at least one pair of electrodes, wherein the controller further comprises a display configured to display gastric residual volume (GRV) data over a period of time; and
    an additive element configured for per-oral insertion into the stomach and which is configured to alter a conductivity or impedance measured between the pair of electrodes, wherein the additive element is in communication through the at least one lumen into the stomach,
    wherein the controller is configured to measure a change in the conductivity or impedance between the pair of electrodes over a period of time, and
    wherein the controller is configured to determine a GRV of the stomach based on the measured conductivity or impedance and an increase or decrease of a ratio of stomach acid to the additive element introduced through the at least one lumen.

2. The apparatus of claim 1 wherein the at least one pair of electrodes is located near or at a distal tip of the elongated body.

3. The apparatus of claim 1 wherein the controller is further configured to determine a location of the elongated body within a subject based on the conductivity or impedance measured between the pair of electrodes.

4. The apparatus of claim 1 wherein the additive element comprises a controlled volume of liquid.

5. The apparatus of claim 1 wherein the additive element comprises a volume of water.

6. The apparatus of claim 1 wherein the additive element comprises a volume of feed.

7. The apparatus of claim 1 wherein the controller is further configured to measure the conductivity or impedance without and with the additive element.

8. The apparatus of claim 1 wherein the controller is further configured to measure the conductivity or impedance between the at least one pair of electrodes.

9. The apparatus of claim 1 wherein the elongated device comprises a feeding tube.

10. The apparatus of claim 1 wherein the elongated device is sized for insertion through a feeding tube.

11. The apparatus of claim 1 further comprising a feeding tube for use with the elongated body.

12. The apparatus of claim 1 further comprising a pH sensor located along the elongated body.

13. The apparatus of claim 1 wherein the at least one pair of electrodes is disposed along an outer surface and in proximity to a distal portion of the elongated body.

14. The apparatus of claim 13 wherein the at least one pair of electrodes is comprised of a conductive ink.

15. The apparatus of claim 14 wherein the conductive ink includes silver.

16. The apparatus of claim 1 wherein the controller is further configured to display or sound an alert when the GRV falls outside of an acceptable range.

17. The apparatus of claim 1 wherein the additive element is configured for per-oral or nasal insertion into the stomach.

18. A method of determining gastric residual volume (GRV) in a subject, comprising:
introducing an elongated body having a length into a stomach of the subject;
positioning at least one pair of electrodes located along the length of the elongated body within the stomach;
measuring a conductivity or impedance between the pair of electrodes within the stomach over a period of time;
determining the GRV of the stomach based on the measured conductivity or impedance;
displaying GRV data upon a display;
introducing an additive element through at least one lumen defined through the length of the elongated body and into the stomach such that the measured conductivity or impedance is altered; and
determining an increase or decrease of a ratio of stomach acid to the additive element to determine the GRV.

19. The method of claim 18 wherein measuring a conductivity or impedance comprising measuring via a controller in electrical communication with the at least one pair of electrodes.

20. The method of claim 18 wherein positioning further comprises determining a location of the elongated body within the subject based on the conductivity or impedance measured between the pair of electrodes.

21. The method of claim 18 wherein introducing an additive element comprises introducing a controlled volume of liquid into the stomach.

22. The method of claim 18 wherein introducing an additive element comprises introducing a controlled volume of water.

23. The method of claim 18 wherein introducing an additive element comprises introducing a volume of feed.

24. The method of claim 18 wherein introducing an additive element comprises measuring the conductivity or impedance prior to and after introduction of the additive element into the stomach to determine the GRV of the stomach.

25. The method of claim 18 wherein the elongated device comprises a feeding tube.

26. The method of claim 18 wherein the elongated device is sized for insertion through a feeding tube.

27. The method of claim 18 further comprising sensing a pH within the stomach via a pH sensor located along the length of the elongated body.

28. The method of claim 18 wherein the at least one pair of electrodes is disposed along an outer surface and in proximity to a distal portion of the elongated body.

29. The method of claim 28 wherein the at least one pair of electrodes is comprised of a conductive ink.

30. The method of claim 29 wherein the conductive ink includes silver.

31. The method of claim 18 further comprising displaying or sounding an alert when the GRV falls outside of an acceptable range.

32. The method of claim 18 wherein measuring a conductivity or impedance comprises measuring the conductivity or impedance between the at least one pair of electrodes.

33. The method of claim 18 wherein introducing the additive element into the stomach comprises introducing the additive element per-orally or nasally.

* * * * *

UNITED STATES PATENT AND TRADEMARK OFFICE
CERTIFICATE OF CORRECTION

| | | |
|---|---|---|
| PATENT NO. | : 11,406,320 B2 | |
| APPLICATION NO. | : 15/811433 | |
| DATED | : August 9, 2022 | |
| INVENTOR(S) | : Sutaria et al. | |

It is certified that error appears in the above-identified patent and that said Letters Patent is hereby corrected as shown below:

On the Title Page

1. Item (72) Please update inventor name from "Eliott BENNETT-GUERRERO" to "Elliott BENNETT-GUERRERO".

Signed and Sealed this
Eighteenth Day of October, 2022

Katherine Kelly Vidal
*Director of the United States Patent and Trademark Office*